(12) United States Patent
Mukerji et al.

(10) Patent No.: US 8,067,674 B2
(45) Date of Patent: Nov. 29, 2011

(54) DESATURASE GENES, ENZYMES ENCODED THEREBY, AND USES THEREOF

(75) Inventors: Pradip Mukerji, Gahanna, OH (US); Suzette L. Pereira, Westerville, OH (US); Yung-Sheng Huang, Upper Arlington, OH (US)

(73) Assignee: Abbott Laboratories, Abbott Park, IL (US)

( * ) Notice: Subject to any disclaimer, the term of this patent is extended or adjusted under 35 U.S.C. 154(b) by 30 days.

(21) Appl. No.: 12/409,211

(22) Filed: Mar. 23, 2009

(65) Prior Publication Data

US 2009/0226987 A1 Sep. 10, 2009

Related U.S. Application Data

(60) Continuation of application No. 11/621,446, filed on Jan. 9, 2007, now Pat. No. 7,723,503, which is a division of application No. 10/060,793, filed on Jan. 30, 2002, now Pat. No. 7,211,656.

(51) Int. Cl.
| | |
|---|---|
| A01H 5/00 | (2006.01) |
| C12N 15/82 | (2006.01) |
| C12N 5/10 | (2006.01) |
| C07H 21/04 | (2006.01) |

(52) U.S. Cl. ..... 800/298; 800/281; 435/410; 435/320.1; 435/419; 536/23.2

(58) Field of Classification Search .................... None
See application file for complete search history.

(56) References Cited

U.S. PATENT DOCUMENTS

| | | |
|---|---|---|
| 4,582,788 A | 4/1986 | Erlich |
| 4,666,701 A | 5/1987 | Horrobin et al. |
| 4,683,194 A | 7/1987 | Saika et al. |
| 4,683,202 A | 7/1987 | Mullis |
| 4,758,592 A | 7/1988 | Horrobin et al. |
| 4,826,877 A | 5/1989 | Stewart et al. |
| 4,943,674 A | 7/1990 | Houck et al. |
| 4,945,050 A | 7/1990 | Sanford et al. |
| 5,004,863 A | 4/1991 | Umbeck |
| 5,106,739 A | 4/1992 | Comai et al. |
| 5,107,065 A | 4/1992 | Shewmaker et al. |
| 5,116,871 A | 5/1992 | Horrobin et al. |
| 5,159,135 A | 10/1992 | Umbeck |
| 5,175,095 A | 12/1992 | Martineau et al. |
| 5,188,958 A | 2/1993 | Moloney et al. |
| 5,231,020 A | 7/1993 | Jorgensen |
| 5,416,011 A | 5/1995 | Hinchee et al. |
| 5,420,034 A | 5/1995 | Kridle et al. |
| 5,443,974 A | 8/1995 | Hitz et al. |
| 5,463,174 A | 10/1995 | Moloney et al. |
| 5,518,908 A | 5/1996 | Corbin et al. |
| 5,552,306 A | 9/1996 | Thomas et al. |
| 5,569,834 A | 10/1996 | Hinchee et al. |
| 5,589,379 A | 12/1996 | Kridl et al. |
| 5,614,393 A | 3/1997 | Thomas et al. |
| 5,631,152 A | 5/1997 | Fry et al. |
| 5,658,767 A | 8/1997 | Kyle et al. |
| 5,700,671 A | 12/1997 | Prieto et al. |
| 5,750,176 A | 5/1998 | Prieto et al. |
| 5,912,120 A | 6/1999 | Goldstein et al. |
| 6,150,144 A | 11/2000 | Akimoto et al. |
| 6,194,167 B1 | 2/2001 | Browse et al. |
| 2005/0112719 A1 | 5/2005 | Roessler et al. |

FOREIGN PATENT DOCUMENTS

| | | |
|---|---|---|
| EP | 0050424 | 9/1985 |
| EP | 0084796 | 5/1990 |
| EP | 0237362 | 3/1992 |
| EP | 0201184 | 12/1992 |
| EP | 0258017 | 6/1997 |
| WO | 93/11245 | 6/1993 |
| WO | 94/11516 | 5/1994 |
| WO | 95/24494 | 9/1995 |
| WO | 96/13591 A | 5/1996 |

OTHER PUBLICATIONS

Sakamoto et al, Plant Mol Biol 26: 249-263, 1994.*
FASEB Journal, Abstracts, Part 1, Abstract 3093, p. A532 (Experimental Biology 98, San Francisco, CA, Apr. 18-22, 1998.
Leslie, C.G., et al, Dietary (n-9) Eicosatrienoic Acid from a Cultured Fungus Inhibits Leukotriene B4 Synthesis in Rats and the Effect if Modified by Dietary Linoleic Acid, Amer Journ of Clin Nutrit, 126(6): 1534-1540 (1996).
Jareonkitmongkol, S., et al, "Production of an Eicosapentaenoic Acid-Containing Oil by a Delta-12 Desaturase-Defective Mutant of Mortierella alpina 1S-4", Journ of the Amer Oil Chemists' Soc., 70(2):119-123 (1993).
Pereira, S.L., et al, "A novel w-fatty acid desaturase involved in the biosynthesis of eicosapentaenoic acid," The Biohem Journ., 378(2): 665-671 (2004).
Ziboh, V.A., et al, "Metabolism of Polyunsaturated Fatty Acids by Skin Epidermal Enzymes: Generation of Anti-Inflammatory and Antiproliferative Metabolites 1-3", Amer. Journ. of Clin. Nutri, 71(1)Suppl: 361S-366S (Jan. 2000).
Broun et al, Science 282: 1315-1317, Nov. 13, 1998.
Van de Loo et al, PNAS, USA 92:6743-6747, Jul. 1995.
Doerks et al, TIG 14(6): 248-250, Jun. 1998.
Smith, et al, Nature Biotechnology 15: 1222-1223, Nov. 15, 1997.
Brenner, S.E., TIG 15(4): 132-133, Apr. 1999.
Bork et al, TIG 12(10): 425-427, Oct. 1996.

(Continued)

*Primary Examiner* — Elizabeth McElwain

(57) ABSTRACT

Disclosed are isolated polynucleotides encoding an omega-3 desaturase and a delta-12 desaturase, the enzymes encoded by the isolated polynucleotides, vectors containing the isolated polynucleotides, transgenic hosts that contain the isolated polynucleotides that express the enzymes encoded thereby, methods for producing the desaturase enzymes, and method of using the enzymes to make polyunsaturated fatty acids. The isolated polynucleotides are derived from a fungus, *Saprolegnia diclina* (ATCC 56851). In particular, omega-3-desaturase may be utilized, for example, in the conversion of arachidonic acid (AA) to eicosapentaenoic acid (EPA). Delta-12 desaturase may be used, for example, in the conversion of oleic acid (OA) to linoleic (LA). EPA or polyunsaturated fatty acids produced therefrom may be added to pharmaceutical compositions, nutritional compositions, animal feeds, as well as other products such as cosmetics.

15 Claims, 14 Drawing Sheets

OTHER PUBLICATIONS

Gribskov, et al, Nucl. Acids Res. 1986 14(16): 6745-6763.
Smith & Waterman, Advances in Applied Mathematics 2:482-489 (1981).
Needleman & Wunsch, J. Mol. Biol. 48:443-453 (1970).
Pearson & Lipman, Proc. Natl. Acad. Sci. (USA) 85(8): 2444-2448 (1988).
Shanklin, J.E., McDonough, V.M., and Martin, C.E. (1994) Biochemistry 33, 12787-12794.
Altschul et al, Nucleic Acids Research 1997, vol. 25 p. 3389-3402.
Turner, R. and Foster, G.D. (1995) Molecular Biotechnology 3:225-236.
Ingelbrecht, et al, (1989) Plant Cell 1:671-680.
Klein, et al, (1987) Nature (London) 327:70-73.
Ishida Y., et al, 1996, Nature Biotech. 14:745-750.
Mullis, et al, Cold Spring Harbor Symp. Quant. Biol. 51:263-273 (1986).
Jones, et al, (1985) EMBO J. 4:2411-2418.
De Almeida, et al, (1989) Mol. Gen. Genetics 218:78-86.
Schnieke, et al, Science 278:2130-2133 (1997).
Stuckey, J.E., McDonough, V.M. and Martin, C.E. (1990) J. Biol. Chem. 265, 20144-20149.
McCabe, et al, BiolTechnology 6:923 (1988).
Christou, et al., Plant Physiol. 87:671-674 (1988).
Cheng, et al., Plant Cell Rep. 15:653-657 (1996).
McKently, et al., Plant Cell Rep. 14:699-703 (1995).
Grant, et al., Plant Cell Rep. 15:254-258 (1995).
Bytebier, et al., Proc. Natl. Acad. Sci. (USA) 84:5345-5349, (1987).
Wan and Lemauxs, Plant Physiol 104: 37 (1994).
Rhodes, et al., Science 240: 204-207 (1988) (Abstract Only).
Gordon-Kamm, et al., Plant Cell 2:603-618 (1990).
Fromm, et al., BiolTechnology 8:833 (1990).
Koziel, et al., BiolTechnology 11:194, (1993).
Armstrong, et al., Crop Science 35:550-557 (1995).
Somers, et al., BiolTechnology 10:1589-1594 (1992).
Horn, et al., Plant Cell Rep. 7:469 (1988).
Toriyama, et al., TheorAppl. Genet. 205:34 (1986).
Part, et al., Plant Mol. Biol. 32:1135-1148 (1996).
Abedinia, et al., Aust. J. Plant Physiol. 24:133-141 (1997).
Zhang and Wu, Theor. Appl. Genet. 76:835 (1988).
Zhang, et al., Plant Cell Rep. 7:379 (1988).
Battraw and Hall, Plant Sci. 86:191-202 (1992).
Christou et al. Bio/Technology 9:957 (1991).
De la Pena et al., Nature 325:274-276 (1987).
Bower and Birch, Plant J. 2:409 (1992).
Wang et al., Bio/Technology 10:691-696 (1992).
Vasil et al., Bio/Technology 10:667 (1992).
Marcotte et al., Nature 335:454-457 (1988).
Marcotte et al., Plant Cell 1:523-532 (1989).
McCarty et al., Cell 66:895-905 (1991).
Hattori et al., Genes Dev. 6:609-618 (1992).
Goff et al., EMBO J. 9:2517-2522 (1990).
Maliga et al., Methods in Plant Molecular Biology, Cold Spring Harbor Press (1995).
Birren et al., Genome Analysis: Detecting Genes, 1, Cold Spring Harbor New York (1998).
Birren et al., Genome Analysis: Analyzing DNA, 2, Cold Spring Harbor New York (1998).
Plant Molecular Biology: A Laboratory Manual, eds., Clark, Springer, New York (1997).
Brenner et al., Adv. Exp. Med. Biol. vol. 83, p. 85-101, 1976.
Willoughby L. G. (1983) Trans Br. Mycol. Soc. vol. 80, p. 421-435.
McCarty et al., Cell. vol. 66 p. 895-905 (1991).

* cited by examiner

Gene Sequence of *sdd17*, an Omega-3 Fatty Acid Desaturase Gene
from *Saprolegnia diclina* (ATCC 56851)

```
   1  ATGACTGAGG ATAAGACGAA GGTCGAGTTC CCGACGCTCA CGGAGCTCAA
  51  GCACTCGATC CCGAACGCGT GCTTTGAGTC GAACCTCGGC CTCTCGCTCT
 101  ACTACACGGC CCGCGCGATC TTCAACGCGT CGGCCTCGGC GGCGCTGCTC
 151  TACGCGGCGC GCTCGACGCC GTTCATTGCC GATAACGTTC TGCTCCACGC
 201  GCTCGTTTGC GCCACCTACA TCTACGTGCA GGGCGTCATC TTCTGGGGCT
 251  TCTTCACGGT CGGCCACGAC TGCGGCCACT CGGCCTTCTC GCGCTACCAC
 301  AGCGTCAACT TTATCATCGG CTGCATCATG CACTCTGCGA TTTTGACGCC
 351  GTTCGAGAGC TGGCGCGTGA CGCACCGCCA CCACCACAAG AACACGGGCA
 401  ACATTGATAA GGACGAGATC TTTTACCCGC ACCGGTCGGT CAAGGACCTC
 451  CAGGACGTGC GCCAATGGGT CTACACGCTC GGCGGTGCGT GGTTTGTCTA
 501  CTTGAAGGTC GGGTATGCCC CGCGCACGAT GAGCCACTTT GACCCGTGGG
 551  ACCCGCTCCT CCTTCGCCGC GCGTCGGCCG TCATCGTGTC GCTCGGCGTC
 601  TGGGCCGCCT TCTTCGCCGC GTACGCGTAC CTCACATACT CGCTCGGCTT
 651  TGCCGTCATG GGCCTCTACT ACTATGCGCC GCTCTTTGTC TTTGCTTCGT
 701  TCCTCGTCAT TACGACCTTC TTGCACCACA ACGACGAAGC GACGCCGTGG
 751  TACGGCGACT CGGAGTGGAC GTACGTCAAG GGCAACCTCT CGAGCGTCGA
 801  CCGCTCGTAC GGCGCGTTCG TGGACAACCT GAGCCACCAC ATTGGCACGC
 851  ACCAGGTCCA CCACTTGTTC CCGATCATTC CGCACTACAA GCTCAACGAA
 901  GCCACCAAGC ACTTTGCGGC CGCGTACCCG CACCTCGTGC GCAGGAACGA
 951  CGAGCCCATC ATCACGGCCT TCTTCAAGAC CGCGCACCTC TTTGTCAACT
1001  ACGGCGCTGT GCCCGAGACG GCGCAGATCT TCACGCTCAA AGAGTCGGCC
1051  GCGGCCGCCA AGGCCAAGTC GGACTAA
```

FIG.2

Amino Acid Sequence of an Omega-3 Fatty Acid Desaturase (SDD17) from *Saprolegnia diclina* (ATCC 56851)

```
  1 MTEDKTKVEF PTLTELKHSI PNACFESNLG LSLYYTARAI FNASASAALL
 51 YAARSTPFIA DNVLLHALVC ATYIYVQGVI FWGFFTVGHD CGHSAFSRYH
101 SVNFIIGCIM HSAILTPFES WRVTHRHHHK NTGNIDKDEI FYPHRSVKDL
151 QDVRQWVYTL GGAWFVYLKV GYAPRTMSHF DPWDPLLLRR ASAVIVSLGV
201 WAAFFAAYAY LTYSLGFAVM GLYYYAPLFV FASFLVITTF LHHNDEATPW
251 YGDSEWTYVK GNLSSVDRSY GAFVDNLSHH IGTHQVHHLF PIIPHYKLNE
301 ATKHFAAAYP HLVRRNDEPI ITAFFKTAHL FVNYGAVPET AQIFTLKESA
351 AAAKAKSD*
```

FIG.3

Comparative analysis of *S. diclina* Delta 17-desaturase (SDD17.pep)
& *Synechocystis* sp. Delta 15-desaturase (SYCDESB)

Frame: 2 initn: 733 initl: 305 opt: 689 Z-score: 996.8 expect(): 1.5e-47
 40.9% identity in 269 aa overlap
 (76-336:204-471)

```
                 50        60        70        80        90       100
SDD17.pep     SAALLYAARSTPFIADNVLLHALVCATYIYVQGVIFWGFFTVGHDCGHSAFSRYHSVNFI
                          :||::||::|:|||||||::||: :::|
SYCDESB       YFFLDVGLIAGFYALAAYLDSWFFYPIFWLIQGTLFWSLFVVGHDCGHGSFSKSKTLNNW
                 530       560       590       620       650       680

110       120       130       140       150       160
SDD17.pep     IGCIMHSAILTPFESWRVTHRHHHKNTGNIDKDEIFYPHRSVKDLQ----DVRQWVYTLG
              || : |: ||:|:::||::|| || |||||| || :||   | |  :     |
SYCDESB       IGHLSHTPILVPYHGWRISHRTHHANTGNIDTDESWYPVSEQKYNQMAWYEKLLRFYLPL
                 710       740       770       800       830       860

170       180       190       200       210       220
SDD17.pep     GAWFVYLKVGYAPRTMSHFDPWDPLLL-RRASAVIVSLGVWAAFFAAYAYLTYSLGFAVM
              |: :||     |  ||| | :||:   : :||::  :  ||| :   ::||:::|:  :
SYCDESB       IAYPIYLFRRSPNRQGSHFMPGSPLFRPGEKAAVLTSTFALAAFVGFLGFLTWQFGWLFL
                 890       920       950       980       1010      1040

230       240       250       260       270       280
SDD17.pep     GLYYYAPLFVFASFLVITTFLHHNDEATPWYGDSEWTYVKGNLSSVDRSYGAFVDNLSHH
              :| || :||: :| ::||||::: ||| ::| ::||||::||| |:: : |
SYCDESB       LKFYVAPYLVFVVWLDLVTFLHHTEDNIPWYRGDDWYFLKGALSTIDRDYG-FINPIHHD
                 1070      1100      1130      1160      1190      1220

290       300       310       320       330
SDD17.pep     IGTHQVHHLFPIIPHYKLNEATKHFAAAYPHLVRRNDEPIITAFFKT---AHLFVNYGAV
              ||||  :||:|  :|||||  :||:  :      : |  :||||||||       |:  | |:
SYCDESB       IGTHVAHHIFSNMPHYKLRRATEAIKPILGEYYRYSDEPIWQAFFKSYWACHFVPNQGSG
                 1250      1280      1310      1340      1370      1400

340       350
SDD17.pep     PETAQIFTLKESAAAAKAKSD

SYCDESB       VYYQSPSNGGYQKKPXLILIESNQHREGRQYXMVLLPSDRLMRSMEEVKQSHSKRSALNQ
                 1430      1460      1490      1520      1550      1580
```

FIG.4

Comparative analysis of *S. diclina* Delta 17-desaturase (SDD17.pep)
*C. elegans* Delta 17-desaturase (CELEFAT)

Frame: 1 initn: 490 initl: 222 opt: 502 Z-score: 724.0 expect(): 2.3e-32
31.6% identity in 310 aa overlap
(2-303:49-347)

```
                                              10        20        30
SDD17.pep                            MTEDKTKVEFPTLTELKHSIPNACFESNLGL
                                     | ::  ::::|| :  ::::||  ||| :|
CELFAT      VTGGDVLVDARASLEEKEAPRDVNANTKQATTEEPRIQLPTVDAFRRAIPAHCFERDLVK
                    80        110       140       170       200       230

40        50        60        70        80        90
SDD17.pep   SLYYTARAIFNASASAALLYAARSTPFIADNVLLHALVCATYIYVQGVIFWGFFTVGHDC
            |:| |::   |||      :|:   |: ||    ::    ||:  ::|:||||
CELFAT      SIRYLVQDF------AALTILYFALPAFEYFGLFGYLVWNIFM---GVFGFALFVVGHDC
                    260       290       320       350       380

100       110       120       130       140
SDD17.pep   GHSAFSRYHSVNFIIGCIMHSAILTPFESWRVTHRHHHKNTGNIDKD--EIFYPHRSVKD
            |::||  :::| :||| |  | :::|:   |:  :|: ||  |::||||  :::   :: :
CELFAT      LHGSFSDNQNLNDFIGHIAFSPLFSPYFPWQKSHKLHHAFTNHIDKDHGHVWIQDKDWEA
                    410       440       470       500       530       560

150       160       170       180       190       200
SDD17.pep   LQDVRQWV----YTLGGAWF-VYLKVGYAPRTMSHFDPWDPLLLRRASAVIVSLGVWAAF
            : : ::|       ::    |||| |:    ||| |::  |::| :: |    ::
CELFAT      MPSWKRWFNPIPFSGWLKWFPVYTLFGFC--DGSHFWPYSSLFVRNSDRVQCVISGICCC
                    590       620       650       680       710       740

210       220       230       240       250       260
SDD17.pep   FAAYAYLTYSLGFAVMGLYYYAPLFVFASFLVITTFLHHNDEATPWYGDSEWTYVKGNLS
            ||  || : :::   ||::||  |:  :|||:|:| |:::   :  ::||::|:|: :
CELFAT      VCAYIALTIAGSYSNWFWYYWVPLSFFGLMLVIVTYLQHVDDVAEVYEADEWSFVRGQTQ
                    770       800       830       860       890       920

270       280       290       300       310       320
SDD17.pep   SVDRSYGAFVDNLSHHI-GTHQVHHLFPIIPHYKLNEATKHFAAAYPHLVRRNDEPIITA
            ::|| ||  :|:   |||   | :||:|  ||||:|   ||||:  ||||:
CELFAT      TIDRYYGLGLDTTMHHITDGHVAHHFFNKIPHYHLIEATEGVKKVLEPLSDTQYGYKSQV
                    950       980       1010      1040      1070      1100

330       340       350
SDD17.pep   FFKTAHLFVNYGAVPETAQIFTLKESAAAAKAKSD

CELFAT      NYDFFARFLWFNYKLDYLVHKTAGIMQFRTTLEEKAKAKXKNIPCRSRVQQQLLRFHRFC
                    1130      1160      1190      1220      1250      1280
```

FIG.5

Gene Sequence of *sdd12*, a Delta 12-Desaturase Gene
from *Saprolegnia diclina* (ATCC 56851)

```
   1  ATGTGCAAAG GTCAAGCTCC TTCCAAGGCC GACGTGTTCC ACGCTGCGGG
  51  GTACCGCCCG GTCGCCGGCA CGCCCGAGCC GCTGCCGCTG GAGCCCCCGA
 101  CGATCACGCT CAAGGACCTG CGCGCGGCGA TCCGGCCCA CTGCTTTGAG
 151  CGCAGCGCTG CCACTAGCTT TTACCATTTG GCCAAGAACC TTGCGATCTG
 201  CGCCGGCGTG TTCGCCGTTG CCTCAAGCT CGCGGCTGCC GACTTGCCGC
 251  TCGCGGCCAA GCTGGTCGCG TGGCCCATCT ACTGGTTCGT CCAGGGCACG
 301  TACTTTACGG GCATCTGGGT CATTGCGCAC GAATGCGGCC ACCAGGCGTT
 351  CTCGGCGTCC GAGATCCTCA ACGACACGGT CGGTATCATT CTTCACTCGC
 401  TCCTCTTTGT GCCGTACCAC AGCTGGAAGA TCACGCACCG CCGCCACCAC
 451  TCCAACACGG GCAGCTGCGA GAACGACGAG GTGTTTACGC CGACGCCGCG
 501  GTCCGTCGTC GAGGCCAAGC ACGACCACTC GCTCCTCGAA GAGAGCCCGC
 551  TCTACAACCT GTACGGCATC GTCATGATGC TTCTCGTGGG CTGGATGCCG
 601  GGCTACCTCT TCTTCAACGC GACCGGCCCG ACCAAGTACG CTGGCCTCGC
 651  CAAGTCGCAC TTCAACCCGT ACGCAGCCTT TTTCCTCCCA AAGGAGCGCC
 701  TCAGCATCTG GTGGAGCGAC CTCTGCTTCC TCGCGGCCTT GTACGGCTTT
 751  GGCTACGGCG TCTCGGTCTT CGGCCTCCTC GATGTCGCCC GCCACTACAT
 801  CGTGCCGTAC CTCATTTGCA ACGCGTACCT CGTGCTCATC ACGTACCTCC
 851  AGCACACGGA TACGTACGTG CCCCACTTCC GCGGCGACGA GTGGAACTGG
 901  CTGCGCGGCG CGCTCTGCAC CGTCGACCGC TCGTTCGGCG CGTGGATCGA
 951  CAGCGCGATC CACCACATTG CCGACACGCA CGTGACGCAC ACATTTTCT
1001  CCAAGACGCC CTTCTACCAC GCGATCGAGG CGACCGACGC CATCACGCCC
1051  CTCCTCGGCA AGTACTACCT CATCGACCCG ACGCCGATCC CGCTGGCGCT
1101  CTGGCGCTCG TTCACGCACT GCAAGTACGT CGAGGACGAC GGCAACGTTG
1151  TGTTTTACAA GCGCAAGCTC GAGGAAAAGT AA
```

FIG.6

Amino Acid Sequence of a Delta 12-Desaturase (SDD12) from *Saprolegnia diclina* (ATCC 56851)

```
  1  MCKGQAPSKA DVFHAAGYRP VAGTPEPLPL EPPTITLKDL RAAIPAHCFE
 51  RSAATSFYHL AKNLAICAGV FAVGLKLAAA DLPLAAKLVA WPIYWFVQGT
101  YFTGIWVIAH ECGHQAFSAS EILNDTVGII LHSLLFVPYH SWKITHRRHH
151  SNTGSCENDE VFTPTPRSVV EAKHDHSLLE ESPLYNLYGI VMMLLVGWMP
201  GYLFFNATGP TKYAGLAKSH FNPYAAFFLP KERLSIWWSD LCFLAALYGF
251  GYGVSVFGLL DVARHYIVPY LICNAYLVLI TYLQHTDTYV PHFRGDEWNW
301  LRGALCTVDR SFGAWIDSAI HHIADTHVTH HIFSKTPFYH AIEATDAITP
351  LLGKYYLIDP TPIPLALWRS FTHCKYVEDD GNVVFYKRKL EEK*
```

FIG.7

Comparative analysis of *S. diclina* Delta 12-desaturase (SDD12.pep)
& *G. hirsutum* Delta 12-desaturase (GH06DES)

Frame: 3 initn: 992 initl: 413 opt: 1086 Z-score: 1531.8 expect(): 2.3e-77
 45.6% identity in 379 aa overlap
 (9-380:14-384)

```
                      10        20         30         40
SDD12.pep      MCKGQAPSKADVFHAAGYRPVAGTPEP------LPLEPPTITLKDLRAAIPAHC
               ||:  |:|  |:  |   |        :|:| | :|| :::  ||| ||
GH06DESAT    LRVSSTWRXTAFFKASKMGAGGRMPIDGIKEENRGSVNRVPIEKPPFTLGQIKQAIPPHC
              10        40        70       100       130       160

50        60        70        80        90       100
SDD12.pep      FERSAATSFYHLAKNLAICAGVFAVGLKLAAADLPLAAKLVAWPIYWFVQGTYFTGIWVI
               |:||   ||  ::::|:| :  : ::  :  ||      ::|||:|| :|| :||:|||
GH06DESAT      FRRSLLRSFSYVVHDLCLASFFYYIATSYFHF-LPQPFSYIAWPVYWVLQGCILTGVWVI
              190       220       250       280       310       340

110       120       130       140       150       160
SDD12.pep      AHECGHQAFSASEILNDTVGIILHSLLFVPYHSWKITHRRHHSNTGSCENDEVFTPTPRS
               ||| ||:||  : ::||||:||| |:||| ||||:||||'|||| | |||| |:| |:|
GH06DESAT      AHEWGHHAFRDYQWVDDTVGLILHSALLVPYFSWKISHRRHHSNTGSMERDEVFVPKPKS
              370       400       430       460       490       520

170       180       190       200       210       220
SDD12.pep      VVEAKHDHSLLEESPLYNLYGIVMHLLVGWMPGYLFFNATGPTKYAGLAKSHFNPYAAFF
               :     :  ::|  : ::|: |:|| ||  ||::|| ||:::  |     ||:|||: ::
GH06DESAT      KLSC---FAKYLNNPPGRVLSLVVTLTLGW-PMYLAFNVSG--RYYDRLASHYNPYGPIY
              550       580       610       640       670

230       240       250       260       270       280
SDD12.pep      LPKERLSIWWSDLCFLAALYGFGYGVSVFGLLDVARHYIVPYLICNAYLVLITYLQHTDT
               :|||:::  || ::|::   :::  ||   :   | ||| || ||:||||||||| :
GH06DESAT      SDRERLQVYISDTGIFAVIYVLYKIAATKGLAWLLCTYGVPLLIVNAFLVLITYLQHTHS
              700       730       760       790       820       850

290       300       310       320       330       340
SDD12.pep      YVPHFRGDEWNWLRGALCTVDRSFGAWIDSAIHHIADTHVTHHIFSKTPFYHAIEATDAI
               :||: ::||:||||||| |:|||:||:   :::::|:|:||||:||:||  ||||:|| ||
GH06DESAT      ALPHYDSSEWDWLRGALSTMDRDFGV-LNKVFHNITDTHVAHHLFSTMPHYHAMEATKAI
              880       910       940       970      1000      1030

350       360       370       380       390
SDD12.pep      TPLLGKYYLIDPTPIPLALWRSFTHCKYVEDDGNVVFYKRKLEEK
               |:||||| :| |||  |:|| :|  :| |||
GH06DESAT      KPILGKYYPFDGTPIYKAMWREAKECLYVEPDVGGGGGGGSKGVFWYRNKFXRPTNCLIAG
             1060      1090      1120      1150      1180      1210
```

FIG.8

Sequence ID:

Sequence ID 1
5'-ATC CGC GCC GCC ATC CCC AAG CAC TGC TGG GTC AAG-3'

Sequence ID 2
5'- GCC CTC TTC GTC CTC GGC CAY GAC TGC GGC CAY GGC TCG TTC TCG-3'

Sequence ID 3
5'-GAG RTG GTA RTG GGG GAT CTG GGG GAA GAR RTG RTG GRY GAC RTG-3'

Sequence ID 4
5'-CCC TAC CAY GGC TGG CGC ATC TCG CAY CGC ACC CAY CAY CAG AAC-3'

Sequence ID 5
5'-GTT CTG RTG RTG GGT CCG RTG CGA GAT GCG CCA GCC RTG GTA GGG-3'

Sequence ID 6
5'- GGC TCG CAC TTC SAC CCC KAC TCG GAC CTC TTC GTC-3'

Sequence ID 7
5'- GAC GAA GAG GTC CGA GTM GGG GTW GAA GTG CGA GCC-3'

Sequence ID 8
5'- GCG CTG GAK GGT GGT GAG GCC GCC GCG GAW GSA CGA CCA-3'

Sequence ID 9
5'- CTG GGG GAA GAG RTG RTG GAT GAC RTG GGT GCC GAT GTC RTG RTG-3'

Sequence ID 10
5'- GGT GGC CTC GAY GAG RTG GTA RTG GGG GAT CTK GGG GAA GAR RTG-3'

Sequence ID 11
5'-GAG RTG GTA RTG GGG GAT CTG GGG GAA GAR RTG RTG GRY GAC RTG-3'

Sequence ID 12
5'-TAC GCG TAC CTC ACG TAC TCG CTC G-3'

Sequence ID 13
5'-TTC TTG CAC CAC AAC GAC GAA GCG ACG-3'

Sequence ID 14
5'-GGA GTG GAC GTA CGT CAA GGG CAA C-3'

Sequence ID 15
5'-TCA AGG GCA ACC TCT CGA GCG TCG AC-3'

Sequence ID 16
5'-CCC AGT CAC GAC GTT GTA AAA CGA CGG CCA G-3'

FIG.9A

Sequence ID 17
5'- AGC GGA TAA CAA TTT CAC ACA GGA AAC AGC -3'

Sequence ID 18
5'-GGT AAA AGA TCT CGT CCT TGT CGA TGT TGC-3'

Sequence ID 19
5'-GTC AAA GTG GCT CAT CGT GC-3'

Sequence ID 20
5'-CGA GCG AGT ACG TGA GGT ACG CGT AC-3'

Sequence ID 21
5'-TCA ACA GAA TTC ATG ACC GAG GAT AAG ACG AAG GTC GAG TTC CCG-3'

Sequence ID 22
5'-AAA AGA AAG CTT CGC TTC CTA GTC TTA GTC CGA CTT GGC CTT GGC-3'

Sequence ID 23
5'-TCA ACA AAG CTT ATG ACC GAG GAT AAG ACG AAG GTC GAG TTC CCG-3'

Sequence ID 24
5'-AAA AGA GAA TTC CGC TTC CTA GTC TTA GTC CGA CTT GGC CTT GGC-3'

Sequence ID 25
```
   1 ATGACTGAGG ATAAGACGAA GGTCGAGTTC CCGACGCTCA CGGAGCTCAA
  51 GCACTCGATC CCGAACGCGT GCTTTGAGTC GAACCTCGGC CTCTCGCTCT
 101 ACTACACGGC CCGCGCGATC TTCAACGCGT CGGCCTCGGC GGCGCTGCTC
 151 TACGCGGCGC GCTCGACGCC GTTCATTGCC GATAACGTTC TGCTCCACGC
 201 GCTCGTTTGC GCCACCTACA TCTACGTGCA GGGCGTCATC TTCTGGGGCT
 251 TCTTCACGGT CGGCCACGAC TGCGGCCACT CGGCCTTCTC GCGCTACCAC
 301 AGCGTCAACT TTATCATCGG CTGCATCATG CACTCTGCGA TTTTGACGCC
 351 GTTCGAGAGC TGGCGCGTGA CGCACCGCCA CCACCACAAG AACACGGGCA
 401 ACATTGATAA GGACGAGATC TTTTACCCGC ACCGGTCGGT CAAGGACCTC
 451 CAGGACGTGC GCCAATGGGT CTACACGCTC GGCGGTGCGT GGTTTGTCTA
 501 CTTGAAGGTC GGGTATGCCC CGCGCACGAT GAGCCACTTT GACCCGTGGG
 551 ACCCGCTCCT CCTTCGCCGC GCGTCGGCCG TCATCGTGTC GCTCGGCGTC
 601 TGGGCCGCCT TCTTCGCCGC GTACGCGTAC CTCACATACT CGCTCGGCTT
 651 TGCCGTCATG GGCCTCTACT ACTATGCGCC GCTCTTTGTC TTTGCTTCGT
 701 TCCTCGTCAT TACGACCTTC TTGCACCACA ACGACGAAGC GACGCCGTGG
 751 TACGGCGACT CGGAGTGGAC GTACGTCAAG GCAACCTCT CGAGCGTCGA
 801 CCGCTCGTAC. GGCGCGTTCG TGGACAACCT GAGCCACCAC ATTGGCACGC
 851 ACCAGGTCCA CCACTTGTTC CCGATCATTC CGCACTACAA GCTCAACGAA
 901 GCCACCAAGC ACTTTGCGGC CGCGTACCCG CACCTCGTGC GCAGGAACGA
 951 CGAGCCCATC ATCACGGCCT TCTTCAAGAC CGCGCACCTC TTTGTCAACT
1001 ACGGCGCTGT GCCCGAGACG GCGCAGATCT TCACGCTCAA AGAGTCGGCC
1051 GCGGCCGCCA AGGCCAAGTC GGACTAA
```

FIG.9B

Sequence ID 26
        1 MTEDKTKVEF PTLTELKHSI PNACFESNLG LSLYYTARAI FNASASAALL

51 YAARSTPFIA DNVLLHALVC ATYIYVQGVI FWGFFTVGHD CGHSAFSRYH

101 SVNFIIGCIM HSAILTPFES WRVTHRHHHK NTGNIDKDEI FYPHRSVKDL

151 QDVRQWVYTL GGAWFVYLKV GYAPRTMSHF DPWDPLLLRR ASAVIVSLGV

201 WAAFFAAYAY LTYSLGFAVM GLYYYAPLFV FASFLVITTF LHHNDEATPW

251 YGDSEWTYVK GNLSSVDRSY GAFVDNLSHH IGTHQVHHLF PIIPHYKLNE

301 ATKHFAAAYP HLVRRNDEPI ITAFFKTAHL FVNYGAVPET AQIFTLKESA

351 AAAKAKSD*

Sequence ID 27
        1 ATGGCCCCGC AGACGGAGCT CCGCCAGCGC CACGCCGCCG TCGCCGAGAC
       51 GCCGGTGGCC GGCAAGAAGG CCTTTACATG CAGGAGGTC GCGCAGCACA
      101 ACACGGCGGC CTCGGCCTGG ATCATTATCC GCGGCAAGGT CTACGACGTG
      151 ACCGAGTGGG CCAACAAGCA CCCCGGCGGC CGCGAGATGG TGCTGCTGCA
      201 CGCCGGTCGC GAGGCCACCG ACACGTTCGA CTCGTACCAC CCGTTCAGCG
      251 ACAAGGCCGA GTCGATCTTG AACAAGTATG AGATTGGCAC GTTCACGGGC
      301 CCGTCCGAGT TTCCGACCTT CAAGCCGGAC ACGGGCTTCT ACAAGGAGTG
      351 CCGCAAGCGC GTTGGCGAGT ACTTCAAGAA GAACAACCTC CATCCGCAGG
      401 ACGGCTTCCC GGGCCTCTGG CGCATGATGG TCGTGTTTGC GGTCGCCGGC
      451 CTCGCCTTGT ACGGCATGCA CTTTTCGACT ATCTTTGCGC TGCAGCTCGC
      501 GGCCGCGGCG CTCTTTGGCG TCTGCCAGGC GCTGCCGCTG CTCCACGTCA
      551 TGCACGACTC GTCGCACGCG TCGTACACCA ACATGCCGTT CTTCCATTAC
      601 GTCGTCGGCC GCTTTGCCAT GGACTGGTTT GCCGGCGGCT CGATGGTGTC
      651 ATGGCTCAAC CAGCACGTCG TGGGCCACCA CATCTACACG AACGTCGCGG
      701 GCTCGGACCC GGATCTTCCG GTCAACATGG ACGGCGACAT CCGCCGCATC
      751 GTGAACCGCC AGGTGTTCCA GCCCATGTAC GCATTCCAGC ACATCTACCT
      801 TCCGCCGCTC TATGGCGTGC TTGGCCTCAA GTTCCGCATC CAGGACTTCA
      851 CCGACACGTT CGGCTCGCAC ACGAACGGCC GATCCGCGT CAACCCGCAC
      901 GCGCTCTCGA CGTGGATGGC CATGATCAGC TCCAAGTCGT TCTGGGCCTT
      951 CTACCGCGTG TACCTTCCGC TTGCCGTGCT CCAGATGCCC ATCAAGACGT
     1001 ACCTTGCGAT CTTCTTCCTC GCCGAGTTTG TCACGGGCTG GTACCTCGCG
     1051 TTCAACTTCC AAGTAAGCCA TGTCTCGACC GAGTGCGGCT ACCCATGCGG
     1101 CGACGAGGCC AAGATGGCGC TCCAGGACGA GTGGGCAGTC TCGCAGGTCA
     1151 AGACGTCGGT CGACTACGCC CATGGCTCGT GGATGACGAC GTTCCTTGCC
     1201 GGCGCGCTCA ACTACCAGGT CGTGCACCAC TTGTTCCCCA GCGTGTCGCA
     1251 GTACCACTAC CCGGCGATCG CGCCCATCAT CGTCGACGTC TGCAAGGAGT
     1301 ACAACATCAA GTACGCCATC TTGCCGGACT TTACGGCGGC GTTCGTTGCC
     1351 CACTTGAAGC ACCTCCGCAA CATGGGCCAG CAGGGCATCG CCGCCACGAT
     1401 CCACATGGGC TAA

FIG.9C

Sequence ID 28
```
  1  ATGGCAAACA GCAGCGTGTG GGATGATGTG GTGGGCCGCG TGGAGACCGG
 51  CGTGGACCAG TGGATGGATG GCGCCAAGCC GTACGCACTC ACCGATGGGC
101  TCCCGATGAT GGACGTGTCC ACCATGCTGG CATTCGAGGT GGGATACATG
151  GCCATGCTGC TCTTCGGCAT CCCGATCATG AAGCAGATGG AGAAGCCTTT
201  TGAGCTCAAG ACCATCAAGC TCTTGCACAA CTTGTTTCTC TTCGGACTTT
251  CCTTGTACAT GTGCGTGGAG ACCATCCGCC AGGCTATCCT CGGAGGCTAC
301  AAAGTGTTTG GAAACGACAT GGAGAAGGGC AACGAGTCTC ATGCTCAGGG
351  CATGTCTCGC ATCGTGTACG TGTTCTGCGT GTCCAAGGCA TACGAGTTCT
401  TGGATACCGC CATCATGATC CTTTGCAAGA AGTTCAACCA GGTTTCCTTC
451  TTGCATGTGT ACCACCATGC CACCATTTTT GCCATCTGGT GGCTATCGC
501  CAAGTACGCT CCAGGAGGTG ATGCGTACTT TTCAGTGATC CTCAACTCTT
551  TCGTGCACAC CGTCATGTAC GCATACTACT TCTTCTCCTC CCAAGGGTTC
601  GGGTTCGTGA AGCCAATCAA GCCGTACATC ACCACCCTTC AGATGACCCA
651  GTTCATGGCA ATGCTTGTGC AGTCCTTGTA CGACTACCTC TTCCCATGCG
701  ACTACCCACA GGCTCTTGTG CAGCTTCTTG GAGTGTACAT GATCACCTTG
751  CTTGCCCTCT TCGGCAACTT TTTTGTGCAG AGCTATCTTA AAAAGCCAAA
801  AAAGAGCAAG ACCAACTAA
```

Sequence ID 29
```
  1  MTVGFDETVT MDTVRNHNMP DDAWCAIHGT VYDITKFSKV HPGGDIIMLA
 51  AGKEATILFE TYHIKGVPDA VLRKYKVGKL PQGKKGETSH MPTGLDSASY
101  YSWDSEFYRV LRERVAKKLA EPGLMQRARM ELWAKAIFLL AGFWGSLYAM
151  CVLDPHGGAM VAAVTLGVFA AFVGTCIQHD GSHGAFSKSR FMNKAAGWTL
201  DMIGASAMTW EMQHVLGHHP YTNLIEMENG LAKVKGADVD PKKVDQESDP
251  DVFSTYPMLR LHPWHRQRFY HKFQHLYAPL IFGFMTINKV ISQDVGVVLR
301  KRLFQIDANC RYGSPWNVAR FWIMKLLTTL YMVALPMYMQ GPAQGLKLFF
351  MAHFTCGEVL ATMFIVNHII EGVSYASKDA VKGVMAPPRT VHGVTPMQVT
401  QKALSAAEST KSDADKTTMI PLNDWAAVQC QTSVNWAVGS WFWNHFSGGL
451  NHQIEHHCFP QNPHTVNVYI SGIVKETCEE YGVPYQAEIS LFSAYFKMLS
501  HLRTLGNEDL TAWST*
```

Sequence ID 30
5'-CCG SAG TTC ACS ATC AAG GAG ATC CGC GAS KSC ATC CCG GCC CAC TGC TTC -3'

Sequence ID 31
5'-GRS CTT CTT GAK GTG GWM SGT GGC CTC CTC GGC GTG GTA GWR CGG CAT-3'

Sequence ID 32
5'-CCS STC TAC TGG GCC TGC CAG GGT RTC GTC CTC ACS GGT GTC TGG-3'

FIG.9D

Sequence ID 33
5'-CCS STC TAC TGG ATC RYS CAG GGT RTC GTC KGY ACS GGT GTC TGG-3'

Sequence ID 34
5'-GGC GTG GTA GTG CGG CAT SMM CGA GAA GAR GTG GTG GGC GAC GTG-3'

Sequence ID 35
5'-CAC GTA CCT CCA GCA CAC GGA CAC CTA CG-3'

Sequence ID 36
5'- GAT CGA CAG CGC GAT CCA CCA CAT TGC-3'

Sequence ID 37
5'- CAA ATG GTA AAA GCT AGT GGC AGC GCT GC-3'

Sequence ID 38
5'-AGT ACG TGC CCT GGA CGA ACC AGT AGA TG-3'

Sequence ID 39
5'- TCA ACA GAA TTC ATG TGC AAA GGT CAA GCT CCT TCC AAG GCC GAC GTG -3'

Sequence ID 40
5'- AAA AGA AAG CTT TTA CTT TTC CTC GAG CTT GCG CTT GTA AAA CAC AAC-3'

Sequence ID 41
```
   1 ATGTGCAAAG GTCAAGCTCC TTCCAAGGCC GACGTGTTCC ACGCTGCGGG
  51 GTACCGCCCG GTCGCCGGCA CGCCCGAGCC GCTGCCGCTG GAGCCCCCGA
 101 CGATCACGCT CAAGGACCTG CGCGCGGCGA TCCCGGCCCA CTGCTTTGAG
 151 CGCAGCGCTG CCACTAGCTT TTACCATTTG GCCAAGAACC TTGCGATCTG
 201 CGCCGGCGTG TTCGCCGTTG GCCTCAAGCT CGCGGCTGCC GACTTGCCGC
 251 TCGCGGCCAA GCTGGTCGCG TGGCCCATCT ACTGGTTCGT CCAGGGCACG
 301 TACTTTACGG GCATCTGGGT CATTGCGCAC GAATGCGGCC ACCAGGCGTT
 351 CTCGGCGTCC GAGATCCTCA ACGACACGGT CGGTATCATT CTTCACTCGC
 401 TCCTCTTTGT GCCGTACCAC AGCTGGAAGA TCACGCACCG CCGCCACCAC
 451 TCCAACACGG GCAGCTGCGA GAACGACGAG GTGTTTACGC CGACGCCGCG
 501 GTCCGTCGTC GAGGCCAAGC ACGACCACTC GCTCCTCGAA GAGAGCCCGC
 551 TCTACAACCT GTACGGCATC GTCATGATGC TTCTCGTGGG CTGGATGCCG
 601 GGCTACCTCT TCTTCAACGC GACCGGCCCG ACCAAGTACG CTGGCCTCGC
 651 CAAGTCGCAC TTCAACCCGT ACGCAGCCTT TTTCCTCCCA AAGGAGCGCC
 701 TCAGCATCTG GTGGAGCGAC CTCTGCTTCC TCGCGGCCTT GTACGGCTTT
 751 GGCTACGGCG TCTCGGTCTT CGGCCTCCTC GATGTCGCCC GCCACTACAT
 801 CGTGCCGTAC CTCATTTGCA ACGCGTACCT CGTGCTCATC ACGTACCTCC
 851 AGCACACGGA TACGTACGTG CCCCACTTCC GCGGCGACGA GTGGAACTGG
 901 CTGCGCGGCG CGCTCTGCAC CGTCGACCGC TCGTTCGGCG CGTGGATCGA
 951 CAGCGCGATC CACCACATTG CCGACACGCA CGTGACGCAC CACATTTTCT
1001 CCAAGACGCC CTTCTACCAC GCGATCGAGG CGACCGACGC CATCACGCCC
1051 CTCCTCGGCA AGTACTACCT CATCGACCCG ACGCCGATCC CGCTGGCGCT
1101 CTGGCGCTCG TTCACGCACT GCAAGTACGT CGAGGACGAC GGCAACGTTG
1151 TGTTTTACAA GCGCAAGCTC GAGGAAAAGT AA
```

FIG.9E

Sequence ID 42
```
  1  MCKGQAPSKA DVFHAAGYRP VAGTPEPLPL EPPTITLKDL RAAIPAHCFE
 51  RSAATSFYHL AKNLAICAGV FAVGLKLAAA DLPLAAKLVA WPIYWFVQGT
101  YFTGIWVIAH ECGHQAFSAS EILNDTVGII LHSLLFVPYH SWKITHRRHH
151  SNTGSCENDE VFTPTPRSVV EAKHDHSLLE ESPLYNLYGI VMHLLVGWMP
201  GYLFFNATGP TKYAGLAKSH FNPYAAFFLP KERLSIWWSD LCFLAALYGF
251  GYGVSVFGLL DVARHYIVPY LICNAYLVLI TYLQHTDTYV PHFRGDEWNW
301  LRGALCTVDR SFGAWIDSAI HHIADTHVTH HIFSKTPFYH AIEATDAITP
351  LLGKYYLIDP TPIPLALWRS FTHCKYVEDD GNVVFYKRKL EEK*
```

FIG. 9F

DESATURASE GENES, ENZYMES ENCODED THEREBY, AND USES THEREOF

The subject application is a continuation of U.S. patent application Ser. No. 11/621,446 filed on Jan. 9, 2007, which has issued as U.S. Pat. No. 7,723,503, and which is a divisional of U.S. patent application Ser. No. 10/060,793 filed on Jan. 30, 2002, which issued as U.S. Pat. No. 7,211,656, all of which are hereby incorporated in their entirety by reference.

FIELD OF THE INVENTION

The present invention is directed to the identification and isolation of novel genes that encode enzymes involved in the synthesis of polyunsaturated fatty acids (PUFAs). The invention is also directed to the novel desaturase enzymes encoded by these genes and to methods of utilizing the genes and/or the enzymes encoded by the genes genes. In particular, the invention is directed to genes derived from the fungus *Saprolegnia diclina* (ATCC 56851) that encode a novel (ω3-desaturase (also referred to herein as a Δ17-desaturase) and a novel Δ12-desaturase. These enzymes catalyze the introduction of a carbon-carbon double bond between a particular position within a fatty acid substrate. For example, the novel ω3-desaturase disclosed herein catalyzes the conversion of arachidonic acid (20:4n-6) to eicosapentaenoic acid (20:5n-3) (as well as other desaturation reactions involving other substrates). Likewise, the novel Δ12-desaturase disclosed herein catalyzes the conversion of oleic acid (18:1n-9) to linoleic acid (18:2n-6). The PUFAs so formed may be added to pharmaceutical compositions, nutritional compositions, animal feeds, or other products.

BACKGROUND

Desaturases are a class of enzymes critical in the production of long-chain polyunsaturated fatty acids. Polyunsaturated fatty acids (PUFAs) play many roles in the proper functioning of all life forms. For example, PUFAs are important components of the plasma membrane of a cell, where they are found in the form of phospholipids. PUFAs also are precursors to mammalian prostacyclins, eicosanoids, leukotrienes and prostaglandins. Additionally, PUFAs are necessary for the proper development of the infant brain, as well as for tissue formation and repair in mature mammals. In view of the biological significance of PUFAs, attempts are being made to produce them in an efficient manner.

A number of enzymes, most notably desaturases and elongases, are involved in PUFA biosynthesis (see FIG. 1). Elongases catalyze the addition of a 2-carbon unit to a fatty acid substrate. Thus, for example, an elongase (generically designated "elo" in FIG. 1) catalyzes the conversion of γ-linolenic acid (18:3n-6) to dihomo-γ-linolenic acid (20:3n-6), as well as the conversion of stearidonic acid (18:4n-3) to eicosatetraenoic acid (20:4n-3), etc.

Desaturases catalyze the introduction of unsaturations (i.e., double bonds) between carbon atoms within the fatty acid alkyl chain of the substrate. Thus, for example, linoleic acid (18:2n-6) is produced from oleic acid (18:1n-9) by the action of a Δ12-desaturase. Similarly, γ-linolenic acid (18:3n-6) is produced from linoleic acid by the action of a Δ6-desaturase.

Throughout the present application, PUFAs will be unambiguously identified using the "omega" system of nomenclature favored by physiologists and biochemists, as opposed to the "delta" system or I.U.P.A.C. system normally favored by chemists. In the "omega" system, a PUFA is identified by a numeric designation of the number of carbons in the chain. This is followed by a colon and then another numeric designation of the number of unsaturations in the molecule. This is then followed by the designation "n-x," where x is the number of carbons from the methyl end of the molecule where the first unsaturation is located. Each subsequence unsaturation (where there is more than one double bond) is located 3 addition carbon atoms toward the carboxyl end of the molecule. Thus, the PUFAs described herein can be described as being "methylene-interrupted" PUFAs. Where some other designation is required, deviations from the "omega" system will be noted.

Where appropriate, the action of the desaturase enzymes described herein will also be identified using the "omega" system. Thus, an "omega-3" desaturase catalyzes the introduction of a double bond between the two carbons at positions 3 and 4 from the methyl end of the substrate. However, in many instances, it is more convenient to indicate the activity of a desaturase by counting from the carboxyl end of the substrate. Thus, as shown in FIG. 1, a Δ9-desaturase catalyzes the introduction of a double bond between the two carbons at positions 9 and 10 from the carboxyl end of the substrate. In short, where the term "omega" is used, the position on the substrate is being designated relative to the methyl terminus; where the term "delta" is used, the position on the substrate is being designated relative to the carboxyl terminus.

It must be noted that mammals cannot desaturate fatty acid substrates beyond the Δ9 position (i.e., beyond 9 carbon atoms distant from the carboxyl terminus). Thus, for example, mammals cannot convert oleic acid (18:1n-9) into linoleic acid (18:2n-6); linoleic acid contains an unsaturation at position Δ12. Likewise, α-linolenic acid (18:3n-3) (having unsaturations at Δ12 and Δ15) cannot be synthesized by mammals. However, for example, mammals can convert α-linolenic acid into stearidonic acid (18:4n-3) by the action of a Δ6-desaturase. (See FIG. 1. See also PCT publication WO 96/13591; *The FASEB Journal*, Abstracts, Part I, Abstract 3093, page Δ532 (Experimental Biology 98, San Francisco, Calif., Apr. 18-22, 1998); and U.S. Pat. No. 5,552,306.)

Still referring to FIG. 1, in mammals, fungi, and algae, the stearidonic acid so formed is converted into eicosatetraenoic acid (20:4n-3) by the action of an elongase. This PUFA can then be converted to eicosapentaenoic acid (20:5n-3) by a Δ5-desaturase. Eicosapentaenoic acid can then, in turn, be converted to ω3-docosapentaenoic acid (22:5n-3) by an elongase.

Other eukaryotes, including fungi and plants, have enzymes that desaturate fatty acid substrates at carbon Δ12 (see PCT publication WO 94/11516 and U.S. Pat. No. 5,443,974) and at carbon delta-15 (see PCT publication WO 93/11245). The major polyunsaturated fatty acids of animals therefore are either derived from diet and/or from desaturation and elongation of linoleic acid or α-linolenic acid. In view of these difficulties, there remains a significant need to isolate genes involved in PUFA synthesis. Ideally, these genes would originate from species that naturally produce fatty acids that are not produced naturally in mammals. These genes could then be expressed in a microbial, plant, or animal system, which would thereby be altered to produce commercial quantities of one or more PUFAs. Thus, there is a definite need for novel Δ12- and Δ17-desaturase enzymes, the respective genes encoding these enzymes, as well as recombinant methods of producing these enzymes. Additionally, a need exists for oils containing levels of PUFAs beyond those naturally present. Access to such Δ12- and Δ17-desaturase enzymes allows for the production of large amounts of PUFAs that cannot be synthesized de novo in mammals. These PUFAs can be used as pharmaceutical agents and/or nutritional supplements.

All patents, patent publications and priority documents cited herein are hereby incorporated by reference in their entirety.

SUMMARY OF THE INVENTION

One embodiment of the present invention encompasses an isolated nucleotide acid sequence or fragment thereof comprising or complementary to a nucleotide sequence encoding a polypeptide having desaturase activity, wherein the amino acid sequence of the polypeptide has at least 50% sequence identity to an amino acid sequence selected from the group consisting of SEQ ID NO:26 and SEQ ID NO:42.

The present invention also includes an isolated nucleotide sequence (or fragment thereof) comprising or complementary to at least 50% of the nucleotide sequence selected from the group consisting of SEQ ID NO:25 and SEQ ID NO:41. In particular, the sequence may be selected from the group consisting of SEQ ID NO:25 and SEQ ID NO:41. The sequence may encode a functionally active desaturase which utilizes a polyunsaturated fatty acid as a substrate. Furthermore, the nucleotide sequence may be isolated from a fungus, such as *Saprolegnia diclina*.

An additional embodiment of the present invention includes a purified polypeptide encoded by the nucleotide sequences described above.

The present invention also includes a purified polypeptide that desaturates a polyunsaturated fatty acid substrate at an omega-3 carbon of the substrate and has at least 50% amino acid identity to an amino acid sequence comprising SEQ ID NO: 26. The polypeptide may desaturate a fatty acid substrate having 20 carbon atoms.

Additionally, the present invention encompasses a purified polypeptide that desaturates a polyunsaturated fatty acid substrate at a delta-12 carbon of the substrate and has at least 50% amino acid identity to SEQ ID NO: 42. The polypeptide may desaturate a fatty acid substrate having 18 carbon atoms.

Another embodiment of the present invention includes a method of producing a desaturase comprising the steps of: isolating a nucleotide sequence comprising or complementary to at least 50% of the nucleotide sequence selected from the group consisting of SEQ ID NO: 25 and SEQ ID NO: 41; constructing a vector comprising the isolated nucleotide sequence; and introducing the vector into a host cell for a time and under conditions sufficient for expression of a desaturase encoded by the isolated nucleotide sequence.

A further embodiment of the present invention includes a vector comprising: 1) an isolated nucleotide sequence corresponding to or complementary to at least about 50% of the nucleotide sequence selected from the group consisting of SEQ ID NO: 25 and SEQ ID NO: 41, operably linked to b) a regulatory sequence.

Additionally, another embodiment of the present invention includes a host cell comprising the above vector. The host cell may be, for example, a eukaryotic cell selected from the group consisting of a mammalian cell, an insect cell, a plant cell and a fungal cell. With respect to the host cell, expression of the isolated nucleotide sequence of the vector may result in the host cell producing a polyunsaturated fatty acid that is not produced in a wild-type of the host cell.

Also, the present invention encompasses a plant cell, plant, or plant tissue comprising the vector described above, wherein expression of the nucleotide sequence of the vector results in production of a polyunsaturated fatty acid by the plant cell, plant or plant tissue. The vector in the plant cell, plant or plant tissue may induce the production of a polyunsaturated fatty acid selected from the group consisting of, for example, linoleic acid, eicosatetraenoic acid and eicosapentaenoic acid. Also, the invention includes one or more plant oils or acids expressed by the plant cell, plant or plant tissue.

The invention also includes a transgenic plant comprising the above-described vector, wherein expression of the nucleotide sequence of the vector results in production of a polyunsaturated fatty acid in seeds of the transgenic plant.

Another embodiment of the present invention encompasses a method for producing a polyunsaturated fatty acid comprising the steps of: isolating a nucleotide sequence comprising or complementary to at least about 50% of the nucleotide sequence selected from the group consisting of SEQ ID NO: 25 and SEQ ID NO: 41; constructing a vector comprising the isolated nucleotide sequence; transforming the vector into a host cell for a time and under conditions sufficient for expression of a desaturase encoded by the isolated nucleotide sequence; and exposing the expressed desaturase selected from the group consisting of an omega-3-desaturase and a delta 12-desaturase, to a fatty acid substrate, whereby the substrate is catalytically converted by said desaturase into a desired polyunsaturated fatty acid product. The substrate is dihomo-gamma-linolenic acid or arachidonic acid and the product polyunsaturated fatty acid is eicosatetraenoic acid or eicosapentaenoic acid, respectively, when the expressed desaturase is an omega-3-desaturase. The substrate polyunsaturated fatty acid is oleic acid and the product polyunsaturated fatty acid is linoleic acid, when the expressed desaturase is a delta 12-desaturase.

The method may further comprise the step of exposing the polyunsaturated fatty acid product to one or more enzymes selected from the group consisting of a desaturase and an elongase, whereby the polyunsaturated fatty acid product is catalytically converted into another polyunsaturated fatty acid product. The product polyunsaturated fatty acid is eicosatetraenoic acid or eicosapentaenoic acid and the another polyunsaturated fatty acid is eicosapentaenoic acid or omega 3-docosapentaenoic acid, respectively, when the expressed desaturase is an omega 3-desaturase. The product polyunsaturated fatty acid is linoleic acid and the another polyunsaturated fatty acid is gamma-linolenic acid, when the expressed desaturase is a delta 12-desaturase.

Additionally, the method described directly above may further comprise the step of exposing the another polyunsaturated fatty acid to one or more enzymes selected from the group consisting of a desaturase and an elongase in order to convert the another polyunsaturated fatty acid to a final polyunsaturated fatty acid. The final polyunsaturated fatty acid is selected from the group consisting of omega 3-docosapentaenoic acid and docosahexaenoic acid, when the expressed desaturase of step (d) is an omega 3-desaturase. In contrast, the final polyunsaturated fatty acid is selected from the group consisting of dihomo-gamma-linolenic acid, arachidonic acid, adrenic acid, omega 6-docosapentaenoic acid, eicosatetraenoic acid, stearidonic acid, eicosapentaenoic acid, omega 3-docosapentaenoic acid and docosahexaenoic acid, when the expressed desaturase is a delta 12-desaturase.

An additional embodiment of the present invention includes a method of producing a polyunsaturated fatty acid comprising exposing a fatty acid substrate to a polypeptide having at least 50% amino acid identity to an amino acid sequence selected from the group consisting of SEQ ID NO: 26 and SEQ ID NO: 42, whereby the fatty acid substrate is catalytically converted into the polyunsaturated fatty acid product. The fatty acid substrate is dihomo-gamma-linolenic acid or arachidonic acid and the product polyunsaturated fatty acid is eicosatetraenoic acid or eicosapentaenoic acid, respectively, when the polypeptide is an omega 3-desaturase. In contrast, the fatty acid substrate is oleic acid and the polyunsaturated fatty acid product is linoleic acid, when the polypeptide is a delta 12-desaturase.

A further embodiment of the present invention includes a composition comprising at least one polyunsaturated fatty acid selected from the group consisting of the "product" polyunsaturated fatty acid produced according to the method described above, the "another" polyunsaturated fatty acid produced according to the method described above, and the "final" polyunsaturated fatty acid produced according to the method described above. The product polyunsaturated fatty acid is eicosatetraenoic acid or eicosapentaenoic acid, when the expressed desaturase of is an omega 3-desaturase. In contrast, the product polyunsaturated fatty acid is linoleic acid, when the expressed desaturase is a delta 12-desaturase. The another polyunsaturated fatty acid is eicosapentaenoic acid or omega 3-docosapentaenoic acid, respectively, when the expressed desaturase is an omega 3-desaturase. However, the another polyunsaturated fatty acid is gamma-linolenic acid, when the expressed desaturase is a delta 12-desaturase. The final polyunsaturated fatty acid is selected from the group consisting of omega 3-docosapentaenoic acid and docosahexaenoic acid, when the expressed desaturase is an omega 3-desaturase. In contrast, the final polyunsaturated fatty acid is selected from the group consisting of dihomo-gamma-linolenic acid, arachidonic acid, adrenic acid, omega 6-docosapentaenoic acid, eicosatetraenoic acid, stearidonic acid, eicosapentaenoic acid, omega 3-docosapentaenoic acid and docosahexaenoic acid, when the expressed desaturase is a delta 12-desaturase.

A further embodiment of the present invention includes a method of preventing or treating a condition caused by insufficient intake of at least one polyunsaturated fatty acid comprising administering to the patient the above-described composition in an amount sufficient to effect the prevention or treatment.

BRIEF DESCRIPTION OF THE DRAWINGS

FIG. 2 is the nucleotide sequence of sdd17 (SEQ ID NO: 25), a gene derived from S. diclina (ATCC 56851) that encodes a novel ω3-fatty acid desaturase.

FIG. 3 is the amino acid sequence of the ω3-desaturase (SDD17) (SEQ ID NO: 26) encoded by the nucleotide sequence depicted in FIG. 2.

FIG. 4 is an amino acid sequence comparison between the SDD17 desaturase (SEQ ID NO: 43) depicted in FIG. 3 and a known Δ15-desaturase from Synechocystis sp. (SYCDESB) (SEQ ID NO: 44).

FIG. 5 is an amino acid sequence comparison between the SDD17 desaturase (SEQ ID NO: 45) depicted in FIG. 3 and a known Δ17-desaturase from C. elegans (CELEFAT) (SEQ ID NO: 46).

FIG. 6 is the nucleotide sequence of sdd12 (SEQ ID NO:41), a gene derived from S. diclina (ATCC 56851) that encodes a novel Δ12-fatty acid desaturase.

FIG. 7 is the amino acid sequence of the Δ12-desaturase (SDD12) (SEQ ID NO: 42) encoded by the nucleotide sequence depicted in FIG. 6.

FIG. 8 is an amino acid sequence comparison between the SDD12 desaturase (SEQ ID NO: 47) depicted in FIG. 7 and a known Δ12-desaturase from G. hirsutum (GHO6DES) (SEQ ID NO: 48).

FIG. 9 A-F lists the sequence identifiers used throughout the application as well as the corresponding amino acid or nucleotide sequence.

DETAILED DESCRIPTION OF THE INVENTION

Figure 1:
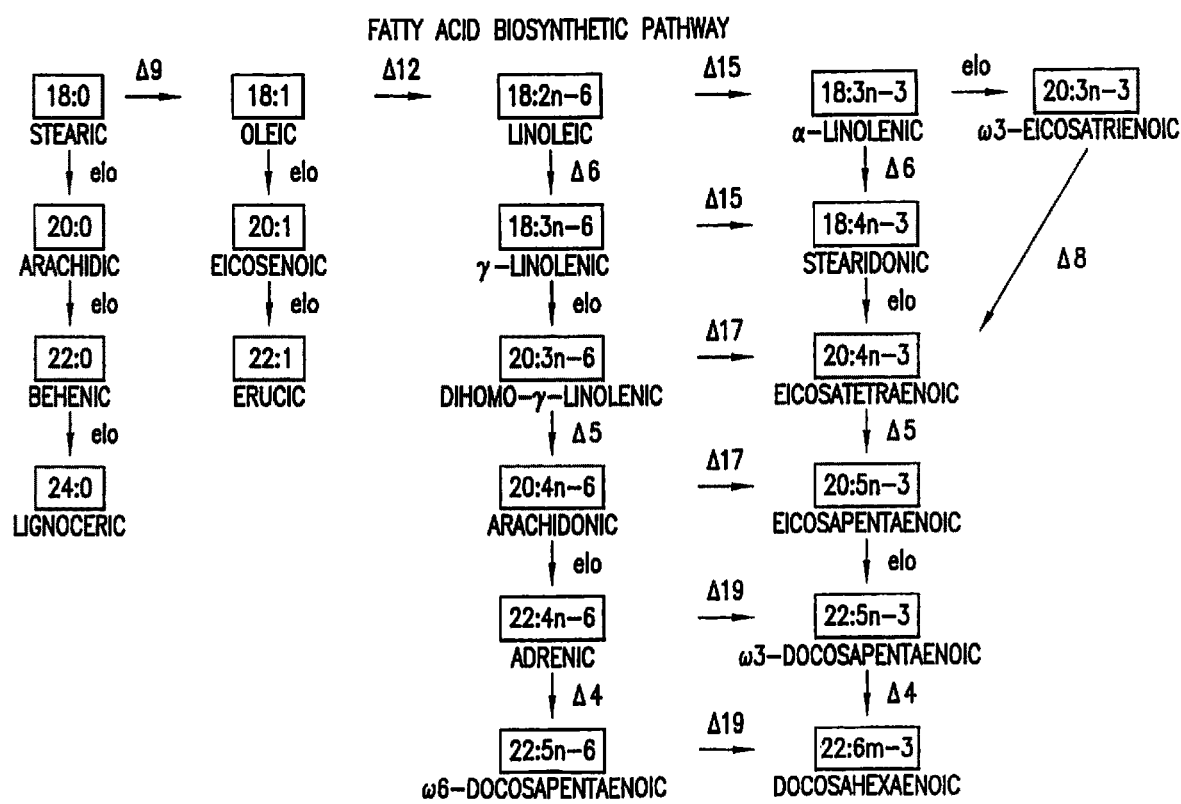
FIG. 1 is a schematic showing the biosynthetic pathway leading to the production of various PUFAs.

Abbreviations utilized herein:
18:1n-9=oleic acid=OA
18:2n-6=linoleic acid=LA
18:3n-6=gamma-linolenic acid=GLA
18:3n-3=alpha-linolenic acid=ALA
20:3n-6=stearidonic acid=STA
20:4n-6=dihomo-gamma-linolenic acid=DGLA
20:4n-3=arachidonic acid=AA
20:5n-3=eicosatetraenoic acid=ETA
20:5n-3=eicosapentaenoic acid=EPA
22:5n-3=adrenic acid
22:5n-3=omega-3-docosapentaenoic acid=DPA
22:6n-3=docosahexaenoic acid=DHA
PUFA=polyunsaturated fatty acid The subject invention relates to the nucleotide and translated amino acid sequences of the ω3-desaturase and Δ12-desaturase genes isolated from the fungus Saprolegnia diclina or S. diclina (ATCC 56851). Furthermore, the subject invention also includes uses of these genes and of the enzymes encoded by these genes. For example, the genes and their corresponding enzymes may be used in the production of polyunsaturated fatty acids such as linoleic acid, eicosapentaenoic acid, and the like. These fatty acids can be added to pharmaceutical compositions, nutritional compositions, and to other valuable products.

The fungus S. diclina (ATCC 56851), from which the polynucleotides described herein were isolated, is available commercially from the American Type Culture Collection, 10801 University Boulevard, Manassas, Va. 20110. The fungus is supplied frozen and can be propagated in ATCC medium 307 cornmeal agar (Difco #0386) at 24° C. For further information on this fungus, see Beakes G. (1983) "A comparative account of cyst coat ontogeny in saprophytic and fish-lesion (pathogenic) isolates of the Saprolegnia diclina-parasitica complex." Can. J. Bot. 61, 603-625; and Willoughby L. G., et al. (1983) "Zoospore germination of Saprolegnia pathogenic to fish." Trans. Br. Mycol. Soc. 80, 421-435.

The ω3-Desaturase Gene, the Δ12-Desaturase Gene, and the Enzymes Encoded Thereby The enzymes encoded by the omega-3 desaturase and delta-12 desaturase genes of the present invention are essential in the production of PUFAs having at least two unsaturations and an overall length of 18 carbons or longer. The nucleotide sequence of the isolated Saprolegnia diclina omega-3 desaturase gene is shown in SEQ ID NO: 25 and in FIG. 2. This gene differs significantly in sequence from all known desaturase genes, from any source. The encoded omega-3 desaturase enzyme is shown in SEQ ID NO: 26 and in FIG. 3. The nucleotide sequence of the isolated Saprolegnia diclina delta-12 desaturase gene is shown in SEQ ID NO: 41 and in FIG. 6. This gene also differs significantly in sequence from all known desaturase genes, from any source. The encoded delta-12 desaturase enzyme is shown in SEQ ID NO: 42 and in FIG. 7.

The isolated omega-3 desaturase gene of the present invention, when transformed into a yeast host, produces an omega-3 desaturase enzyme that readily catalyzes the conversion of DGLA to ETA, AA to EPA, and adrenic acid to DPA (see Example 5). In like manner, the isolated delta-12 desaturase gene of the present invention, when transformed into a yeast host, produces a delta-12 desaturase enzyme that readily catalyzes the conversion OA to LA (see Example 9).

It should be noted that the present invention also encompasses nucleotide sequences (and the corresponding encoded proteins) having sequences comprising, identical to, or complementary to at least about 50%, preferably at least about 60%, and more preferably at least about 70%, even more preferably at least about 80%, and most preferably at least about 90% of the nucleotides (i.e., having sequence identity to the sequence) shown in SEQ ID NO: 25 and SEQ ID NO: 41 (i.e., the nucleotide sequences of the omega-3 desaturase gene and the delta-12 desaturase gene of *Saprolegnia diclina*, respectively) described herein. (All integers between 50% and 100% are also considered to be within the scope of the present invention with respect to percent identity.) Such sequences may be derived from any source, either isolated from a natural source, or produced via a semi-synthetic route, or synthesized de novo. Such sequences may be isolated from or derived from fungal sources, as well as other non-fungal sources, such as bacterial, algal, *C. elegans*, mouse or human.

The present invention also encompasses fragments and derivatives of the nucleotide sequences shown in SEQ ID NO: 25 and SEQ ID NO: 41, as well as fragments and derivatives of the sequences derived from other sources, and having the above-described complementarity, identity or correspondence.

Functional equivalents of the above-sequences (i.e., sequences having omega-3 desaturase activity or delta-12 desaturase activity, as appropriate) are also encompassed by the present invention.

For purposes of the present invention, a "fragment" of a nucleotide sequence is defined as a contiguous sequence or approximately at least 6, preferably at least about 8, more preferably at least about 10 nucleotides, and even more preferably at least about 15 nucleotides corresponding to a region of the specified nucleotide sequence.

Sequence identity or percent identity is the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm may be extended to use with peptide or protein sequences using the scoring matrix created by Dayhoff, Atlas of Protein Sequences and Structure, M. O. Dayhoff ed., 5 Suppl. 3:353-358, National Biomedical Research Foundation, Washington, D.C., USA, and normalized by Gribskov, Nucl. Acids Res. 14(6):6745-66763 (1986). The Genetics Computer Group (GCG) (Madison, Wis.) provides a computer program that automates this algorithm for both nucleic acid and peptide sequences in the "BestFit" utility application. The default parameters for this method are described in the Wisconsin Sequence Analysis Package Program Manual, Version 8 (1995) (available from GCG). Other equally suitable programs for calculating the percent identity or similarity between sequences are generally known in the art.

The invention also includes a purified polypeptide which desaturates PUFAs at the omega-3 position and has at least about 50% amino acid similarity or identity, preferably at least about 60% similarity or identity, more preferably at least about 70% similarity or identity, even more preferably at least about 80% similarity or identity, and most preferably at least about 90% similarity or identity to the amino acid sequence shown in SEQ ID NO: 26 (FIG. 3) and encoded by the above-noted nucleotide sequence(s) (All integers between 50% and 100% similarity or identity are also included within the scope of the invention.)

The invention further includes a purified polypeptide which desaturates PUFAs at the delta-12 position and has at least about 50% amino acid similarity or identity, preferably at least about 60% similarity or identity, more preferably at least about 70% similarity or identity, even more preferably at least about 80% similarity or identity, and most preferably at least about 90% similarity or identity to the amino acid sequence shown in SEQ. ID. NO: 42 (FIG. 7) which, in turn, is encoded by the above-described nucleotide sequencers). (All integers between 50% and 100% similarity or identity are also included within the scope of the invention.)

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments. "Percentage of sequence identity" is calculated by comparing two optimally aligned sequences over a particular region, determining the number of positions at which the identical base occurs in both sequence in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912, 120.)

For purposes of the present invention, "complementarity is defined as the degree of relatedness between two DNA segments. It is determined by measuring the ability of the sense strand of one DNA segment to hybridize with the antisense strand of the other DNA segment, under appropriate conditions, to form a double helix. A "complement" is defined as a sequence which pairs to a given sequence based upon the canonic base-pairing rules. For example, a sequence A-G-T in one nucleotide strand is "complementary" to T-C-A in the other strand.

In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleotide sequence which encodes PUFA desaturase activity and that is hybridizable, under moderately stringent conditions, to a nucleic acid having a nucleotide sequence comprising or complementary to the nucleotide sequence comprising SEQ ID NO:25 or SEQ ID NO:41. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active enzyme, in the appropriate orientation relative to a plant promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

A "foreign" gene refers to a gene not normally found in the host organism, but that is introduced into the host organism by gene transfer. Foreign genes can comprise native genes inserted into a non-native organism, or chimeric constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1-82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is Transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular Processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature* (London) 327:70-73; U.S. Pat. No. 4,945,050), or an *Agrobacterium*-mediated method using an appropriate Ti plasmid containing the transgene (Ishida Y. et al., 1996, Nature Biotech. 14:745-750). The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al, *Cold Spring Harbor Symp. Quant. Biol.* 51:263-273 (1986); Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Expression of the Omega-3-Desaturase and the Delta 12-Desaturase Genes

Once the genes encoding the omega-3 and delta-12 desaturase enzymes have been isolated, they may then be introduced into either a prokaryotic or eukaryotic host cell (individually or in combination) through the use of a vector or construct. The vector, for example, a bacteriophage, cosmid or plasmid, may comprise the nucleotide sequence encoding either or both of the desaturase enzymes, as well as any promoter which is functional in the host cell and is able to elicit expression of the desaturase(s) encoded by the nucleotide sequence(s). The promoter is in operable association with, or operably linked, to the nucleotide sequence. (As noted above, a regulatory sequence (e.g., a promoter) is said to be "operably linked" with a coding sequence if the regulatory sequence affects transcription or expression of the coding sequence. The promoter (or other type of regulatory sequence) need not be directly linked to the coding sequence. Suitable promoters include, for example, those from genes encoding alcohol dehydrogenase, glyceraldehyde-3 phosphate dehydrogenase, phosphoglucoisomerase, phosphoglycerate kinase, acid phosphatase, T7, TPI, lactase, metallothionein, cytomegalovirus immediate early, whey acidic protein, glucoamylase, and promoters activated in the presence of galactose, for example, GAL1 and GAL10. Additionally, nucleotide sequences which encode other proteins, oligosaccharides, lipids, etc. may also be included within the vector as well as other regulatory sequences such as a polyadenylation signal (e.g., the poly-A signal of SV-40 T-antigen, ovalalbumin or bovine growth hormone), antibiotic resistance markers, auxotrophic markers, and the like. The choice of sequences present in the construct is dependent upon the desired expression products, the nature of the host cell, and the proposed means to separate transformed cells from non-transformed cells.

As noted above, once the vector has been constructed, it may then be introduced into the host cell of choice by methods known to those of ordinary skill in the art including, for example, transfection, transformation and electroporation (see *Molecular Cloning: A Laboratory Manual*, $2^{nd}$ ed., Vol. 1-3, ed. Sambrook et al., Cold Spring Harbor Laboratory Press (1989)). The host cell is then cultured under suitable conditions permitting expression of the genes leading to the production of the desired PUFA, which is then recovered and purified. (The substrates which may be produced by the host cell either naturally or transgenically, as well as the enzymes which may be encoded by DNA sequences present in the vector, which is subsequently introduced into the host cell, are shown in FIG. 1.)

Examples of suitable prokaryotic host cells include, for example, bacteria such as *Escherichia coli* and *Bacillus subtilis*, as well as cyanobacteria such as *Spirulina* spp. (i.e., blue-green algae). Examples of suitable eukaryotic host cells include, for example, mammalian cells, plant cells, yeast cells such as *Saccharomyces cerevisiae*, *Saccharomyces carlsbergensis*, *Lipomyces starkey*, *Candida* spp. such as *Yarrowia (Candida) lipolytica*, *Kluyveromyces* spp., *Pichia* spp., *Trichoderma* spp. or *Hansenula* spp., or fungal cells such as filamentous fungal cells, for example, *Aspergillus*, *Neurospora* and *Penicillium*. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate into the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introducing a construct that can integrate into the host genome or that autonomously replicates in the host cell. Stable expression of the gene of interest can be selected through the use of a selectable marker located on or co-transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the enzymes of the present invention, and thus ultimately produce the PUFA(s) of interest. More specifically, once the above-described construct is created, it may be inserted into the pronucleus of an embryo. The embryo may then be implanted into a recipient female. Alternatively, a nuclear transfer method can also be utilized (Schnieke et al., Science 278:2130-2133 (1997)). Gestation and birth are then permitted to occur (see, e.g., U.S. Pat. Nos. 5,750,176 and 5,700,671). Milk, tissue, or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene(s) encoding the desired desaturase enzyme(s) into their genomes. The mammal utilized as the host may be selected from the group consisting of, for example, mice, rats, rabbits, swine (porcines), goats and sheep (ovines), horses, and bovines. However, any mammal may be used provided it has the ability to incorporate DNA encoding the enzyme of interest into its genome.

For expression of a desaturase polypeptide, functional transcriptional and translational initiation and termination regions are operably linked to the DNA encoding the desaturase polypeptide of interest. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463,174; 4,943,674; 5,106,739; 5,175,095; 5,420,034; 5,188,958; and 5,589,379.

Alternatively, the expressed protein can be an enzyme that produces a product, and that product may be incorporated, either directly or upon further modifications, into a fluid fraction from the host plant. Expression of a desaturase gene, or antisense desaturase transcripts, can alter the levels of specific PUFAs, or derivatives thereof, found in plant parts and/or plant tissues. The desaturase polypeptide coding region may be expressed either by itself or with other genes, in order to produce tissues and/or plant parts containing higher proportions of desired PUFAs, or in which the PUFA composition more closely resembles that of human breast milk (Prieto et al., PCT publication WO 95/24494).

The termination region may be derived from the 3' region of the gene from which the initiation region was obtained or from a different gene. A large number of termination regions are known to be satisfactory in a variety of hosts from the same and different genera and species. The termination region usually is selected as a matter of convenience rather than because of any particular property.

As noted above, a plant (e.g., *Glycine max* (soybean) or *Brassica napus* (canola)) or plant tissue may also be utilized as a host or host cell, respectively, for expression of the desaturase enzymes, which may, in turn, be utilized in the production of PUFAs. More specifically, desired PUFAS can be expressed in seed. Methods of isolating seed oils are known in the art. Thus, in addition to providing a source for PUFAs, seed oil components may be manipulated through the expression of the desaturase genes, as well as perhaps other desaturase genes and elongase genes, to provide seed oils that can be added to nutritional compositions, pharmaceutical compositions, animal feeds and cosmetics. Once again, a vector that comprises a DNA sequence encoding the desaturase gene of interest, operably linked to a promoter, is introduced into the plant tissue or plant for a time and under conditions sufficient for expression of the desaturase gene. The vector may also comprise one or more genes that encode other enzymes, for example, delta-5-desaturase, elongase, delta-12-desaturase, delta-15-desaturase, delta-17-desaturase, and/or delta-19-desaturase enzymes. The plant tissue or plant may produce the relevant substrate (e.g., adrenic acid or DPA) upon which the enzyme acts or a vector encoding enzymes that produce such substrates may be introduced into the plant tissue, plant cell or plant. In addition, suitable substrates may be sprayed on plant tissues expressing the appropriate enzymes. Using these various techniques, one may produce PUFAs by use of a plant cell, plant tissue, or plant. It should also be noted that the invention also encompasses a transgenic plant comprising the above-described vector, wherein expression of the nucleotide sequence(s) of the vector results in production of a desired PUFA in, for example, the seeds of the transgenic plant.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. Nos. 5,004,863, 5,159,135, 5,518,908); soybean (U.S. Pat. Nos. 5,569,834, 5,416,011, McCabe et. al., Bio/Technology 6:923 (1988), Christou et al., Plant Physiol. 87:671-674 (1988)); *Brassica* (U.S. Pat. No. 5,463,174); peanut (Cheng et al., Plant Cell Rep. 15:653-657 (1996), McKently et al., Plant Cell Rep. 14:699-703 (1995)); papaya; and pea (Grant et al., Plant Cell Rep. 15:254-258, (1995)).

Transformation of monocotyledons using electroporation, particle bombardment, and *Agrobacterium* have also been reported. Transformation and plant regeneration have been achieved in asparagus (Bytebier et al., Proc. Natl. Acad. Sci. (USA) 84:5354, (1987)); barley (Wan and Lemaux, Plant Physiol 104:37 (1994)); *Zea mays* (Rhodes et al., Science 240:204 (1988), Gordon-Kamm et al., Plant Cell 2:603-618 (1990), Fromm et al., Bio/Technology 8:833 (1990), Koziel et al., Bio/Technology 11: 194, (1993), Armstrong et al., Crop Science 35:550-557 (1995)); oat (Somers et al., Bio/Technology 10: 15 89 (1992)); orchard grass (Horn et al., Plant Cell Rep. 7:469 (1988)); rice (Toriyama et al., TheorAppl. Genet. 205:34, (1986); Part et al., Plant Mol. Biol. 32:1135-1148, (1996); Abedinia et al., Aust. J. Plant Physiol. 24:133-141 (1997); Zhang and Wu, Theor. Appl. Genet. 76:835 (1988); Zhang et al. Plant Cell Rep. 7:379, (1988); Battraw and Hall, Plant Sci. 86:191-202 (1992); Christou et al., Bio/Technology 9:957 (1991)); rye (De la Pena et al., Nature 325:274 (1987)); sugarcane (Bower and Birch, Plant J. 2:409 (1992)); tall fescue (Wang et al., Bio/Technology 10:691 (1992)), and wheat (Vasil et al., Bio/Technology 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., Nature 335:454-457 (1988); Marcotte et al., Plant Cell 1:523-532 (1989); McCarty et al., Cell 66:895-905 (1991); Hattori et al., Genes Dev. 6:609-618 (1992); Goff et al., EMBO J. 9:2517-2522 (1990)).

Transient expression systems may be used to functionally dissect gene constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

In view of the above, the present invention encompasses a method of producing an omega-3 desaturase and/or a delta-12 desaturase enzyme, the method comprising the steps of: 1) isolating the nucleotide sequence of the gene encoding the desired desaturase enzyme(s); 2) constructing a vector comprising the nucleotide sequence(s); and 3) introducing the vector into a host cell for a time and under conditions sufficient for the production of the desaturase enzyme(s).

The present invention also encompasses a method of producing PUFAs, the method comprising exposing a suitable fatty acid substrate to the enzyme such that the desaturase converts the fatty acid substrate to a desired PUFA product. For example, when AA (20:4n-6) is exposed to the omega-3 desaturase enzyme of the present invention, it is converted into EPA (20:5n-3). The EPA so formed may be converted into DPA (22:5n-3) by the action of an elongase, and the DPA subsequently converted into DHA (22:6n-3) by a delta-4 desaturase.

Likewise, when OA (18:1n-9) is exposed to the delta-12 desaturase enzyme of the present invention, it is converted into LA (18:2n-6). The LA so formed may be converted into virtually all of the PUFAs shown in FIG. 1 by the subsequent actions of suitable desaturases and/or elongases.

Uses of the Subject Desaturase Genes and Enzymes Encode Thereby

As noted above, the isolated desaturase genes and the desaturase enzymes encoded thereby have many uses. For example, the genes and the corresponding enzymes may be used indirectly or directly, singly or in combination, in the production of PUFAs. For example, the omega-3 desaturase may be used in the production of ETA, EPA, DPA, DHA, and the like. As used in this context, the word "directly" encompasses the situation where the enzyme is used to catalyze the conversion of a fatty acid substrate directly into the desired fatty acid product, without any intermediate steps or pathway intermediates (e.g., the conversion of AA to EPA). The product so obtained is then utilized in a composition. "Indirectly" encompasses the situation where a desaturase according to the present invention is used to catalyze the conversion of a fatty acid substrate into another fatty acid (i.e., a pathway intermediate) by the desaturase (e.g., the conversion of AA to EPA) and then the latter fatty acid (the EPA) is converted to the desired fatty acid product by use of another desaturase or non-desaturase enzyme (e.g., the conversion of EPA to DPA by elongase). These PUFAs (i.e., those produced either directly or indirectly by the activity of the subject desaturases) may be added to, for example, nutritional compositions, pharmaceutical compositions, cosmetics, and animal feeds, all of which are encompassed by the present invention. Such uses are described in detail below.

Nutritional Compositions:

The present invention includes nutritional compositions. For purposes of the present invention, such compositions include any food or preparation for human consumption (including for enteral and/or parenteral consumption) which when taken into the body (a) serve to nourish or build up tissues or supply energy; and/or (b) maintain, restore or support adequate nutritional status or metabolic function.

The nutritional composition of the present invention comprises an oil, fatty acid ester, or fatty acid produced directly or indirectly by use of the desaturase genes disclosed herein. The composition may either be in a solid or liquid form. Additionally, the composition may include edible macronutrients, vitamins, and/or minerals in amounts desired for a particular use. The amounts of these ingredients will vary depending on whether the composition is intended for use with normal, healthy infants, children, or adults, or for use with individuals having specialized needs, such as individuals suffering from metabolic disorders and the like.

Examples of macronutrients that may be added to the compositions include (but are not limited to): edible fats, carbohydrates and proteins. Examples of such edible fats include (but are not limited to): coconut oil, borage oil, fungal oil, black current oil, soy oil, and mono- and diglycerides. Examples of such carbohydrates include (but are not limited to): glucose, edible lactose, and hydrolyzed search. Additionally, examples of proteins which may be utilized in the nutritional composition of the invention include (but are not limited to) soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of semi-purified or purified origin. By semi-purified or purified is meant a material which has been prepared by purification of a natural material or by de novo synthesis.

Examples of nutritional compositions of the present invention include (but are not limited to): infant formulas, dietary supplements, dietary substitutes, and rehydration compositions. Nutritional compositions of particular interest include (but are not limited to) compositions for enteral and parenteral supplementation for infants, specialized infant formulas, supplements for the elderly, and supplements for those with gastrointestinal difficulties and/or malabsorption.

The nutritional composition of the present invention may also be added to food even when supplementation of the diet is not required. For example, the composition may be added to food of any type, including (but not limited to): margarine, modified butter, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to PUFAs produced according to the present invention, macronutrients, vitamins, and/or minerals, as described previously. The macronutrients may be present in amounts equivalent to those present in human milk or on an energy basis, i.e., on a per calorie basis.

The enteral formula, for example, may be sterilized and subsequently utilized on a ready-to-feed (RTF) basis or stored in a concentrated liquid or powder. The powder can be prepared by spray-drying the formula prepared as indicated above, and reconstituting it by rehydrating the concentrate. Adult and pediatric nutritional formulas are known in the art and are commercially available (e.g., Similac®, Ensure®, Jevity® and Alimentum® from Ross Products Division, Abbott Laboratories, Columbus, Ohio). An oil or fatty acid produced in accordance with the present invention may be added to any of these formulas.

The energy density of the nutritional compositions of the present invention, when in liquid form, may range from about 0.6 kcal to about 3 kcal per ml. When in solid or powdered form, the nutritional supplements may contain from about 1.2 to more than 9 kcals per gram, preferably about 3 to 7 kcals per gm. In general, the osmolality of a liquid product should be less than 700 mOsm and, more preferably, less than 660 mOsm.

The nutritional formula may include macronutrients, vitamins, and minerals, as noted above, in addition to the PUFAs produced in accordance with the present invention. The presence of these additional components helps the individual ingest the minimum daily requirements of these elements. In addition to the provision of PUFAs, it may also be desirable to add zinc, copper, folic acid, and antioxidants to the composition. It is believed that these substances boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight percent of the carbohydrate is indigestible oligosaccharide. In a more preferred embodiment, the nutritional composition additionally comprises protein, taurine, and carnitine.

As noted above, the PUFAs produced in accordance with the present invention, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% DHA, from about 0.03% to about 0.13% EPA, from about 0.30% to about 0.88% AA, from about 0.22% to about 0.67% DGLA, and from about 0.27% to about 1.04% GLA. Thus, fatty acids such as AA, EPA and/or DHA produced in accordance with the present invention can be used to alter, for example, the composition of infant formulas in order to replicate more faithfully the PUFA content of human breast milk or to alter the presence of PUFAs normally found in a non-human mammal's milk. In particular, a composition for use a medicinal agent or food supplement, particularly a breast milk substitute or supplement, will preferably comprise one or more of AA, DGLA and GLA. More preferably, the composition will comprise from about 0.3 to 30% AA, from about 0.2 to 30% DGLA, and/or from about 0.2 to about 30% GLA.

Parenteral nutritional compositions comprising from about 2 to about 30% by weight fatty acids calculated as triglycerides are encompassed by the present invention. The preferred composition has about 1 to about 25% by weight of the total PUFA composition as GLA. Other vitamins, particularly fat-soluble vitamins such as vitamin A, D, E and L-carnitine, can optionally be included. When desired, a preservative such as alpha-tocopherol may be added in an amount of about 0.1% by weight.

In addition, the ratios of AA, DGLA and GLA can be adapted for a particular given end use. When formulated as a breast milk supplement or substitute, a composition which comprises one or more of AA, DGLA and GLA will be provided in a ratio of from about 1:19:30 to about 6:1:0.2, respectively. For example, the breast milk of animals can vary in ratios of AA:DGLA:GLA ranging from 1:19:30 to 6:1:0.2, which includes intermediate ratios which are preferably about 1:1:1, 1:2:1, 1:1:4. When produced together in a host cell, adjusting the rate and percent of conversion of a precursor substrate such as GLA and DGLA to AA can be used to control the PUFA ratios precisely. For example, a 5% to 10% conversion rate of DGLA to AA can be used to produce an AA to DGLA ratio of about 1:19, whereas a conversion rate of about 75% to 80% can be used to produce an AA to DGLA ratio of about 6:1. Therefore, whether in a cell culture system or in a host animal, regulating the timing, extent and specificity of desaturase expression, as well as the expression of other desaturases and elongases, can be used to modulate PUFA levels and ratios. The PUFAs produced in accordance with the present invention (e.g., AA, EPA, etc.) may then be combined with other PUFAs or other types of fatty acids in the desired concentrations and ratios.

Additionally, PUFAs produced in accordance with the present invention or host cells transformed to contain and express the subject desaturase genes may also be used as animal food supplements to alter an animal's tissue or milk fatty acid composition to one more desirable for human or animal consumption.

Pharmaceutical Compositions:

The present invention also encompasses a pharmaceutical composition comprising one or more of the acids and/or resulting oils produced using the desaturase genes, in accordance with the methods described herein. Specifically, such a pharmaceutical composition may comprise one or more of the PUFAs and/or oils, in combination with a standard, well-known, non-toxic pharmaceutically-acceptable carrier, adjuvant or vehicle such as phosphate-buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride, and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as ethoxylated isostearyl alcohols, polyoxyethylene sorbitol and sorbitan esters, microcrystalline cellulose, aluminum metahydroxide, bentonite, agar-agar, and tragacanth or mixtures of these substances.

Solid dosage forms such as tablets and capsules can be prepared using techniques well known in the art. For example, PUFAs produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present invention or derivatives thereof may be incorporated into commercial formulations such as Intralipids™. The typical normal adult plasma fatty acid profile comprises 6.64 to 9.46% AA, 1.45 to 3.11% DGLA, and 0.02 to 0.08% GLA. These PUFAs or their metabolic precursors can be administered alone or in combination with other PUFAs to achieve a normal fatty acid profile in a patient. Where desired, the individual components of the formulations may be provided individually, or in kit form, for single or multiple use. A typical dosage of a particular fatty acid is from 0.1 mg to 20 g, taken from one to five times per day (up to 100 g daily) and is preferably in the range of from about 10 mg to about 1, 2, 5, or 10 g daily (taken in one or multiple doses).

Possible routes of administration of the pharmaceutical compositions of the present invention include, for example, enteral (e.g., oral and rectal) and parenteral. For example, a liquid preparation may be administered orally or rectally. Additionally, a homogenous mixture can be completely dispersed in water, admixed under sterile conditions with physiologically acceptable diluents, preservatives, buffers or propellants to form a spray or inhalant.

The route of administration will, of course, depend upon the desired effect. For example, if the composition is being utilized to treat rough, dry, or aging skin, to treat injured or burned skin, or to treat skin or hair affected by a disease or condition, it may be applied topically.

The dosage of the composition to be administered to the patient may be determined by one of ordinary skill in the art and depends upon various factors such as weight of the patient, age of the patient, overall health of the patient, past history of the patient, immune status of the patient, etc.

With respect to form, the composition may be, for example, a solution, a dispersion, a suspension, an emulsion or a sterile powder that is then reconstituted.

The present invention also includes the treatment of various disorders by use of the pharmaceutical and/or nutritional compositions described herein. In particular, the compositions of the present invention may be used to treat restenosis after angioplasty. Furthermore, symptoms of inflammation, rheumatoid arthritis, asthma and psoriasis may also be treated with the compositions of the invention. Evidence also indicates that PUFAs may be involved in calcium metabolism; thus, the compositions of the present invention may be utilized in the treatment or prevention of osteoporosis and of kidney or urinary tract stones.

Additionally, the compositions of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes (see U.S. Pat. No. 4,826,877 and Horrobin et al., *Am. J. Clin. Nutr. Vol.* 57 (Suppl.) 732S-737S). Altered fatty acid metabolism and composition have been demonstrated in diabetic animals.

Furthermore, the compositions of the present invention, comprising PUFAs produced either directly or indirectly through the use of the desaturase enzymes, may also be used in the treatment of eczema and in the reduction of blood pressure. Additionally, the compositions of the present invention may be used to inhibit platelet aggregation, to induce vasodilation, to reduce cholesterol levels, to inhibit proliferation of vessel wall smooth muscle and fibrous tissue (Brenner et al., *Adv. Exp. Med. Biol. Vol.* 83, p. 85-101, 1976), to reduce or to prevent gastrointestinal bleeding and other side effects of non-steroidal anti-inflammatory drugs (see U.S. Pat. No. 4,666,701), to prevent or to treat endometriosis and premenstrual syndrome (see U.S. Pat. No. 4,758,592), and to treat myalgic encephalomyelitis and chronic fatigue after viral infections (see U.S. Pat. No. 5,116,871).

Further uses of the compositions of the present invention include use in the treatment of AIDS, multiple sclerosis, and inflammatory skin disorders, as well as for maintenance of general health.

Additionally, the composition of the present invention may be utilized for cosmetic purposes. It may be added to pre-existing cosmetic compositions such that a mixture is formed or a PUFA produced according to the subject invention may be used as the sole "active" ingredient in a cosmetic composition.

Veterinary Applications:

It should be noted that the above-described pharmaceutical and nutritional compositions may be utilized in connection with animals (i.e., domestic or non-domestic, including mammals, birds, reptiles, lizards, etc.), as well as humans, as animals experience many of the same needs and conditions as humans. For example, the oil or fatty acids of the present invention may be utilized in animal feed supplements, animal feed substitutes, animal vitamins or in animal topical ointments.

The present invention may be further illustrated by the non-limiting examples presented below:

EXAMPLE 1

Construction of *Saprolegnia diclina* (ATCC 56851) cDNA Library

To isolate genes encoding for functional desaturase enzymes, a cDNA library was constructed. *Saprolegnia* diclina cultures were grown in potato dextrose media (Difco #336, BD Diagnostic Systems, Sparks, Md.) at room temperature for four days with constant agitation. The mycelia were harvested by filtration through several layers of cheesecloth, and the cultures were crushed in liquid nitrogen using a mortar and pestle. The cell lysates were resuspended in RT buffer (Qiagen, Valencia, Calif.) containing β-mercaptoethanol and incubated at 55° C. for three minutes. These lysates were homogenized either by repeated aspirations through a syringe or over a "Qiashredder"-brand column (Qiagen). The total RNA was finally purified using the "RNeasy Maxi"-brand kit (Qiagen), as per the manufacturer's protocol.

mRNA was isolated from total RNA from each organism using an oligo dT cellulose resin. The "pBluescript II XR"-brand library construction kit (Stratagene, La Jolla, Calif.) was used to synthesize double-stranded cDNA. The double-stranded cDNA was then directionally cloned (5' EcoRI/3' XhoI) into pBluescript II SK(+) vector (Stratagene). The *S. diclina* library contained approximately $2.5 \times 10^6$ clones, each with an average insert size of approximately 700 bp. Genomic DNA of *S. diclina* was isolated by crushing the culture in liquid nitrogen followed by purification using the "Genomic DNA Extraction"-brand kit (Qiagen), as per the manufacturer's protocol.

EXAMPLE 2

Determination of Codon Usage in *Saprolegnia diclina*

The 5' ends of 350 random cDNA clones were sequenced from the *Saprolegnia diclina* cDNA library described in Example 1. The sequences were translated into six reading frames using GCG program (Genetics Computer Group, Madison, Wis.) with the "FastA"-brand algorithm to search for similarity between a query sequence and a group of sequences of the same type, specifically within the GenBank database. Many of the clones were identified as putative housekeeping genes based on protein homology to known genes. Eight *S. diclina* cDNA sequences were thus selected. Additionally, the full-length *S. diclina* delta 5-desaturase and delta 6-desaturase sequences were also used (see Table 1 below). These sequences were then used to generate the *S. diclina* codon bias table shown in Table 2 below by employing the "CodonFrequency" program from GCG.

TABLE 1

Genes from *Saprolegnia diclina* used for generation of Codon Bias Table

| Clone # | Match | # bases | # amino acids |
|---|---|---|---|
| 3 | Actin gene | 615 | 205 |
| 20 | Ribosomal protein L23 | 420 | 140 |
| 55 | Heat Shock protein 70 gene | 468 | 156 |
| 83 | Glyceraldehyde-3-P-dehydrogenase gene | 588 | 196 |
| 138 | Ribosomal protein S13 gene | 329 | 110 |
| 179 | Alpha-tubulin 3 gene | 591 | 197 |
| 190 | Casein kinase II alpha subunit gene | 627 | 209 |
| 250 | Cyclophilin gene | 489 | 163 |
|  | Delta 6-desaturase | 1362 | 453 |
|  | Delta 5-desaturase | 1413 | 471 |
|  | Total | 6573 | 2191 |

TABLE 2

Codon Bias Table for *Saprolegnia diclina*

| Amino acid | Codon Bias | % used |
|---|---|---|
| Ala | GCC | 55% |
| Arg | CGC | 50% |
| Asn | AAC | 94% |
| Asp | GAC | 85% |
| Cys | TGC | 77% |
| Gln | CAG | 90% |
| Glu | GAG | 80% |
| Gly | GGC | 67% |
| His | CAC | 86% |
| Ile | ATC | 82% |
| Leu | CTC | 52% |
| Lys | AAG | 87% |
| Met | ATG | 100% |
| Phe | TTC | 72% |
| Pro | CCG | 55% |
| Ser | TCG | 47% |
| Thr | ACG | 46% |
| Trp | TGG | 100% |
| Tyr | TAC | 90% |
| Val | GTC | 73% |
| Stop | TGA | 67% |

EXAMPLE 3

Design of Degenerate Oligonucleotides for the Isolation of an Desaturase from *Saprolegnia diclina* (ATCC 56851)

Fungi like *Saprolegnia diclina* produce a wide range of PUFAs, including arachidonic acid (AA) and eicosapentaenoic acid (EPA) via the PUFA biosynthetic pathway depicted in FIG. 1. Analysis of the fatty acid composition of *Saprolegnia diclina* (ATCC 56851) showed 15.42% of the total lipid to be AA and 12.2% of the total lipid to be EPA (see Table 5). Linoleic acid (LA) was the only other intermediate present in high amounts. This indicates that *S. diclina* has very active delta-6 and delta-5 desaturases, as well as elongases that shunt intermediates through the pathway depicted in FIG. 1. Due to the high percentage of EPA in this organism, an active omega-3 desaturase (synonymous with a "delta-15" desaturase when the substrate is a $C_{18}$ fatty acid, a "delta-17" desaturase when the substrate is a $C_{20}$ fatty acid, and a "delta-19" desaturase when the substrate is a $C_{22}$ fatty acid) is predicted to exist which is capable of converting AA (20:4n-6) to EPA (20:5n-3).

As just noted, omega-3 desaturases are enzymes that catalyze the introduction of a double bond at the delta-15 position for $C_{18}$-acyl chains, the delta-17 position for $C_{20}$-acyl chains, and the delta-19 position for $C_{22}$-acyl chains. There are several known omega-3 desaturases from plants, but these act exclusively on $C_{18}$ fatty acid substrates like LA (18:2n-6) and GLA (18:3n-6). These types of desaturases are collectively referred to as delta 15-desaturases. At this point in time, only one omega-3 desaturase gene has been isolated whose encoded enzyme catalyzes the desaturation of $C_{18}$, $C_{20}$, and $C_{22}$ fatty acid substrates. This is fat-1 from *C. elegans*. See U.S. Pat. No. 6,194,167, issued Feb. 27, 2001.

The approach used in this Example to identify an omega-3 desaturase from *S. diclina* involved PCR amplification of a region of the desaturase gene using degenerate oligonucleotides (primers) that contained conserved motifs present in other known omega-3 desaturases. Omega-3 desaturases from the following organisms were used for the design of these degenerate primers: *Arabidopsis thaliana* (Swissprot #

P46310), *Ricunus communis* (Swissprot # P48619), *Glycine max* (Swissprot # 48621), *Sesamum indicum* (Swissprot # P48620), *Nicotiana tabacum* (GenBank # D79979), *Perilla frutescens* (GenBank # U59477), *Capsicum annuum* (GenBank # AF222989), *Limnanthes douglassi* (GenBank # U17063), and *Caenorhabditis elegans* (GenBank # L41807). Some primers were designed to contain the conserved histidine-box motifs that are important components of the active site of the enzymes. See Shanklin, J. E., McDonough, V. M., and Martin, C. E. (1994) Biochemistry 33, 12787-12794.

Alignment of sequences was carried out using the CLUSTALW Multiple Sequence Alignment Program.

The following degenerate primers were designed and used in various combinations:

```
Protein Motif 1:
                                     (SEQ ID NO: 49)
NH3-TRAAIPKHCWVI-COOH Primer RO 1144 (Forward):
                                     (SEQ ID NO: 1)
5'-ATC CGC GCC GCC ATC CCC AAG CAC TGC TGG GTC

AAG-3'.

Protein Motif 2:
                                     (SEQ ID NO: 50)
NH3-ALFVLGHDCGHGSFS-COOH This primer contains the histidine-box 1

(underlined).

Primer RO 1119 (Forward):
                                     (SEQ. ID. NO: 2)
5'-GCC CTC TTC GTC CTC GGC CAY GAC TGC CCC CAY GGC

TCG TTC TCG-3'.

Primer RO 1118 (Reverse):
                                     (SEQ. ID. NO: 3)
5'-GAG RTG GTA RTG GGG GAT CTG GGG GAA GAR RTG RTG

GRY GAC RTG-3'.

Protein Motif 3:
                                     (SEQ ID NO: 51)
NH3-PYHGWRISHRTHHQN-COOH This primer contains the histidine-box 2

(underlined).

Primer RO 1121 (Forward):
                                     (SEQ. ID. NO: 4)
5'-CCC TAC CAY GGC TGG CGC ATC TCG CAY CGC ACC CAY

CAY CAG AAC-3'.

Primer RO 1122 (Reverse):
                                     (SEQ. ID. NO: 5)
5'-GTT CTG RTG RTG GGT CCG RTG CGA GAT GCG CCA GCC

RTG GTA GGG-3'.

Protein Motif 4:
                                     (SEQ ID NO: 52)
NH3-GSHF D/H P D/Y SDLFV-COOH Primer RO 1146 (Forward):
                                     (SEQ. ID. NO: 6)
5'-GGC TCG CAC TTC SAC CCC KAC TCG GAC CTC TTC

GTC-3'.

Primer RO 1147 (Reverse):
                                     (SEQ. ID. NO: 7)
5'-GAC GAA GAG GTC CGA GTM GGG GTW GAA GTG CGA

GCC-3'.

Protein Motif 5:
                                     (SEQ ID NO: 53)
NH3-WS Y/F L/V RGGLTT L/I DR-COOH Primer RO 1148 (Reverse):
                                     (SEQ. ID. NO: 8)
5'-GCG CTG GAK GGT GGT GAG GCC GCC GCG GAW GSA CGA

CCA-3'.

Protein Motif 6:
                                     (SEQ ID NO: 54)
NH3-HHDIGTHVIHHLFPQ-COOH This sequence contains the third histidine-box (underlined).

Primer RO 1114 (Reverse):
                                     (SEQ. ID. NO: 9)
5'-CTG GGG GAA GAG RTG RTG GAT GAC RTG GGT GCC GAT

GTC RTG RTG-3'.

Protein Motif 7:
                                     (SEQ ID NO: 55)
NH3-H L/F FP Q/K IPHYHL V/I EAT-COOH Primer RO 1116 (Reverse):
                                     (SEQ. ID. NO: 10)
5'-GGT GGC CTC GAY GAG RTG GTA RTG GGG GAT CTK GGG

GAA GAR RTG-3'.

Protein Motif 8:
                                     (SEQ ID NO: 56)
NH3-HV A/I HH L/F FPQIPHYHL-COOH
```

This primer contains the third histidine-box (underlined) and accounts for differences between the plant omege-3 desaturases and the *C. elegans* omega-3-desaturase.

```
Primer RO 1118 (Reverse):
                                     (SEQ. ID. NO: 11)
5'-GAG RTG GTA RTG GGG GAT CTG GGG GAA GAR RTG RTG

GRY GAC RTG-3'.
```

The degeneracy code used for SEQ. ID. NOS: 1 through 11 was as follows: R=A/G; Y=C/T; M=A/C; K=G/T; W=A/T; S=C/G; B=C/G/T; D=A/G/T; H=A/C/T; V=A/C/G; and N=A/C/G/T.

EXAMPLE 4

Identification and Isolation of an Omega-3 Desaturase Gene from *Saprolegnia diclina* (ATCC 56851)

Various sets of the degenerate primers disclosed in Example 3 were used in PCR amplification reactions, using as a template either the *S. diclina* cDNA library plasmid DNA (from Example 1), or *S. diclina* genomic DNA. Also various different DNA polymerases and reaction conditions were used for the PCR amplifications. These reactions variously involved using "Platinum Taq"-brand DNA polymerase (Life Technologies Inc., Rockville, Md.), or cDNA polymerase (Clonetech, Palo Alto, Calif.), or Taq PCR-mix (Qiagen), at differing annealing temperatures.

PCR amplification using the primers RO 1121 (Forward) (SEQ. ID. NO: 4) and RO 1116 (Reverse) (SEQ. ID. NO: 10) resulted in the successful amplification of a fragment homologous to a known omega-3 desaturase. The RO 1121 (Forward) primer corresponds to the protein motif 3; the RO 1116 (Reverse) primer corresponds to the protein motif 7.

PCR amplification was carried out in a 50 µl total volume containing: 3 µl of the cDNA library template, PCR buffer containing 40 mM Tricine-KOH (pH 9.2), 15 mM KOAc, 3.5 mM Mg(OAc)$_2$, 3.75 µg/ml BSA (final concentration), 200 µM each deoxyribonucleotide triphosphate, 10 pmole of each primer and 0.5 µl of "Advantage"-brand cDNA polymerase (Clonetech). Amplification was carried out as follows: initial denaturation at 94° C. for 3 minutes, followed by 35 cycles of the following: 94° C. for 1 min, 60° C. for 30 sec, 72° C. for 1 min. A final extension cycle of 72° C. for 7 min was carried out, followed by reaction termination at 4° C.

A single 480 bp PCR band was generated which was resolved on a 1% "SeaKem Gold"-brand agarose gel (FMC BioProducts, Rockland, Me.), and gel-purified using the Qiagen Gel Extraction Kit. The staggered ends on the fragment were "filled-in" using T4 DNA polymerase (Life Technologies, Rockville, Md.) as per the manufacturer's instructions, and the DNA fragments were cloned into the PCR-Blunt vector (Invitrogen, Carlsbad, Calif.). The recombinant plasmids were transformed into TOP10 supercompetent cells (Invitrogen), and eight clones were sequenced and a database search (Gen-EMBL) was carried out.

Clones "sdd17-7-1" to "sdd17-7-8" were all found to contain and 483 bp insert. The deduced amino acid sequence from this fragment showed highest identity to the following proteins (based on a "tFastA" search):

1. 37.9% identity in 161 amino acid overlap with an omega-3 (delta-15) desaturase from *Synechocystis* sp. (Accession # D13780).

2. 40.7% identity in 113 amino acid overlap with *Picea abies* plastidial omega-3 desaturase (Accession # AJ302017).

3. 35.9% identity in 128 amino acid overlap with *Zea mays* FAD8 fatty acid desaturase (Accession # D63953).

Based on its sequence homology to known omega-3 fatty acid desaturases, it seemed likely that this DNA fragment was part of an omega-3 desaturase gene present in *S. diclina*.

The DNA sequence identified above was used in the design oligonucleotides to isolate the 3' and the 5' ends of this gene from the cDNA library described in Example 1. To isolate the 3' end of the gene, the following oligonucleotides were designed:

```
RO 1188 (Forward):
                                  (SEQ. ID. NO: 12)
5'-TAC GCG TAC CTC ACG TAC TCG CTC G-3'.

RO 1189 (Forward):
                                  (SEQ. ID. NO: 13)
5'-TTC TTG CAC CAC AAC GAC GAA GCG ACG-3'.

RD 1190 (Forward):
                                  (SEQ. ID. NO: 14)
5'-GGA GTG GAC GTA CGT CAA GGG CAA C-3'.

RD 1191 (Forward):
                                  (SEQ. ID. NO: 15)
5'-TCA AGG GCA ACC TCT CGA GCG TCG AC-3'.
```

These primers (SEQ. ID. NOS: 12-15) were used in combinations with the pBluescript SK(+) vector oligonucleotide:

```
RO 898:
                                  (SEQ. ID. NO: 16)
5'-CCC AGT CAC GAC GTT GTA AAA CGA CGG CCA G-3'.
```

PCR amplifications were carried out using either the "Taq PCR Master Mix" brand polymerase (Qiagen) or "Advantage"-brand cDNA polymerase (Clonetech) or "Platinum"-brand Taq DNA polymerase (Life Technologies), as follows:

For the "Taq PCR Master Mix" polymerase, 10 pmoles of each primer were used along with 1 µl of the cDNA library DNA from Example 1. Amplification was carried out as follows: initial denaturation at 94° C. for 3 min, followed by 35 cycles of the following: 94° C. for 1 min, 60° C. for 30 sec, 72° C. for 1 min. A final extension cycle of 72° C. for 7 min was carried out, followed by the reaction termination at 4° C. This amplification resulted in the most distinct bands as compared with the other two conditions tested.

For the "Advantage"-brand cDNA polymerase reaction, PCR amplification was carried out in a 50 µl total volume containing: 1 µl of the cDNA library template from Example 1, PCR buffer containing 40 mM Tricine-KOH (pH 9.2), 15 mM KOAc, 3.5 mM Mg(OAc)$_2$, 3.75 µg/ml BSA (final concentration), 200 µM each deoxyribonucleotide triphosphate, 10 pmole of each primer and 0.5 µl of cDNA polymerase (Clonetech). Amplification was carried out as described for the Taq PCR Master Mix.

For the "Platinum"-brand Taq DNA polymerase reaction, PCR amplification was carried out in a 50 µl total volume containing: 1 µl of the cDNA library template from Example 1, PCR buffer containing 20 mM Tris-Cl, pH 8.4, 50 mM KCl (final concentration), 200 mM each deoxyribonucleotide triphosphate, 10 pmole of each primer, 1.5 mM MgSO$_4$, and 0.5 µl of Platinum Taq DNA polymerase. Amplification was carried out as follows: initial denaturation at 94° C. for 3 min, followed by 30 cycles of the following: 94° C. for 45 sec, 55° C. for 30 sec, 68° C. for 2 min. The reaction was terminated at 4° C.

All four sets of primers in combination with the vector primer generated distinct bands. PCR bands from the combination (RO 1188+RO 898) were >500 bp and this was gel-purified and cloned separately. The PCR bands generated from the other primer combinations were <500 bp. The bands were gel-purified, pooled together, and cloned into PCR-Blunt vector (Invitrogen) as described earlier. The recombinant plasmids were transformed into TOP10 supercompetent cells (Invitrogen) and clones were sequenced and analyzed.

Clone "'sdd17-16-4" and "sdd16-6" containing the ~500 bp insert, and clones "sdd17-17-6," "sdd17-17-10," and "sdd17-20-3," containing the ~400 bp inserts, were all found to contain the 3'-end of the putative omega-3 desaturase. These sequences overlapped with each other, as well as with the originally identified fragment of this putative omega-3 desaturase gene. All of the sequences contained the 'TAA' stop codon and a poly-A tail typical of 3'-ends of eukaryotic genes. This 3'-end sequence was homologous to other known omega-3 desaturases, sharing the highest identity (41.5% in 130 amino acid overlap) with the *Synechocystis* delta-15 desaturase (Accession # D13780).

For the isolation of the 5'-end of the this gene, the following oligonucleotides were designed and used in combinations with the pBluescript SK(+) vector oligonucleotide:

```
RO 899:
                                          (SEQ. ID. NO: 17)
5'-AGC GGA TAA CAA TTT CAC ACA GGA AAC AGC-3'.

RO 1185 (Reverse):
                                          (SEQ. ID. NO: 18)
5'-GGT AAA AGA TCT CGT CCT TGT CGA TGT TGC-3'.

RO 1186 (Reverse):
                                          (SEQ. ID. NO: 19)
5'-GTC AAA GTG GCT CAT CGT GC-3'.

RO 1187 (Reverse):
                                          (SEQ. ID. NO: 20)
5'-CGA GCG AGT ACG TGA GGT ACG CGT AC-3'.
```

Amplifications were carried out using either the "Taq PCR Master Mix"-brand polymerase (Qiagen) or the "Advantage"-brand cDNA polymerase (Clonetech) or the "Platinum"-brand Taq DNA polymerase (Life Technologies), as described hereinabove for the 3' end isolation.

PCR bands generated from primer combinations (RO 1185 or RO 1186+RO 899) were between ~580 to ~440 bp and these were pooled and cloned into PCR-Blunt vector as described above. Clones thus generated included "sdd17-14-1," "sdd17-14-10," "sdd17-18-2," and "sdd17-18-8," all of which showed homology with known omega-3 desaturases.

Additionally, bands generated from (RO 1187+RO 899) were ~680 bp, and these were cloned separately to generate clones "sdd17-22-2" and "sdd17-22-5" which also showed homology with known omega-3 desaturases. All these clones overlapped with each other, as well as with the original fragment of the unknown putative omega-3 desaturase. These sequences contained an ATG' site followed by an open reading frame, indicating that it is the start site of this gene. These fragments showed highest identity (39.7% in 146 amino acid overlap) with the delta-15 desaturase from *Calendula officinalis* (Accession # AJ245938).

The full-length of this omega-3 desaturase was obtained by PCR amplification of the *S. diclina* cDNA library using the following oligonucleotides:

RO 1212 (Forward): 5'-TCA ACA GAATTC ATG ACC GAG GAT AAG ACG AAG GTC GAG TTC CCG-3' (SEQ. ID. NO: 21). This primer contains the 'ATG' start site (single underline) followed by the 5' sequence of the omega-3 desaturase. In addition, an EcoRI site (double underline) was introduced upstream of the start site to facilitate cloning into the yeast expression vector pYX242.

RO 1213 (Reverse): 5'-AAA AGA AAGCTT CGC TTC CTA GTC TTA GTC CGA CTT GGC CTT GGC-3' (SEQ. ID. NO: 22). This primer contains the 'TAA' stop codon (single underline) of the gene as well as sequence downstream from the stop codon. This sequence was included because regions within the gene were very G+C rich, and thus could not be Included in the design of oligonucleotides for PCR amplification. In addition, a HindIII site (double underline) was included for convenient cloning into a yeast expression vector pYX242.

PCR amplification was carried out using the "Taq PCR Master Mix"-brand polymerase (Qiagen), 10 pmoles of each primer, and 1 µl of the cDNA library DNA from Example 1. Amplification was carried out as follows: initial denaturation at 94° C. for 3 min, followed by 35 cycles of the following: 94° C. for 1 min, 60° C. for 30 sec, 72° C. for 1 min. A final extension cycle of 72° C. for 7 min was carried out, followed by the reaction termination at 4° C.

A PCR band of ~1 kb was thus obtained and this band was isolated, purified, cloned into PCR-Blunt vector (Invitrogen), and transformed into TOP10 cells. The inserts were sequenced to verify the gene sequence. Clone "sdd17-27-2" was digested with EcoRI/HindIII to release the full-length insert, and this insert was cloned into yeast expression vector pYX242, previously digested with EcoRI/HindIII. This construct contained 1077 bp of sdd17 cloned into pYX242. This construct was labeled pRSP19, which was transformed into yeast SC334 for expression studies.

In addition, the *S. diclina* omega-3 gene was cloned into another yeast expression vector, pYES2 (Invitrogen). For this, the omega-3 desaturase gene was isolated from the cDNA library generated in Example 1 by PCR amplification (as described above) using the following oligonucleotides:

```
RO1221 (Forward)
                                          (SEQ. ID. NO: 23)
5'-TCA ACA AAG CTT ATG ACC GAG GAT AAG ACG AAG GTC
GAG TTC CCG-3'
```

This primer contains the 'ATG' start site (underlined) followed by the 5' sequence of the omega-3 desaturase. In addition, a HindIII site (bold) was introduced upstream of the start site to facilitate cloning into the pYES2 yeast expression vector.

```
RO1222 (Reverse)
                                          (SEQ. ID. NO: 24)
5'-AAA AGA GAA TTC CGC TTC CTA GTC TTA GTC CGA CTT
GGC CTT GGC-3'
```

This primer contains the 'TAA' stop codon (underlined) of the gene as well as sequence downstream from the stop codon. This sequence was included since regions within the gene were very G+C rich, and thus could not be included in the design of oligonucleotides for PCR amplification. In addition, an EcoRI site (bold) was included for convenient cloning into the pYES2 yeast expression vector.

The ~1 kb PCR band thus generated was digested with HindIII/EcoRI, and cloned into pYES2 digested with the same restriction enzymes. The resulting construct (sdd17+pYES2) was labeled pRSP20, and was used in co-expression studies.

Attempts were also made to isolate the full-length sdd17 gene from genomic DNA by PCR amplification. However, the PCR product obtained was larger than 1077 bp (~1.15 kb), and sequencing of this product revealed the presence of small introns in the genomic sequence.

The full-length gene of this putative omega-3 desaturase (labeled sdd17) was 1077 bp in length and is shown in FIG. 2 (SEQ ID NO: 25).

The gene of SEQ ID NO: 25 encoded a protein of 358 amino acid residues (SEQ. ID. NO: 26) (FIG. 3). A search of the deduced protein sequence of sdd17 (using the "tFastA" program) showed the protein to have highest identity (41% in 269 amino acid overlap) with the delta-15 desaturase from *Synechocystis* sp. (ATCC Accession No. 13780) (FIG. 4) and *Synechocystis* sp. PCC6803 (ATCC Accession No. D90913). This protein shared sequence similarities with several other plant omega-3 desaturases. Comparison of this predicted protein sequence with the FAT1 enzyme from *C. elegans* (ATCC Accession L41807) revealed only a 31.6% identity in 310 amino acid overlap (FIG. 5).

Like all omega-3 desaturases, this enzyme does not contain a cytochrome b5 domain within the 5' end of its sequence. The cytochrome b5 domain is present in most "front-end" desaturating enzymes like delta 5- and delta 6-desaturases. The omega-3 desaturase described in this example includes the three histidine-rich sequences that are present in all membrane-bound desaturases. These three domains are present at position 89 to 93 (HDCGH), 125 to 129 (HRHHH), and 284 to 288 (HQVHH) of SEQ. ID. NO: 26. These histidine-rich boxes are believed to co-ordinate the diiron-oxo structure at the enzyme's active site, and are necessary for enzyme activity; see Stukey, J. E., McDonough, V. M. & Martn, C. E. (1990) *J. Biol. Chem.* 265, 20144-20149. These features are consistent with the "SDD17" protein being a member of the membrane-bound desaturase/hydroxylase family of the diiron-oxo proteins. The G+C content of this gene is 61.8%.

EXAMPLE 5

Expression of the Omega-3 Desaturase Gene ("sdd17") from *Saprolegnia diclina* in Bakers' Yeast To determine the substrate specificity and the class of reaction catalyzed by the SDD17-protein, sdd17 was heterologously expressed in a *Saccharomyces cerevisiae* (SC334). Because *S. cerevisiae* cannot synthesize fatty acids beyond OA (18:1n-9), it is an ideal system to use to determine enzyme activity on substrates longer than OA because no background enzyme activity will be detected. Suitable fatty acid substrates can be exogenously supplied to the host which are taken up by the cell and acted on by the expressed protein of the transformed sdd17 gene.

Clone pRSP19, which contained the full-length omega-3 desaturase (sdd17) from *S. diclina* cloned into pYX242, was transformed into *Saccharomyces cerevisiae* (SC334) using the "Alkali-Cation Yeast Transformation"-brand kit (BIO 101, Vista, Calif.). Transformants were selected for leucine auxotrophy on media lacking leucine (DOB [-Leu]). To detect the specific desaturase activity of these clones, transformants were grown in the presence of 50 μM of each of LA (18:2n-6), GLA (18:3n-6), DGLA (20:3n-6), AA (20:4n-6), and adrenic acid (22:4n-6). Conversion of these exogenously supplied fatty acid substrates into a product having one additional unsaturation indicates the presence of a specific desaturase activity that is not found in the wild-type *S. cerevisiae*:

Conversion of LA (18:2n-6) to ALA (18:3n-3) indicates delta-15 desaturase activity.

Conversion of GLA (18:3n-6) to STA (18:4n-3) indicates delta-15 desaturase activity.

Conversion of DGLA (20:3n-6) to ETA (20:4n-3) indicates delta-17 desaturase activity.

Conversion of AA (20:4n-6) to EPA (20:5n-3) indicates delta-17 desaturase activity.

Conversion of adrenic acid (22:4n-6) to DPA (22:5n-3) indicates delta-19 desaturase activity.

The negative control strain was *S. cerevisiae* transformed with the pYX242 vector. The experimental cultures and the control cultures were grown simultaneously and analyzed.

The cultures were vigorously agitated (250 rpm) and grown for 48 hours at 24° C. in the presence of 50 μM (final concentration) of the various substrates (see Table 3). The cells were spun down, washed once in distilled water, and the pellets resuspended in methanol; chloroform was added along with tritridecanoin (as an internal standard). These mixtures were incubated for at least an hour at room temperature, or at 4° C. overnight. The chloroform layer was extracted and filtered through a Whatman filter with 1 gm anhydrous sodium sulfate to remove particulate matter and residual water. The organic solvents were evaporated at 40° C. under a stream of nitrogen. The extracted lipids were then converted to fatty acid methyl esters (FAME) for gas chromatography analysis (GC) by adding 2 ml 0.5 N potassium hydroxide in methanol to a closed tube. The samples were heated to 95° C.-100° C. for 30 minutes and cooled to room temperature. Approximately 2 ml 14% borontrifluoride in methanol was added and the heating repeated. After the extracted lipid mixture cooled, 2 ml of water and 1 ml of hexane were added to extract the FAME for analysis by GC. The percent conversion was calculated using the formula:

$$\% \text{ Conversion} = \frac{[\% \text{ Product}]}{[\% \text{ Product} + \% \text{ Substrate}]} \times 100$$

TABLE 3

Yeast Expression of the Omega-3 Desaturase (SDD17) from *Saprolegnia diclina* at 24° C.

| Clone | Substrate* Incorporated | Product Produced | % Conversion | Enzyme Activity |
|---|---|---|---|---|
| PRSP19 | 18:2 n-6 (9.42%) | 18:3 n-3 (0%) | 0 | Delta 15 |
|  | 18:3 n-6 (9.11%) | 18:4 n-3 (0%) | 0 | Delta 15 |
|  | 20:3 n-6 (21.36%) | 20:4 n-3 (1.18%) | 5% | Delta 17 |
|  | 20:4 n-6 (32.14%) | 20:5 n-3 (5.16%) | 13.8% | Delta 17 |
|  | 22:4 n-6 (28.65%) | 22:5 n-3 (1.22%) | 4% | Delta 19 |
| Control (pYX242) | 18:2 n-6 (9.27%) | 18:3 n-3 (0%) | 0 | Delta 15 |
|  | 18:3 n-6 (9.18%) | 18:4 n-3 (0%) | 0 | Delta 15 |
|  | 20:3 n-6 (14.19%) | 20:4 n-3 (0%) | 0 | Delta 17 |
|  | 20:4 n-6 (26.56%) | 20:5 n-3 (0%) | 0 | Delta 17 |
|  | 22:4 n-6 (16.4%) | 22:5 n-3 (0%) | 0 | Delta 19 |

*50 μM substrate used
Numbers in parenthesis represent fatty acid as a percentage of total lipids from yeast.
18:2 n-6 = Linoleic acid
18:3 n-6 = gamma-linolenic acid
18:3 n-3 = alpha-linolenic acid
18:4 n-3 = stearidonic acid
20:5 n-3 = eicosapentaenoic acid
20:3 n-6 = dihomo-gamma-linolenic acid
20:4 n-6 = arachidonic acid
22:4 n-6 = adrenic acid
20:4 n-3 = eicosatetraenoic acid
22:5 n-3 = omega-3-docosapentaenoic acid Table 3 displays the enzyme activity of the sdd17-encoded protein product from *Saprolegnia diclina* (ATCC 56851). This enzyme is an active omega-3 desaturase capable of desaturating both $C_{20}$ and $C_{22}$ omega-6 fatty acids substrates to yield the corresponding omega-3 fatty acid products. This enzyme converted 13.8% of the added AA substrate to the corresponding EPA product, thus indicating delta-17 desaturase activity. In addition, this enzyme also acted on DGLA, converting it to ETA, as would be expected for a delta-17 desaturase. In this Example, however, only 5% of the added DGLA was converted to ETA, indicating that under the conditions used here, the enzyme has a substrate preference for AA as compared to DGLA.

The activity of this enzyme toward $C_{22}$ fatty acid substrates was also investigated because $C_{22}$ omega-3 fatty acids like DPA and DHA have important dietary and pharmaceutical implications. From Table 3, it can be seen that this enzyme was active on $C_{22}$ substrates such as adrenic acid, converting 4% of it to DPA. As can be seen from the control cultures, there was no non-specific conversion of exogenously added substrate to product in non-transformed *S. cerevisiae*.

Table 4 demonstrates that this omega-3 desaturase (SDD17) can also function at a lower temperature. (i.e. 15° C.). Here, 50 µM of exogenous substrate was added to the transformants and the cultures were grown for 48 hours at 15° C. Fatty acid analysis was carried out as described above. The overall uptake of substrate by *S. cerevisiae* at 15° C. was lower than that seen at 24° C. (compare Table 3 & Table 4). However the percent conversion of substrate to product by the enzyme increased at 15° C. Since the presence of lower concentration of exogenous fatty acid substrate seemed to improve the activity of the enzyme, it is possible that fatty acid substrates at high concentrations may exert a feed-back inhibition on this enzyme. Further studies may be carried out to determine the effect of different substrate concentration and different temperatures on expression of this omega-3 desaturase in *S. cerevisiae*.

TABLE 4

Yeast Expression of the Omega-3 Desaturase (SDD17) from *Saprolegnia diclina* at 15° C.

| Clone | Substrate* Incorporated | Product Produced | % Conversion | Enzyme Activity |
|---|---|---|---|---|
| PRSP19 | 18:2 n-6 (8.79%) | 18:3 n-3 (0%) | 0 | Delta 15 |
|  | 18:3 n-6 (12.69%) | 18:4 n-3 (0%) | 0 | Delta 15 |
|  | 20:3 n-6 (9.52%) | 20:4 n-3 (1.46%) | 13% | Delta 17 |
|  | 20:4 n-6 (8.69%) | 20:5 n-3 (2.05%) | 19% | Delta 17 |
|  | 22:4 n-6 (6.68%) | 22:5 n-3 (0.62%) | 8.4% | Delta 19 |
| Control (pYX242) | 18:2 n-6 (9.65%) | 18:3 n-3 (0%) | 0 | Delta 15 |
|  | 18:3 n-6 (13.55%) | 18:4 n-3 (0%) | 0 | Delta 15 |
|  | 20:3 n-6 (10.17%) | 20:4 n-3 (0%) | 0 | Delta 17 |
|  | 20:4 n-6 (16.58%) | 20:5 n-3 (0%) | 0 | Delta 17 |
|  | 22:4 n-6 (11.05%) | 22:5 n-3 (0%) | 0 | Delta 19 |

*50 µm substrate used
Numbers in parenthesis represent fatty acid as a percentage of total lipids from yeast
18:2 n-6 = Linoleic acid
18:3 n-6 = gamma-linolenic acid
18:3 n-3 = alpha-linolenic acid
18:4 n-3 = stearidonic acid
20:5 n-3 = eicosapentaenoic acid
20:3 n-6 = dihomo-gamma-linolenic acid
20:4 n-6 = arachidonic acid
22:4 n-6 = adrenic acid
20:4 n-3 = eicosatetraenoic acid
22:5 n-3 = omega-3-docosapentaenoic acid Unlike all known omega-3 desaturases, the sdd17-encoding enzyme did not desaturate any $C_{18}$ omega-6 fatty acyl substrates to their corresponding omega-3 fatty acids (under the conditions tested). It is possible that in vivo, this enzyme functions exclusively on AA, converting it to EPA. This would be consistent with the fatty acid profile of *S. diclina* displaying high amounts of AA and EPA, but little or none of the other omega-3 intermediates (Table 5).

TABLE 5

Fatty Acid Profile of *Saprolegnia diclina* ATCC 56851

| Fatty Acid | % Total Lipid |
|---|---|
| C10:0 | 0.22 |
| C12:0 | 0.1 |
| C13:0 | 3.98 |
| C14:0 | 6.0 |
| C14:1 n-5 | 0.29 |
| C15:0 | 1.06 |
| C16:0 | 19.75 |
| C16:1 n-7 | 1.99 |
| C18:0 | 3.99 |
| C18:n-9 | 15.39 |
| C18:1 n-7 | 7.39 |
| C18:1 n-5 | 0.43 |
| C18:2 n-6 | 7.07 |
| C18:3 n-6 | 2.13 |
| C18:3 n-3 | 0.08 |
| C20:0 | 0.76 |
| C20:1 n-9 | 0.15 |
| C20:1 n-7 | 0.08 |
| C20:2 n-6 | 0.22 |
| C20:3 n-6 | 1.31 |
| C20:4 n-6 | 15.42 |
| C20:5 n-3 | 12.2 |

Thus, sdd17 encodes a novel omega-3 desaturase, capable of desaturating $C_{20}$ and $C_{22}$ fatty acid substrates. The SDD17 protein can easily be expressed in a heterologous system and thus has potential for use in other heterologous systems like plants. This enzyme is very different from other known omega-3 desaturases, showing activity on both $C_{20}$ and $C_{22}$ fatty acid substrates, but not $C_{18}$ substrates. It shares only 31.6% identity with FAT-1, the only other known desaturase capable of acting on $C_{20}$ and $C_{22}$ omega-6 fatty acid substrates. Thus the enzyme encoded by sdd17 is a novel omega-3 desaturase.

EXAMPLE 6

Co-Expression of *S. diclina* Omega-3 Desaturase with Other Enzymes

The pRSP20 construct consisting of sdd17 cloned into pYES2 yeast expression vector, as described in Example 3, was used in co-expression studies with other desaturases and elongases. pRSP3, a construct that contained the delta 5-desaturase gene (SEQ ID NO: 27) from *S. diclina* cloned into the pYX242 yeast expression vector, was co-transformed with pRSP20 into yeast. Transformation protocol was as described in Example 4. This delta 5-desaturase catalyzes the conversion of DGLA to AA and ETA to EPA. Co-transformants were selected on minimal media lacking leucine and Uracil (DOB [-Leu-Ura]).

Table 6 shows that when 50 µM of the substrate DGLA (20:3 n-6) was added, the delta 5-desaturase converted it to AA (20:4, n-6), and the omega-3 desaturase was able to further desaturate AA to EPA (24:5, n-3). The percent conversion of the substrate to final product was 5%, with no background observed in the negative control.

TABLE 6

Co-expression Studies with the Omega-3 Desaturase (SDD17) from *S. diclina*

| Clone | Plasmid in yeast | 20:3 n-6 (DGLA) Incorporated | 20:4 n-6 (AA) Produced | 20:5 n-3 (EPA) Produced | % Conversion |
|---|---|---|---|---|---|

TABLE 6-continued

Co-expression Studies with the Omega-3 Desaturase (SDD17) from S. diclina

| Cntrl | pYX242 + pYES2 | 19.33 | 0 | 0 | 0 |
|---|---|---|---|---|---|
| PRSP22 | pRSP3 (Delta 5) + pRSP20 (omega-3 desaturase) | 20.56 | 2.64 | 0.14 | 5% |

| Clone | Plasmid in yeast | 18:3 n-6 (GLA) Incorporated | 20:3 n-6 (DGLA) Produced | 20:4 n-3 (ETA) Produced | % Conversion |
|---|---|---|---|---|---|
| Cntrl | pYX242 + pYES2 | 4.83 | 0 | 0 | 0 |
| PRSP23 | pRAT-4-A7 (elongase) + pRSP20 (omega-3 desaturase) | 4.56 | 9.30 | 0.14 | 1.4% |

*50 μM substrate used
Numbers represent fatty acid as a percentage of total lipids from yeast
18:3n-6 = gamma-linolenic acid
20:3n-6 = dihomo-gamma-linolenic acid
20:4n-6 = arachidonic acid
20:4n-3 = eicosatetraenoic acid
20:5n-3 = eicosapentaenoic acid $$\% \text{ Conversion} = \frac{[\% \text{ Product 1} + \% \text{ Product 2}]}{[\% \text{ substrate} + \% \text{ Product 1} + \% \text{ Product 2}]}$$

Table 6 also shows the results of a co-transformation experiment involving pRSP20 and pRAT-4-A7, an elongase obtained from *Thraustochytrid* sp. 7091 (SEQ. ID. NO: 28) cloned into pYX242. This elongase gene catalyzes the addition of two more carbons to the pre-existing PUFA. When 50 μM of the substrate GLA (18:3 n-6) was added to the co-transformants, the elongase elongated GLA to DGLA, and the DGLA was further desaturated by the omega-3 desaturase to ETA (20:4 n-3). The percent conversion of substrate to final product was 1.4%, with no background observed in the negative control.

Thus the *S. diclina* omega-3 desaturase was able to utilize a product produced, in a heterologous expression system, by another heterologous enzyme from the PUFA biosynthetic pathway, and convert that product to the expected PUFA.

It should be noted that the expression (and hence the activity) of sdd17 when cloned in the pYES2 vector (pRSP20) was much lower than when cloned into the pYX242 vector (pRSP19). This could be explained by the difference in the expression promoters present in each vector. The pYX242 promoter is a constitutive promoter and is much stronger than the galactose-inducible promoter in pYES2. Similar observations have been made during expression studies with other desaturases when cloned into these two expression vectors.

Further co-expression studies may be carried out using pRSP19 instead of pRSP20 along with other desaturases and elongases. Also the *S. diclina* omega-3 desaturase may also be co-expressed with other enzymes like the delta 4-desaturase pRTA7 (SEQ. ID. NO: 29), where in adrenic acid (22:4 n-6) may be added as a substrate and the final end product DHA (22:6 n-3) may be produced due to the concerted action of the omega-3 desaturase and the delta 4-desaturase.

EXAMPLE 7

Design of Degenerate Primers for the Isolation of the Delta 12-Desaturase Gene from *Saprolegnia diclina* ATCC 56851

Analysis of the fatty acid composition of *Saprolegnia diclina* (ATCC 56851) revealed the presence of a considerable amount of LA, which suggested the presence of a very active delta 12-desaturase (Table 5). Delta 12-desaturases use OA as a substrate, thus catalyzing the conversion of OA to LA (see FIG. 1). Delta 12-desaturases are present only in plants, fungi, and insects, but not in mammals, including humans. Thus LA is an "essential" fatty acid in humans because it cannot be synthesized in vivo. LA is further desaturated and elongated to produce important intracellular compounds like GLA, AA, and EPA.

The goal of this experiment was to isolate the delta 12-desaturase gene from *S. diclina* and verify its functionality by expressing the enzyme in a heterologous host system such as yeast. The approach taken was to design degenerate primers (oligonucleotides) that represent conserved amino acid motifs from known delta 12-desaturases. In designing these primers, known delta-12 desaturase sequence information from both fungi and plant sources was used, including sequence information from: *Mortierella alpina* (Accession #AF110509), *Mucor rouxii* (Accession #AF161219), *Brassica juncea* (Accession #X91139), *Arabidopsis thaliana* (Accession #L26296), and Borago officinalis (Accession #AF0744324). The sequence information was analyzed using the CODEHOP Blockmaker program.

The degenerate primers used in this Example were as follows:

Protein Motif 1:
(SEQ ID NO: 57)
NH$_3$-P N/E FTIKEIR D/E A/C IPAHCF-COOH

Primer RO 967 (Forward):
(SEQ. ID. NO: 30)
5'-CCG SAG TTC ACS ATC AAG GAG ATC CGC GAS KSC ATC

CCG GCC CAC TGC TTC-3'.

Protein Motif 2:
(SEQ ID NO: 58)
NH$_3$-MP H/F YHAEEAT V/Y H I/L KR A/I-COOH

Primer RO 968 (Reverse):
(SEQ. ID. NO: 31)
5'-GRS CTT CTT GAK GTG GWM SGT GGC CTC CTC GGC GTG

GTA GWR CGG CAT-3'.

Protein Motif 3:
(SEQ ID NO: 59)
NH$_3$-P L/V YW A/I C/M/A QG V/I V L/G/C TGVW-COOH Primer RO 964 (Forward):
(SEQ. ID. NO: 32)
5'-CCS STC TAC TGG GCC TGC CAG GGT RTC GTC CTC ACS

GGT GTC TGG-3'.

This sequence is more similar to the known plant Delta 12-desaturases.

Primer RO 965 (Forward):
(SEQ. ID. NO: 33)
5'-CCS STC TAC TGG ATC RYS CAG GGT RTC GTC KGY ACS

GGT GTC TGG-3'.

This sequence is more similar to the known fungal Delta 12-desaturases.

Protein Motif 4:
(SEQ ID NO: 60)
NH₃-HVAHH L/F FS T/Q MPHYHA-COOH

Primer RO 966 (Reverse):
(SEQ. ID. NO: 34)
5'-GGC GTG GTA GTG CGG CAT SMM CGA GAA GAR GTG GTG GGC GAC GTG-3'.

The degeneracy code used for the oligonucleotides was as follows: R=A/G; Y=C/T; M=A/C; K=G/T; W=A/T; S=C/G; B=C/G/T; D=A/G/T; H=A/C/T; V=A/C/G; N=A/C/G/T.

EXAMPLE 8

Identification and Isolation of the Delta 12-Desaturase Gene from *Saprolegnia diclina* (ATCC 56851)

To isolate a fragment of the delta 12-desaturase gene from *S. diclina*, PCR was carried out using the *S. diclina* cDNA library from Example 1 as a template. Primers were used in the following combinations: (RO 964+RO 966), (RO 965+RO 966), and (RO 967+RO 968). PCR was carried out in 100 μl volumes using the "Taq PCR Master Mix"-brand polymerase (Qiagen). 10 pmoles of each primer were used along with 1 μl of the cDNA library DNA. Amplification was carried out as follows: initial denaturation at 94° C. for 4 min, followed by 25 cycles of the following: 94° C. for 1 min, 47° C. for 1 min, 72° C. for 2 min. A final extension cycle of 72° C. for 5 min was carried out, followed by reaction termination at 4° C.

Amplification with (RO 964+RO 966) or (RO 965+RO 966) resulted in distinct bands of ~688 bp in length. Amplification with (RO 967+RO 968) resulted in one distinct band of ~660 bp. These bands were resolved on a 1% "SeaKem Gold"-brand agarose gel (FMC BioProducts), and gel-purified using the Qiagen Gel Extraction Kit. The staggered ends on the fragment were "filled-in" using T4 DNA polymerase (Life Technologies), following the manufacturer's specifications. The DNA fragments were then cloned into the PCR-Blunt vector (Invitrogen). The recombinant plasmids were transformed into TOP10 supercompetent cells (Invitrogen), clones were sequenced, and a database search (Gen-EMBL) was carried out.

Clones "sdd12-1-8," "sdd12-2-8," and "sdd12-5-1" were all found to overlap with each other, and these overlapping fragments were aligned using the "ASSEMBLE"-brand program (GCG) to create a single fusion fragment of ~900 bp. A "tFastA" search with the deduced amino acids of this fusion sequence showed highest identity to the following proteins:

49% identity in 298 amino acid overlap with Borago officinalis Delta 12-desaturase (Accession #AF074324) and 46.7% identity in 332 amino acid overlap with Sesamum indicum Delta 12-desaturase (Accession # AF192486).

Based on the high identity to known delta 12-desaturases, the fragment was considered to be a region of the *S. diclina* delta 12-desaturase gene. This fragment was used to design primers to pull up the 5'- and 3'-ends of the gene.

To isolate the 3' end of the gene, the following oligonucleotides were designed:

RO 975 (Forward):
(SEQ. ID. NO: 35)
5'-CAC GTA CCT CCA GCA CAC GGA CAC CTA CG-3'.

RO 976 (Forward):
(SEQ. ID. NO: 36)
5'-GAT CGA CAG CGC GAT CCA CCA CAT TGC-3'.

These were used in combinations with the pBluescript SK(+) vector oligonucleotide RO 898: 5'-CCC AGT CAC GAC GTT GTA AAA CGA CGG CCA G-3' (SEQ. ID. NO: 16).

PCR amplifications were carried out using "Taq PCR Master Mix"-brand polymerase (Qiagen) as follows: 10 pmoles of each primer were used along with 1 μl of the cDNA library DNA from Example 1 as template. Amplification conditions were as follows: initial denaturation at 94° C. for 3 min, followed by 35 cycles of the following: 94° C. for 1 min, 60° C. for 30 sec, 72° C. for 1 min. A final extension cycle of 72° C. for 7 min was carried out, followed by reaction termination at 4° C.

Primer combination (RO 898+RO 975) generated a PCR band of ~390 bp and primer combination (RO 898+RO 976) generated a band of length 300 bp. These bands were purified and cloned into PCR-Blunt vector as described earlier. Several clones, including clones "sdd12-8-12" and "sdd12-9-4" were found to contain the 3' end of the delta 12-desaturase gene. These sequences overlapped the initial delta-12 desaturase fragment and included a TAA stop codon and a poly-A tail. Sequence analysis with the "tFastA" program revealed that clone "sdd12-9-4" shared 54.5% identity in a 73 amino acid overlap with the delta 12-desaturase from *Mortierella alpina* (Accession #AB020033), and 56.9% identity in a 72 amino acid overlap with the delta 12-desaturase from *Mucor rouxii* (Accession #AF161219).

To isolate the 5' end of the this gene, the following oligonucleotides were designed and used in combinations with the pBluescript SK(+) vector oligonucleotide RO 899 (SEQ. ID. NO: 17).

RO 977 (Reverse):
(SEQ ID NO: 37)
5'-CAA ATG GTA AAA GCT AGT GGC AGC GCT GC-3'.

RO 978 (Reverse):
(SEQ ID NO: 38)
5'-AGT ACG TGC CCT GGA CGA ACC AGT AGA TG-3'.

PCR amplifications were carried out using either "Taq PCR Master Mix"-brand polymerase (Qiagen) or the "Advantage-GC"-brand cDNA PCR kit (Clonetech). The Clonetech product was used to circumvent potential PCR amplification problems that may occur with GC-rich regions generally present at the 5'-end of desaturases from this organism. PCR amplifications using the "Taq PCR Master Mix"-brand polymerase was carried out as described for the isolation of 3'-end of this gene.

When using the "Advantage-GC cDNA PCR"-brand kit, thermocycling conditions were as follows: the template was initially denatured at 94° C. for 1 min, followed by 30 cycles of 94° C. for 30 seconds, 68° C. for 3 minutes, and finally an extension cycle at 68° C. for 5 min. Each reaction included 1 μl of cDNA library template (from Example 1), 10 pmole of each primer, 0.2 mM each dNTP, 1M GC Melt, 40 mM Tricine-KOHR, 15 mM KOAC, 3.5 mM MG(OAc)₂/5% DMSO, and 375 μg/ml BSA in a total volume of 50 μl.

A PCR product of ~371 bp was obtained using the primer combination (RO 899+RO 978). This band was cloned into the PCR-Blunt vector (Invitrogen) as described earlier. Only one clone, "sdd12-10-8," thus obtained contained the putative ATG start site of the gene. Other clones had the ATG replaced by other codons. "tFastA" analysis of the deduced amino acid sequence of "sdd12-10-8" showed 47.2% identity in a 72 amino acid overlap of the delta-12 desaturase from *Impatiens balsamina* (Accession #AF182520) and 42.7% identity in a 75 amino acid overlap with the delta-12 desaturase from *Calendula officinalis* (Accession #AJ245938).

The full length of this delta 12-desaturase was obtained by PCR amplification of the *S. diclina* cDNA library of Example 1 using the following oligonucleotides:

RO1051 (Forward): 5'-TCA ACA GAATTC ATG TGC AAA GGT CAA GCT CCT TCC AAG GCC GAC GTG-3' (SEQ. ID. 39). This primer contains the 'ATG' start site (underlined) followed by the 5' sequence of the Delta 12-desaturase. In addition, an EcoRI site (double underline) was introduced upstream of the start site to facilitate cloning into the pYX242 yeast expression vector.

RO1057 (Reverse): 5'-AAA AGA AAGCTT TTA CTT TTC CTC GAG CTT GCG CTT GTA AAA CAC AAC-3' (SEQ. ID. NO: 40). This primer contains the TAA stop codon (underlined) of the gene as well as a HindIII site (double underline), which was included for convenient cloning into the pYX242 yeast expression vector.

PCR amplifications were carried out using both "Taq PCR Master Mix"-brand polymerase (Qiagen) and the "Advantage-GC cDNA PCR"-brand kit (Clonetech), as described earlier. In this case, however, *S. diclina* genomic DNA was used as the template for amplification. A PCR band of ~1.1 kb was thus obtained and this band was isolated, purified, cloned into PCR-Blunt vector (Invitrogen), and transformed into TOP10 cells. The inserts were sequenced to verify the gene sequence. Clone "sdd12-gg-b1" was digested with EcoRI/HindIII to release the full-length insert, and this insert was cloned into the yeast expression vector pYX242, previously digested with EcoRI/HindIII. This construct included 1182 bp of the delta-12 desaturase gene and pYX242. The construct was labeled pRSP11. The pRSP11 construct was then transformed into *S. cerevisiae* (SC334) for expression studies.

The full-length gene of this putative delta-12 desaturase (labeled sdd12) was 1182 bp in length (SEQ ID NO: 41) (FIG. 6). The gene encodes a protein of 393 amino acid residues (SEQ ID NO: 42) (FIG. 7). A "tFastA" search of the deduced protein sequence of sdd12 showed the protein to have highest identity (45.6% in a 379 amino acid overlap) with the delta-12 desaturase from *Gossypium hirsutum* (Accession #X97016) (FIG. 8) and 49.6% identity in a 353 amino acid overlap with the delta-12 desaturase from *Sesamum indicum* (FAD2) (Accession #AF192486).

Like other delta-12 desaturases, this enzyme also does not contain a cytochrome b5 domain within the 5' end of its' sequence. This enzyme does contain the three histidine-rich sequences that are present in all membrane-bound desaturases. The position and length of these histidine-boxes are similar to those seen in other desaturases. These are present at amino acid positions 108 to 112 (HECGH), 144 to 148 (HRRHH), and 326 to 330 (HVTHH) of SEQ. ID. NO: 42. As noted earlier, these histidine-rich boxes are believed to co-ordinate the diiron-oxo structure at the enzyme's active site and are necessary for enzyme activity.

Example 9

Expression of the Delta 12-Desaturase Gene (sdd12) in Bakers' Yeast

To determine the substrate specificity and the class of reaction catalyzed by this delta 12-desaturase (SDD12), sdd12 was heterologously expressed in a *Saccharomyces cerevisiae* (SC334). As noted earlier, because *S. cerevisiae* cannot synthesize fatty acids beyond OA, it is an ideal system to determine enzyme activity on substrates longer than OA because no background enzyme activity will be detected. Suitable fatty acid substrates are exogenously supplied to the host; these substrates are taken up by the cell and acted on by the expressed delta-12 desaturase of the transformed sdd12 gene.

Clone pRSP11, which contained the full-length delta-12 desaturase (sdd12) from *S. diclina*, cloned into pYX242, was transformed into *Saccharomyces cerevisiae* (SC334) using the "Alkali-Cation Yeast Transformation"-brand kit (BIO 101), following the manufacturer's instructions. Transformants were selected for leucine auxotrophy on media lacking leucine (DOB-Leu). To detect the specific desaturase activity of these clones, transformants were grown in the presence of 50 μM each of OA, LA, GLA, and DGLA.

Conversion of OA to LA (18:2n-6) indicates delta-12 desaturase activity.

Conversion of LA to ALA (18:3n-3) indicates delta-15 desaturase activity.

Conversion of LA to GLA (18:3n-6) indicates delta-6 desaturase activity.

Conversion of GLA to stearidonic (18:4n-3) acid indicates delta-15 desaturase activity.

Conversion of DGLA to ETA (20:4n-3) indicates delta-17 desaturase activity.

Conversion of DGLA to AA (20:4n-6) indicates delta-5 desaturase activity.

The negative control strain was *S. cerevisiae* transformed with the pYX242 vector. The experimental and control cultures were grown simultaneously and analyzed.

The cultures were vigorously agitated (250 rpm) and grown for 48 hours at 24° C. in the presence of 50 μM (final concentration) of the various substrates (see Table 7). The cells were spun down, washed once in distilled water, and the pellets resuspended in methanol; chloroform was added along with tritridecanoin (as an internal standard). These mixtures were incubated for at least an hour at room temperature, or at 4° C. overnight. The chloroform layer was extracted and filtered through a Whatman filter with 1 gm anhydrous sodium sulfate to remove particulate matter and residual water. The organic solvents were evaporated at 40° C. under a stream of nitrogen. The extracted lipids were then converted to fatty acid methyl esters (FAME) for gas chromatography analysis (GC) by adding 2 ml 0.5 N potassium hydroxide in methanol to a closed tube. The samples were heated to 95° C.-100° C. for 30 minutes and cooled to room temperature. Approximately 2 ml 14% borontrifluoride in methanol was added and the heating repeated. After the extracted lipid mixture cooled, 2 ml of water and 1 ml of hexane were added to extract the FAME for analysis by GC. The percent conversion was calculated using the formula:

$$\% \text{ Conversion} = \frac{[\% \text{ Product}]}{[\% \text{ Product} + \% \text{ Substrate}]} \times 100$$

Table 7 shows the enzyme activity of the delta-12 desaturase when expressed in yeast. Here, the pRSP11 clone when expressed was capable of converting 35.8% of OA substrate to LA, indicating delta-12 desaturase activity.

In Table 7, the fatty acids of interest are represented as a percentage of the total lipids extracted from yeast. GC/MS was employed to identify the products. Under these conditions, the clones did not exhibit other desaturase activities.

This confirmed that the gene isolated is a delta-12 desaturase gene. No background substrate conversion was detected using hosts transformed with just the vector alone. This data indicates that this delta-12 desaturase can be expressed in a heterologous system and is thus useful in the production of transgenic polyunsaturated fatty acids like GLA, AA, EPA and DHA.

TABLE 7

*Saprolegnia diclina* Delta 12-Desaturase Expression in Baker's Yeast at 24° C.

| Clone | Desatur. Activity | Substrate* Incorporated | Product Produced | % Conversion of Substrate |
|---|---|---|---|---|
| pRSP11 (pYX242 + Delta 12- Desaturase (*S. diclina*)) | Delta 12 | OA (17.09%) | LA (9.59%) | 35.8% |
| | Delta 15 | LA (18.14%) | ALA (0.06%) | 0 |
| | Delta 6 | LA (18.14%) | GLA (0%) | 0 |
| | Delta 5 | DGLA (25.38%) | AA (0.17%) | 0 |
| | Delta 17 | DGLA (25.38%) | ETA (0.07%) | 0 |
| Control (pYX242) | Delta 12 | OA (18.99%) | LA (0.09%) | 0 |
| | Delta 15 | LA (8.63%) | ALA (0%) | 0 |
| | Delta 6 | LA (8.63%) | GLA (0%) | 0 |
| | Delta 5 | DGLA (13.74%) | AA (0%) | 0 |
| | Delta 17 | DGLA (13.74%) | ETA (0%) | 0 |

*50 μm substrate used
Numbers in parenthesis represent fatty acid as a percentage of total lipids from yeast.

Nutritional Compositions

The PUFAs described in the Detailed Description may be utilized in various nutritional supplements, infant formulations, nutritional substitutes and other nutritional solutions.

I. Infant Formulations

A. Isomil® Soy Formula with Iron:

Usage: As a beverage for infants, children and adults with an allergy or sensitivity to cows milk. A feeding for patients with disorders for which lactose should be avoided: lactase deficiency, lactose intolerance and galactosemia.

Features:
  Soy protein isolate to avoid symptoms of cow's-milk-protein allergy or sensitivity.
  Lactose-free formulation to avoid lactose-associated diarrhea.
  Low osmolality (240 mOs/kg water) to reduce risk of osmotic diarrhea.
  Dual carbohydrates (corn syrup and sucrose) designed to enhance carbohydrate absorption and reduce the risk of exceeding the absorptive capacity of the damaged gut.
  1.8 mg of Iron (as ferrous sulfate) per 100 Calories to help prevent iron deficiency.
  Recommended levels of vitamins and minerals.
  Vegetable oils to provide recommended levels of essential fatty acids.
  Milk-white color, milk-like consistency and pleasant aroma.
  Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and disglycerides, soy lecithin, carrageenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

B. Isomil® DF Soy Formula For Diarrhea:

Usage: As a short-term feeding for the dietary management of diarrhea in infants and toddlers.

Features:
  First infant formula to contain added dietary fiber from soy fiber specifically for diarrhea management.
  Clinically shown to reduce the duration of loose, watery stools during mild to severe diarrhea in infants.
  Nutritionally complete to meet the nutritional needs of the infant.
  Soy protein isolate with added L-methionine meets or exceeds an infant's requirement for all essential amino acids.
  Lactose-free formulation to avoid lactose-associated diarrhea.
  Low osmolality (240 mOsm/kg water) to reduce the risk of osmotic diarrhea.
  Dual carbohydrates (corn syrup and sucrose) designed to enhance carbohydrate absorption and reduce the risk of exceeding the absorptive capacity of the damaged gut.
  Meets or exceeds the vitamin and mineral levels recommended by the Committee on Nutrition of the American Academy of Pediatrics and required by the Infant Formula Act.
  1.8 mg of iron (as ferrous sulfate) per 100 Calories to help prevent iron deficiency.
  Vegetable oils to provide recommended levels of essential fatty acids.
  Ingredients: (Pareve) 86% water, 4.8% corn syrup, 2.5% sugar (sucrose), 2.1% soy oil, 2.0% soy protein isolate, 1.4% coconut oil, 0.77% soy fiber, 0.12% calcium citrate, 0.11% calcium phosphate tribasic, 0.10% potassium citrate, potassium chloride, potassium phosphate monobasic, mono and diglycerides, soy lecithin, carrageenan, magnesium chloride, ascorbic acid, L-methionine, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

C. Isomil® SF Sucrose-Free Soy Formula with Iron:

Usage: As a beverage for infants, children and adults with an allergy or sensitivity to cow's-milk protein or an intolerance to sucrose. A feeding for patients with disorders for which lactose and sucrose should be avoided.

Features:
  Soy protein isolate to avoid symptoms of cow's-milk-protein allergy or sensitivity.
  Lactose-free formulation to avoid lactose-associated diarrhea (carbohydrate source is Polycose® Glucose Polymers).
  Sucrose free for the patient who cannot tolerate sucrose.
  Low osmolality (180 mOsm/kg water) to reduce risk of osmotic diarrhea.
  1.8 mg of iron (as ferrous sulfate) per 100 Calories to help prevent iron deficiency.
  Recommended levels of vitamins and minerals.
  Vegetable oils to provide recommended levels of essential fatty acids.
  Milk-white color, milk-like consistency and pleasant aroma.
  Ingredients: (Pareve) 75% water, 11.8% hydrolized cornstarch, 4.1% soy oil, 4.1% soy protein isolate, 2.8% coconut oil, 1.0% modified cornstarch, 0.38% calcium phosphate tribasic, 0.17% potassium citrate, 0.13% potassium chloride, mono- and diglycerides, soy lecithin, magnesium chloride, abscorbic acid, L-methionine, calcium carbonate, sodium chloride, choline chloride, carrageenan, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

D. Isomil® 20 Soy Formula with Iron Ready to Feed, 20 Cal/fl Oz.:
  Usage: When a soy feeding is desired.
  Ingredients: (Pareve) 85% water, 4.9% corn syrup, 2.6% sugar(sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and diglycerides, soy lecithin, carrageenan, abscorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

E. Similac® Infant Formula:
  Usage: When an infant formula is needed: if the decision is made to discontinue breastfeeding before age 1 year, if a supplement to breastfeeding is needed or as a routine feeding if breastfeeding is not adopted.
Features:
  Protein of appropriate quality and quantity for good growth; heat-denatured, which reduces the risk of milk-associated enteric blood loss.
  Fan from a blend of vegetable oils (doubly homogenized), providing essential linoleic acid that is easily absorbed.
  Carbohydrate as lactose in proportion similar to that of human milk.
  Low renal solute load to minimize stress on developing organs.
  Powder, Concentrated Liquid and Ready To Feed forms.
  Ingredients: (-D) Water, nonfat milk, lactose, soy oil, coconut oil, mono- and diglycerides, soy lecithin, abscorbic acid, carrageenan, choline chloride, taurine, m-inositol, alpha-tocopheryl acetate, zinc sulfate, niacinamide, ferrous sulfate, calcium pantothenate, cupric sulfate, vitamin A palmitate, thiamine chloride hydrochloride, riboflavin, pyridoxine hydrochloride, folic acid, manganese sulfate, phylloquinone, biotin, sodium selenite, vitamin D3 and cyanocobalamin.

F. Similac® Neocare Premature Infant Formula with Iron:
  Usage: For premature infants' special nutritional needs after hospital discharge. Similac NeoCare is a nutritionally complete formula developed to provide premature infants with extra calories, protein, vitamins and minerals needed to promote catch-up growth and support development.
Features:
  Reduces the need for caloric and vitamin supplementation.
  More calories (22 Cal/fl oz) than standard term formulas (20 Cal/fl oz).
  Highly absorbed fat blend, with medium-chain triglycerides (MCToil) to help meet the special digestive needs of premature infants.
  Higher levels of protein, vitamins and minerals per 100 calories to extend the nutritional support initiated in-hospital.
  More calcium and phosphorus for improved bone mineralization.
  Ingredients: -D Corn syrup solids, nonfat milk, lactose, whey protein concentrate, soy oil, high-oleic safflower oil, fractionated coconut oil (medium chain triglycerides), coconut oil, potassium citrate, calcium phosphate tribasic, calcium carbonate, ascorbic acid, magnesium chloride, potassium chloride, sodium chloride, taurine, ferrous sulfate, m-inositol, choline chloride, ascorbyl palmitate, L-carnitine, alpha-tocopheryl acetate, zinc sulfate, niacinamide, mixed tocopherols, sodium citrate, calcium pantothenate, cupric sulfate, thiamine chloride hydrochloride, vitamin A palmitate, beta carotene, riboflavin, pyridoxine hydrochloride, folic acid, manganese sulfate, phylloquinone, biotin, sodium selenite, vitamin D3 and cyanocobalamin.

G. Similac Natural Care Low-Iron Human Milk Fortifier Ready to Use, 24 Cal/Fl Oz.:
  Usage: Designed to be mixed with human milk or to be fed alternatively with human milk to low-birth-weight infants.
  Ingredients: -D Water, nonfat milk, hydrolyzed cornstarch, lactose, fractionated coconut oil (medium-chain triglycerides), whey protein concentrate, soy oil, coconut oil, calcium phosphate tribasic, potassium citrate, magnesium chloride, sodium citrate, ascorbic acid, calcium carbonate, mono and diglycerides, soy lecithin, carrageenan, choline chloride, m-inositol, taurine, niacinamide, L-carnitine, aloha tocopheryl acetate, zinc sulfate, potassium chloride, calcium pantothenate, ferrous sulfate, cupric sulfate, riboflavin, vitamin A palmitate, thiamine chloride hydrochloride, pyridoxine hydrochloride, biotin, folic acid, manganese sulfate, phylloquinone, vitamin D3, sodium selenite and cyanocobalamin.

Various PUFAs of this invention can be substituted and/or added to the infant formulae described above and to other infant formulae known to those in the art.

II. Nutritional Formulations

A. Ensure®
  Usage: ENSURE is a low-residue liquid food designed primarily as an oral nutritional supplement to be used with or between meals or, in appropriate amounts, as a meal replacement. ENSURE is lactose- and gluten-free, and is suitable for use in modified diets, including low-cholesterol diets. Although it is primarily an oral supplement, it can be fed by tube.
Patient Conditions:
  For patients on modified diets
  For elderly patients at nutrition risk
  For patients with involuntary weight loss
  For patients recovering from illness or surgery For patients who need a low-residue diet Ingredients: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate.

B. Ensure® Bars:

Usage: ENSURE BARS are complete, balanced nutrition for supplemental use between or with meals. They provide a delicious, nutrient-rich alternative to other snacks. ENSURE BARS contain <1 g lactose/bar, and Chocolate Fudge Brownie flavor is gluten-free. (Honey Graham Crunch flavor contains gluten.)

Patient Conditions:
  For patients who need extra calories, protein, vitamins and minerals.
  Especially useful for people who do not take in enough calories and nutrients.
  For people who have the ability to chew and swallow
  Not to be used by anyone with a peanut allergy or any type of allergy to nuts.

Ingredients: Honey Graham Crunch—High-Fructose Corn Syrup, Soy Protein Isolate, Brown Sugar, Honey, Maltodextrin (Corn), Crisp Rice (Milled Rice, Sugar [Sucrose], Salt (Sodium Chloride) and Malt), Oat Bran, Partially Hydrogenated Cottonseed and Soy Oils, Soy Polysaccharide, Glycerine, Whey Protein Concentrate, Polydextrose, Fructose, Calcium Caseinate, Cocoa Powder, Artificial Flavors, Canola Oil, High-Oleic Safflower Oil, Nonfat Dry Milk, Whey Powder, Soy Lecithin and Corn Oil. Manufactured in a facility that processes nuts.

Vitamins and Minerals: Calcium Phosphate Tribasic, Potassium Phosphate Dibasic, Magnesium Oxide, Salt (Sodium Chloride), Potassium Chloride, Ascorbic Acid, Ferric Orthophosphate, Alpha-Tocopheryl Acetate, Niacinamide, Zinc Oxide, Calcium Pantothenate, Copper Gluconate, Manganese Sulfate, Riboflavin, Beta Carotene, Pyridoxine Hydrochloride, Thiamine Mononitrate, Folic Acid, Biotin, Chromium Chloride, Potassium Iodide, Sodium Selenate, Sodium Molybdate, Phylloquinone, Vitamin D3 and Cyanocobalamin.

Protein: Honey Graham Crunch—The protein source is a blend of soy protein isolate and milk proteins.

| | |
|---|---|
| Soy protein isolate | 74% |
| Milk proteins | 26% |

Fat: Honey Graham Crunch—The fat source is a blend of partially hydrogenated cottonseed and soybean, canola, high oleic safflower, oils, and soy lecithin.

| | |
|---|---|
| Partially hydrogenated cottonseed and soybean oil | 76% |
| Canola oil | 8% |
| High-oleic safflower oil | 8% |
| Corn oil | 4% |
| Soy lecithin | 4% |

Carbohydrate: Honey Graham Crunch—The carbohydrate source is a combination of high-fructose corn syrup, brown sugar, maltodextrin, honey, crisp rice, glycerine, soy polysaccharide, and oat bran.

| | |
|---|---|
| High-fructose corn syrup | 24% |
| Brown sugar | 21% |
| Maltodextrin | 12% |
| Honey | 11% |
| Crisp rice | 9% |
| Glycerine | 9% |
| Soy Polysaccharide | 7% |
| Oat bran | 7% |

C. Ensure® High Protein:

Usage: ENSURE HIGH PROTEIN is a concentrated, high-protein liquid food designed for people who require additional calories, protein, vitamins, and minerals in their diets. It can be used as an oral nutritional supplement with or between meals or, in appropriate amounts, as a meal replacement. ENSURE HIGH PROTEIN is lactose- and gluten-free, and is suitable for use by people recovering from general surgery or hip fractures and by patients at risk for pressure ulcers.

Patient Conditions:
  For patients who require additional calories, protein, vitamins, and minerals, such as patients recovering from general surgery or hip fractures, patients at risk for pressure ulcers, and patients on low-cholesterol diets.

Features:
  Low in saturated fat
  Contains 6 g of total fat and <5 mg of cholesterol per serving
  Rich, creamy taste
  Excellent source of protein, calcium, and other essential vitamins and minerals
  For low-cholesterol diets
  Lactose-free, easily digested Ingredients:
  Vanilla Supreme: -D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate, Phylloquinone, Vitamin D3 and Cyanocobalamin.

Protein:
  The protein source is a blend of two high-biologic-value proteins: casein and soy.

| | |
|---|---|
| Sodium and calcium caseinates | 85% |
| Soy protein isolate | 15% |

Fat:

The fat source is a blend of three oils: high-oleic safflower, canola, and soy.

| | |
|---|---|
| High-oleic safflower oil | 40% |
| Canola oil | 30% |
| Soy oil | 30% |

The level of fat in ENSURE HIGH PROTEIN meets American Heart Association (AHA) guidelines. The 6 grams of fat in ENSURE HIGH PROTEIN represent 24% of the total calories, with 2.6% of the fat being from saturated fatty acids and 7.9% from polyunsaturated fatty acids. These values are within the AHA guidelines of <30% of total calories from fat, <10% of the calories from saturated fatty acids, and <10% of total calories from polyunsaturated fatty acids.

Carbohydrate:

ENSURE HIGH PROTEIN contains a combination of maltodextrin and sucrose. The mild sweetness and flavor variety (vanilla supreme, chocolate royal, wild berry, and banana), plus VARI-FLAVORS® Flavor Pacs in pecan, cherry, strawberry, lemon, and orange, help to prevent flavor fatigue and aid in patient compliance.

Vanilla and Other Nonchocolate Flavors:

| | |
|---|---|
| Sucrose | 60% |
| Maltodextrin | 40% |

Chocolate:

| | |
|---|---|
| Sucrose | 70% |
| Maltodextrin | 30% |

D. Ensure® Light

Usage: ENSURE LIGHT is a low-fat liquid food designed for use as an oral nutritional supplement with or between meals. ENSURE LIGHT is lactose- and gluten-free, and is suitable for use in modified diets, including low-cholesterol diets.

Patient Conditions:
  For normal-weight or overweight patients who need extra nutrition in a supplement that contains 50% less fat and 20% fewer calories than ENSURE.
  For healthy adults who do not eat right and need extra nutrition.

Features:
  Low in fat and saturated fat
  Contains 3 g of total fat per serving and <5 mg cholesterol
  Rich, creamy taste
  Excellent source of calcium and other essential vitamins and minerals
  For low-cholesterol diets
  Lactose-free, easily digested Ingredients:
  French Vanilla: -D Water, Maltodextrin (Corn), Sugar (Sucrose), Calcium Caseinate, High-Oleic Safflower Oil, Canola Oil, Magnesium Chloride, Sodium Citrate, Potassium Citrate, Potassium Phosphate Dibasic, Magnesium Phosphate Dibasic, Natural and Artificial Flavor, Calcium Phosphate Tribasic, Cellulose Gel, Choline Chloride, Soy Lecithin, Carrageenan, Salt (Sodium Chloride), Ascorbic Acid, Cellulose Gum, Ferrous Sulfate, Alpha-Tocopheryl Acetate, Zinc Sulfate, Niacinamide, Manganese Sulfate, Calcium Pantothenate, Cupric Sulfate, Thiamine Chloride Hydrochloride, Vitamin A Palmitate, Pyridoxine Hydrochloride, Riboflavin, Chromium Chloride, Folic Acid, Sodium Molybdate, Biotin, Potassium Iodide, Sodium Selenate, Phylloquinone, Vitamin D3 and Cyanocobalamin.

Protein:

The protein source is calcium caseinate.

| | |
|---|---|
| Calcium caseinate | 100% |

Fat:

The fat source is a blend of two oils: high-oleic safflower and canola.

| | |
|---|---|
| High-oleic safflower oil | 70% |
| Canola oil | 30% |

The level of fat in ENSURE LIGHT meets American Heart Association (AHA) guidelines. The 3 grams of fat in ENSURE LIGHT represent 13.5% of the total calories, with 1.4% of the fat being from saturated fatty acids and 2.6% from polyunsaturated fatty acids. These values are within the AHA guidelines of <30% of total calories from fat, <10% of the, calories from saturated fatty acids, and <10% of total calories from polyunsaturated fatty acids.

Carbohydrate:

ENSURE LIGHT contains a combination of maltodextrin and sucrose. The chocolate flavor contains corn syrup as well. The mild sweetness and flavor variety (French vanilla, chocolate supreme, strawberry swirl), plus VARI-FLAVORS® Flavor Pacs in pecan, cherry, strawberry, lemon, and orange, help to prevent flavor fatigue and aid in patient compliance.

Vanilla and Other Nonchocolate Flavors:

| | |
|---|---|
| Sucrose | 51% |
| Maltodextrin | 49% |

Chocolate:

| | |
|---|---|
| Sucrose | 47.0% |
| Corn Syrup | 26.5% |
| Maltodextrin | 26.5% |

Vitamins and Minerals:

An 8-fl-oz serving of ENSURE LIGHT provides at least 25% of the RDIs for 24 key vitamins and minerals.

Caffeine:

Chocolate flavor contains 2.1 mg caffeine/8 fl oz.

E. Ensure Plus®

Usage: ENSURE PLUS is a high-calorie, low-residue liquid food for use when extra calories and nutrients, but a normal concentration of protein, are needed. It is designed primarily as an oral nutritional supplement to be used with or between meals or, in appropriate amounts, as a meal replacement. ENSURE PLUS is lactose- and gluten-free. Although it is primarily an oral nutritional supplement, it can be fed by tube.

Patient Conditions:
  For patients who require extra calories and nutrients, but a normal concentration of protein, in a limited volume.
  For patients who need to gain or maintain healthy weight.
Features:
  Rich, creamy taste
  Good source of essential vitamins and minerals
Ingredients:
  Vanilla: -D Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasic, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.
Protein:
  The protein source is a blend of two high-biologic-value proteins: casein and soy.

| | |
|---|---|
| Sodium and calcium caseinates | 84% |
| Soy protein isolate | 16% |

Fat:
  The fat source is corn oil.

| | |
|---|---|
| Corn oil | 100% |

Carbohydrate:
  ENSURE PLUS contains a combination of maltodextrin and sucrose. The mild sweetness and flavor variety (vanilla, chocolate, strawberry, coffee, buffer pecan, and eggnog), plus VARI-FLAVORS® Flavor Pacs in pecan, cherry, strawberry, lemon, and orange, help to prevent flavor fatigue and aid in patient compliance.
Vanilla, Strawberry, Butter Pecan, and Coffee Flavors:

| | |
|---|---|
| Corn Syrup | 39% |
| Maltodextrin | 38% |
| Sucrose | 23% |

Chocolate and Eggnog Flavors:

| | |
|---|---|
| Corn Syrup | 36% |
| Maltodextrin | 34% |
| Sucrose | 30% |

Vitamins and Minerals:
  An 8-fl-oz serving of ENSURE PLUS provides at least 15% of the RDIs for 25 key Vitamins and minerals.
Caffeine:
  Chocolate flavor contains 3.1 mg Caffeine/8 fl oz. Coffee flavor contains a trace amount of caffeine.
F. Ensure Plus® HN
  Usage: ENSURE PLUS HN is a nutritionally complete high-calorie, high-nitrogen liquid food designed for people with higher calorie and protein needs or limited volume tolerance. It may be used for oral supplementation or for total nutritional support by tube. ENSURE PLUS HN is lactose- and gluten-free.
Patient Conditions:
  For patients with increased calorie and protein needs, such as following surgery or injury.
  For patients with limited volume tolerance and early satiety.
Features:
  For supplemental or total nutrition
  For oral or tube feeding
  1.5 CaVmL,
  High nitrogen
  Calorically dense
Ingredients:
  Vanilla: -D Water, Maltodextrin (Corn), Sodium and Calcium Caseinates, Corn Oil, Sugar (Sucrose), Soy Protein Isolate, Magnesium Chloride, Potassium Citrate, Calcium Phosphate Tribasic, Soy Lecithin, Natural and Artificial Flavor, Sodium Citrate, Choline Chloride, Ascorbic Acid, Taurine, L-Carnitine, Zinc Sulfate, Ferrous Sulfate, Alpha-Tocopheryl Acetate, Niacinamide, Carrageenan, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.
G. Ensure® Powder:
  Usage: ENSURE POWDER (reconstituted with water) is a low-residue
  liquid food designed primarily as an oral nutritional supplement to be used with or between meals. ENSURE POWDER is lactose- and gluten-free, and is suitable for use in modified diets, including low-cholesterol diets.
Patient Conditions:
  For patients on modified diets
  For elderly patients at nutrition risk
  For patients recovering from illness/surgery
  For patients who need a low-residue diet
Features:
  Convenient, easy to mix
  Low in saturated fat
  Contains 9 g of total fat and <5 mg of cholesterol per serving
  High in vitamins and minerals
  For low-cholesterol diets
  Lactose-free, easily digested
  Ingredients: -D Corn Syrup, Maltodextrin (Corn), Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate Tribasic, Potassium Chloride, Soy Lecithin, Ascorbic Acid, Choline Chloride, Zinc Sulfate, Ferrous Sulfate, Alpha-Tocopheryl Acetate, Niacinamide, Calcium Pantothenate, Manganese Sulfate, Thiamine Chloride Hydrochloride, Cupric Sulfate, Pyridoxine Hydrochloride, Riboflavin, Vitamin A Palmitate, Folic Acid, Biotin, Sodium Molybdate, Chromium Chloride, Potassium Iodide, Sodium Selenite, Phylloquinone, Vitamin D3 and Cyanocobalamin.
Protein:
  The protein source is a blend of two high-biologic-value proteins: casein and soy.

| | |
|---|---|
| Sodium and calcium caseinates | 84% |
| Soy protein isolate | 16% |

Fat:
  The fat source is corn oil.

| | |
|---|---|
| Corn oil | 100% |

Carbohydrate:
  ENSURE POWDER contains a combination of corn syrup, maltodextrin, and sucrose. The mild sweetness of ENSURE POWDER, plus VARI-FLAVORS® Flavor Pacs in pecan, cherry, strawberry, lemon, and orange, helps to prevent flavor fatigue and aid in patient compliance.
Vanilla:

| | |
|---|---|
| Corn Syrup | 35% |
| Maltodextrin | 35% |
| Sucrose | 30% |

H. Ensure® Pudding
  Usage: ENSURE PUDDING is a nutrient-dense supplement providing balanced nutrition in a nonliquid form to be used with or between meals. It is appropriate for consistency-modified diets (e.g., soft, pureed, or full liquid) or for people with swallowing impairments. ENSURE PUDDING is gluten-free.
Patient Conditions:
  For patients on consistency-modified diets (e.g., soft, pureed, or full liquid)
  For patients with swallowing impairments
Features:
  Rich and creamy, good taste
  Good source of essential vitamins and minerals
  Convenient-needs no refrigeration
  Gluten-free
  Nutrient Profile per 5 oz: Calories 250, Protein 1-0.9%, Total Fat 34.9%, Carbohydrate 54.2%
Ingredients:
  Vanilla: -D Nonfat Milk, Water, Sugar (Sucrose), Partially Hydrogenated Soybean Oil, Modified Food Starch, Magnesium Sulfate, Sodium Stearoyl Lactylate, Sodium Phosphate Dibasic, Artificial Flavor, Ascorbic Acid, Zinc Sulfate, Ferrous Sulfate, Alpha-Tocopheryl Acetate, Choline Chloride, Niacinamide, Manganese Sulfate, Calcium Pantothenate, FD&C Yellow #5, Potassium Citrate, Cupric Sulfate, Vitamin A Palmitate, Thiamine Chloride Hydrochloride, Pyridoxine Hydrochloride, Riboflavin, FD&C Yellow #6, Folic Acid, Biotin, Phylloquinone, Vitamin D3 and Cyanocobalamin.
Protein:
  The protein source is nonfat milk.

| | |
|---|---|
| Nonfat milk | 100% |

Fat:
  The fat source is hydrogenated soybean oil.

| | |
|---|---|
| Hydrogenated soybean oil | 100% |

Carbohydrate:
  ENSURE PUDDING contains a combination of sucrose and modified food starch. The mild sweetness and flavor variety (vanilla, chocolate, butterscotch, and tapioca) help prevent flavor fatigue. The product contains 9.2 grams of lactose per serving.
Vanilla and Other Nonchocolate Flavors:

| | |
|---|---|
| Sucrose | 56% |
| Lactose | 27% |
| Modified food starch | 17% |

Chocolate:

| | |
|---|---|
| Sucrose | 58% |
| Lactose | 26% |
| Modified food starch | 16% |

I. Ensure® with Fiber:
  Usage: ENSURE WITH FIBER is a fiber-containing, nutritionally complete liquid food designed for people who can benefit from increased dietary fiber and nutrients. ENSURE WITH FIBER is suitable for people who do not require a low-residue diet. It can be fed orally or by tube, and can be used as a nutritional supplement to a regular diet or, in appropriate amounts, as a meal replacement. ENSURE WITH FIBER is lactose- and gluten-free, and is suitable for use in modified diets, including low-cholesterol diets.
Patient Conditions:
  For patients who can benefit from increased dietary fiber and nutrients
Features:
  New advanced formula-low in saturated fat, higher in vitamins and minerals
  Contains 6 g of total fat and <5 mg of cholesterol per serving
  Rich, creamy taste
  Good source of fiber
  Excellent source of essential vitamins and minerals
  For low-cholesterol diets
  Lactose- and gluten-free
Ingredients:
  Vanilla: -D Water; Maltodextrin (Corn), Sugar (Sucrose), Sodium and Calcium Caseinates, Oat Fiber, High-Oleic Safflower Oil, Canola Oil, Soy Protein Isolate, Corn Oil, Soy Fiber, Calcium Phosphate Tribasic, Magnesium Chloride, Potassium Citrate, Cellulose Gel, Soy Lecithin, Potassium Phosphate Dibasic, Sodium Citrate, Natural and Artificial Flavors, Choline Chloride, Magnesium Phosphate, Ascorbic Acid, Cellulose Gum, Potassium Chloride, Carrageenan, Ferrous Sulfate, Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.
Protein:
  The protein source is a blend of two high-biologic-value proteins-casein and soy.

| | |
|---|---|
| Sodium and calcium caseinates | 80% |
| Soy protein isolate | 20% |

Fat:

The fat source is a blend of three oils: high-oleic safflower, canola, and corn.

| | |
|---|---|
| High-oleic safflower oil | 40% |
| Canola oil | 40% |
| Corn oil | 20% |

The level of fat in ENSURE WITH FIBER meets American Heart Association (AHA) guidelines. The 6 grams of fat in ENSURE WITH FIBER represent 22% of the total calories, with 2.01% of the fat being from saturated fatty acids and 6.7% from polyunsaturated fatty acids. These values are within the AHA guidelines of ≦30% of total calories from fat, ≦10% of the calories from saturated fatty acids, and ≦10% of total calories from polyunsaturated fatty acids.

Carbohydrate:

ENSURE WITH FIBER contains a combination of maltodextrin and sucrose. The mild sweetness and flavor variety (vanilla, chocolate, and butter pecan), plus VARI-FLAVORS® Flavor Pacs in pecan, cherry, strawberry, lemon, and orange, help to prevent flavor fatigue and aid in patient compliance.

Vanilla and Other Nonchocolate Flavors:

| | |
|---|---|
| Maltodextrin | 66% |
| Sucrose | 25% |
| Oat Fiber | 7% |
| Soy Fiber | 2% |

Chocolate:

| | |
|---|---|
| Maltodextrin | 55% |
| Sucrose | 36% |
| Oat Fiber | 7% |
| Soy Fiber | 2% |

Fiber:

The fiber blend used in ENSURE WITH FIBER consists of oat fiber and soy polysaccharide. This blend results in approximately 4 grams of total dietary fiber per 8-fl. oz can. The ratio of insoluble to soluble fiber is 95:5.

The various nutritional supplements described above and known to others of skill in the art can be substituted and/or supplemented with the PUFAs produced in accordance with the present invention.

J. Oxepa™ Nutritional Product

Oxepa is a low-carbohydrate, calorically dense, enteral nutritional product designed for the dietary management of patients with or at risk for ARDS. It has a unique combination of ingredients, including a patented oil blend containing eicosapentaenoic acid (EPA from fish oil), γ-linolenic acid (GLA from borage oil), and elevated antioxidant levels.

Caloric Distribution:

Caloric density is high at 1.5 Cal/mL (355 Cal/8 fl oz), to minimize the volume required to meet energy needs. The distribution of Calories in Oxepa is shown in Table A.

TABLE A

Caloric Distribution of Oxepa

| | per 8 fl oz. | per liter | % of Cal |
|---|---|---|---|
| Calories | 355 | 1,500 | — |
| Fat (g) | 22.2 | 93.7 | 55.2 |
| Carbohydrate (g) | 25 | 105.5 | 28.1 |
| Protein (g) | 14.8 | 62.5 | 16.7 |
| Water (g) | 186 | 785 | — |

Fat:

Oxepa contains 22.2 g of fat per 8-fl oz serving (93.7 g/L).

The fat source is an oil blend of 31.8% canola oil, 25% medium-chain triglycerides (MCTs), 20% borage oil, 20% fish oil, and 3.2% soy lecithin. The typical fatty acid profile of Oxepa is shown in Table B.

Oxepa provides a balanced amount of polyunsaturated, monounsaturated, and saturated fatty acids, as shown in Table VI.

Medium-chain trigylcerides (MCTs)—25% of the fat blend—aid gastric emptying because they are absorbed by the intestinal tract without emulsification by bile acids.

The various fatty acid components of Oxepa™ nutritional product can be substituted and/or supplemented with the PUFAs produced in accordance with this invention.

TABLE B

Typical Fatty Acid Profile

| Fatty Acids | % Total | g/8 fl oz* | 9/L* |
|---|---|---|---|
| Caproic (6:0) | 0.2 | 0.04 | 0.18 |
| Caprylic (8:0) | 14.69 | 3.1 | 13.07 |
| Capric (10:0) | 11.06 | 2.33 | 9.87 |
| Palmitic (16:0) | 5.59 | 1.18 | 4.98 |
| Palmitoleic | 1.82 | 0.38 | 1.62 |
| Stearic | 1.94 | 0.39 | 1.64 |
| Oleic | 24.44 | 5.16 | 21.75 |
| Linoleic | 16.28 | 3.44 | 14.49 |
| α-Linolenic | 3.47 | 0.73 | 3.09 |
| γ-Linolenic | 4.82 | 1.02 | 4.29 |
| Eicosapentaenoic | 5.11 | 1.08 | 4.55 |
| n-3-Docosapentaenoic | 0.55 | 0.12 | 0.49 |
| Docosahexaenoic | 2.27 | 0.48 | 2.02 |
| Others | 7.55 | 1.52 | 6.72 |

Fatty acids equal approximately 95% of total fat.

TABLE C

Fat Profile of Oxepa

| | |
|---|---|
| % of total calories from fat | 55.2 |
| Polyunsaturated fatty acids | 31.44 g/L |
| Monounsaturated fatty acids | 25.53 g/L |
| Saturated fatty acids | 32.38 g/L |
| n-6 to n-3 ratio | 1.75:1 |
| Cholesterol | 9.49 mg/8 fl oz |
| | 40.1 mg/L |

Carbohydrate:

The carbohydrate content is 25.0 g per 8-fl-oz serving (105.5 g/L).

The carbohydrate sources are 45% maltodextrin (a complex carbohydrate) and 55% sucrose (a simple sugar), both of which are readily digested and absorbed.

The high-fat and low-carbohydrate content of Oxepa is designed to minimize carbon dioxide ($CO_2$) production.

High CO2 levels can complicate weaning in ventilator-dependent patients. The low level of carbohydrate also may be useful for those patients who have developed stress-induced hyperglycemia.

Oxepa is lactose-free.

Dietary carbohydrate, the amino acids from protein, and the glycerol moiety of fats can be converted to glucose within the body. Throughout this process, the carbohydrate requirements of glucose-dependent tissues (such as the central nervous system and red blood cells) are met. However, a diet free of carbohydrates can lead to ketosis, excessive catabolism of tissue protein, and loss of fluid and electrolytes. These effects can be prevented by daily ingestion of 50 to 100 g of digestible carbohydrate, if caloric intake is adequate. The carbohydrate level in Oxepa is also sufficient to minimize gluconeogenesis, if energy needs are being met.

Protein:

Oxepa contains 14.8 g of protein per 8-fl-oz serving (62.5 g/L).

The total calorie/nitrogen ratio (150:1) meets the need of stressed patients.

Oxepa provides enough protein to promote anabolism and the maintenance of lean body mass without precipitating respiratory problems. High protein intakes are a concern in patients with respiratory insufficiency. Although protein has little effect on CO2 production, a high protein diet will increase ventilatory drive.

The protein sources of Oxepa are 86.8% sodium caseinate and 13.2% calcium caseinate.

The amino acid profile of the protein system in Oxepa meets or surpasses the standard for high quality protein set by the National Academy of Sciences.

Oxepa is gluten-free.

What is claimed is:

1. An isolated nucleotide sequence comprising or complementary to a nucleotide sequence encoding a polypeptide having omega-3 desaturase activity, wherein the amino acid sequence of said polypeptide has at least 95% sequence identity to SEQ ID NO:26.

2. An isolated nucleotide sequence encoding a polypeptide having omega-3 desaturase activity, the nucleotide sequence comprising or complementary to at least 95% of the nucleotide sequence of SEQ ID NO:25.

3. The isolated nucleotide sequence of claim 2, wherein said sequence is SEQ ID NO:25.

4. The isolated nucleotide sequence of claim 2 or 3, wherein said sequence encodes a functionally active omega-3 desaturase which utilizes a polyunsaturated fatty acid as a substrate.

5. The isolated nucleotide sequence of claim 1 or 2, wherein said sequence is derived from *Saprolegnia diclina*.

6. A method of producing a desaturase comprising the steps of:
  (a) isolating a nucleotide sequence encoding a polypeptide having omega-3 desaturase activity, said nucleotide sequence comprising or complementary to at least 95% of the nucleotide sequence of SEQ ID NO: 25;
  (b) constructing a vector comprising said isolated nucleotide sequence of step (a); and
  (c) introducing said vector of step (b) into a host cell for a time and under conditions sufficient for expression of an omega-3 desaturase encoded by said isolated nucleotide sequence of step (a).

7. A vector comprising: 1) an isolated nucleotide sequence encoding a polypeptide having omega-3 desaturase activity, said nucleotide sequence corresponding to or complementary to at least 95% of the nucleotide sequence of SEQ ID NO: 25, operably linked to b) a regulatory sequence.

8. A host cell comprising said vector of claim claim 7.

9. The host cell of claim 8, wherein said host cell is a eukaryotic cell selected from the group consisting of a mammalian cell, an insect cell, a plant cell and a fungal cell.

10. The host cell of claim 9, wherein expression of said isolated nucleotide sequence of said vector results in said host cell producing a polyunsaturated fatty acid that is not produced in a wild-type of said host cell.

11. A plant cell, plant, or plant tissue comprising said vector of claim 7, wherein expression of said nucleotide sequence of said vector results in production of a polyunsaturated fatty acid by said plant cell, plant or plant tissue.

12. The plant cell, plant, or plant tissue of claim 11, wherein said vector induces the production of a polyunsaturated fatty acid selected from the group consisting of linoleic acid, eicosatetraenoic acid and eicosapentaenoic acid.

13. A transgenic plant comprising said vector of claim 7, wherein expression of said nucleotide sequence of said vector results in production of a polyunsaturated fatty acid in seeds of said transgenic plant.

14. A method for producing a polyunsaturated fatty acid comprising the steps of:
  (a) isolating a nucleotide sequence encoding a polypeptide having omega-3 desaturase activity, said nucleotide sequence comprising or complementary to at least 95% of the nucleotide sequence of SEQ ID NO: 25;
  (b) constructing a vector comprising said isolated nucleotide sequence of step (a);
  (c) transforming the vector of step (b) into a host cell for a time and under conditions sufficient for expression of an omega-3 desaturase encoded by said isolated nucleotide sequence of step (a); and
  (d) exposing said expressed omega-3-desaturase, to a fatty acid substrate, whereby said substrate is catalytically converted by said omega-3 desaturase into a desired polyunsaturated fatty acid product.

15. The method of claim 14, wherein the fatty acid substrate is dihomo-gamma-linolenic acid or arachidonic acid and said product polyunsaturated fatty acid is eicosatetraenoic acid or eicosapentaenoic acid, respectively, when said polypeptide is an omega 3-desaturase.

* * * * *

SEQUENCE LISTING

```
<160> NUMBER OF SEQ ID NOS: 60

<210> SEQ ID NO 1
<211> LENGTH: 36
<212> TYPE: DNA
<213> ORGANISM: Artificial Sequence
<220> FEATURE:
<223> OTHER INFORMATION: Forward Primer RO1144

<400> SEQUENCE: 1
atccgcgccg ccatccccaa gcactgctgg gtcaag                              36

<210> SEQ ID NO 2
<211> LENGTH: 45
<212> TYPE: DNA
<213> ORGANISM: Artificial Sequence
<220> FEATURE:
<223> OTHER INFORMATION: Forward Primer RO1119
<220> FEATURE:
<221> NAME/KEY: misc_feature
<222> LOCATION: (21)...(21)
<223> OTHER INFORMATION: y = t/u or c at position 21
<220> FEATURE:
<221> NAME/KEY: misc_feature
<222> LOCATION: (33)...(33)
<223> OTHER INFORMATION: y = t/u or c at position 33

<400> SEQUENCE: 2
gccctcttcg tcctcggcca ygactgcggc cayggctcgt tctcg                    45

<210> SEQ ID NO 3
<211> LENGTH: 45
<212> TYPE: DNA
<213> ORGANISM: Artificial Sequence
<220> FEATURE:
<223> OTHER INFORMATION: Reverse Primer RO1118
<220> FEATURE:
<221> NAME/KEY: misc_feature
<222> LOCATION: (4)...(4)
<223> OTHER INFORMATION: r = g or a at position 4
<220> FEATURE:
<221> NAME/KEY: misc_feature
<222> LOCATION: (10)...(10)
<223> OTHER INFORMATION: r = g or a at position 10
<220> FEATURE:
<221> NAME/KEY: misc_feature
<222> LOCATION: (30)...(31)
<223> OTHER INFORMATION: r = g or a at positions 30-31
<220> FEATURE:
<221> NAME/KEY: misc_feature
<222> LOCATION: (34)...(34)
```

-continued

```
<223> OTHER INFORMATION: r = g or a at position 34
<220> FEATURE:
<221> NAME/KEY: misc_feature
<222> LOCATION: (38)...(38)
<223> OTHER INFORMATION: r = g or a at poisition 38
<220> FEATURE:
<221> NAME/KEY: misc_feature
<222> LOCATION: (39)...(39)
<223> OTHER INFORMATION: y = t/u or c at position 39
<220> FEATURE:
<221> NAME/KEY: misc_feature
<222> LOCATION: (43)...(43)
<223> OTHER INFORMATION: r = g or a at position 43

<400> SEQUENCE: 3
gagrtggtar tgggggatct gggggaagar rtgrtggryg acrtg                45

<210> SEQ ID NO 4
<211> LENGTH: 45
<212> TYPE: DNA
<213> ORGANISM: Artificial Sequence
<220> FEATURE:
<223> OTHER INFORMATION: Forward Primer RO1121
<220> FEATURE:
<221> NAME/KEY: misc_feature
<222> LOCATION: (9)...(9)
<223> OTHER INFORMATION: y = t/u or c at position 9
<220> FEATURE:
<221> NAME/KEY: misc_feature
<222> LOCATION: (27)...(27)
<223> OTHER INFORMATION: y = t/u or c at position 27
<220> FEATURE:
<221> NAME/KEY: misc_feature
<222> LOCATION: (36)...(36)
<223> OTHER INFORMATION: y = t/u or c at position 36
<220> FEATURE:
<221> NAME/KEY: misc_feature
<222> LOCATION: (39)...(39)
<223> OTHER INFORMATION: y = t/u or c at position 39

<400> SEQUENCE: 4
ccctaccayg gctggcgcat ctcgcaycgc acccaycayc agaac                45

<210> SEQ ID NO 5
<211> LENGTH: 45
<212> TYPE: DNA
<213> ORGANISM: Artificial Sequence
<220> FEATURE:
<223> OTHER INFORMATION: Reverse Primer RO1122
<220> FEATURE:
<221> NAME/KEY: misc_feature
<222> LOCATION: (7)...(7)
<223> OTHER INFORMATION: r = g or a at position 7
<220> FEATURE:
<221> NAME/KEY: misc_feature
<222> LOCATION: (10)...(10)
<223> OTHER INFORMATION: r = g or a at position 10
<220> FEATURE:
<221> NAME/KEY: misc_feature
<222> LOCATION: (37)...(37)
<223> OTHER INFORMATION: r = g or a at position 37

<400> SEQUENCE: 5
gttctgrtgr tgggtccgrt gcgagatgcg ccagccrtgg taggg                45

<210> SEQ ID NO 6
<211> LENGTH: 36
<212> TYPE: DNA
<213> ORGANISM: Artificial Sequence
<220> FEATURE:
<223> OTHER INFORMATION: Forward Primer RO1146
<220> FEATURE:
<221> NAME/KEY: misc_feature
<222> LOCATION: (13)...(13)
```

```
<223> OTHER INFORMATION: s = g or c at position 13
<220> FEATURE:
<221> NAME/KEY: misc_feature
<222> LOCATION: (19)...(19)
<223> OTHER INFORMATION: k = g or t/u at position 19

<400> SEQUENCE: 6
ggctcgcact tcsaccccka ctcggacctc ttcgtc                                   36

<210> SEQ ID NO 7
<211> LENGTH: 36
<212> TYPE: DNA
<213> ORGANISM: Artificial Sequence
<220> FEATURE:
<223> OTHER INFORMATION: Reverse Primer RO1147
<220> FEATURE:
<221> NAME/KEY: misc_feature
<222> LOCATION: (18)...(18)
<223> OTHER INFORMATION: m = a or c at position 18
<220> FEATURE:
<221> NAME/KEY: misc_feature
<222> LOCATION: (24)...(24)
<223> OTHER INFORMATION: w = a or t/u at position 24

<400> SEQUENCE: 7
gacgaagagg tccgagtmgg ggtwgaagtg cgagcc                                   36

<210> SEQ ID NO 8
<211> LENGTH: 39
<212> TYPE: DNA
<213> ORGANISM: Artificial Sequence
<220> FEATURE:
<223> OTHER INFORMATION: Reverse Primer RO1148
<220> FEATURE:
<221> NAME/KEY: misc_feature
<222> LOCATION: (9)...(9)
<223> OTHER INFORMATION: k = g or t/u at position 9
<220> FEATURE:
<221> NAME/KEY: misc_feature
<222> LOCATION: (30)...(30)
<223> OTHER INFORMATION: w = a or t/u at position 30
<220> FEATURE:
<221> NAME/KEY: misc_feature
<222> LOCATION: (32)...(32)
<223> OTHER INFORMATION: s = g or c at position 32

<400> SEQUENCE: 8
gcgctggakg gtggtgaggc cgccgcggaw gsacgacca                                39

<210> SEQ ID NO 9
<211> LENGTH: 45
<212> TYPE: DNA
<213> ORGANISM: Artificial Sequence
<220> FEATURE:
<223> OTHER INFORMATION: Reverse Primer RO1114
<220> FEATURE:
<221> NAME/KEY: misc_feature
<222> LOCATION: (13)...(13)
<223> OTHER INFORMATION: r = g or a at position 13
<220> FEATURE:
<221> NAME/KEY: misc_feature
<222> LOCATION: (16)...(16)
<223> OTHER INFORMATION: r = g or a at position 16
<220> FEATURE:
<221> NAME/KEY: misc_feature
<222> LOCATION: (25)...(25)
<223> OTHER INFORMATION: r = g or a at position 25
<220> FEATURE:
<221> NAME/KEY: misc_feature
<222> LOCATION: (40)...(40)
<223> OTHER INFORMATION: r = g or a at position 40
<220> FEATURE:
<221> NAME/KEY: misc_feature
<222> LOCATION: (43)...(43)
```

```
<223> OTHER INFORMATION: r = g or a at position 43

<400> SEQUENCE: 9
ctgggggaag agrtgrtgga tgacrtgggt gccgatgtcr tgrtg                    45

<210> SEQ ID NO 10
<211> LENGTH: 45
<212> TYPE: DNA
<213> ORGANISM: Artificial Sequence
<220> FEATURE:
<223> OTHER INFORMATION: Reverse Primer RO1116
<220> FEATURE:
<221> NAME/KEY: misc_feature
<222> LOCATION: (12)...(12)
<223> OTHER INFORMATION: y = t/u or c at position 12
<220> FEATURE:
<221> NAME/KEY: misc_feature
<222> LOCATION: (16)...(16)
<223> OTHER INFORMATION: r = g or a at position 16
<220> FEATURE:
<221> NAME/KEY: misc_feature
<222> LOCATION: (22)...(22)
<223> OTHER INFORMATION: r = g or a at position 22
<220> FEATURE:
<221> NAME/KEY: misc_feature
<222> LOCATION: (33)...(33)
<223> OTHER INFORMATION: k = g or t/u at position 33
<220> FEATURE:
<221> NAME/KEY: misc_feature
<222> LOCATION: (42)...(43)
<223> OTHER INFORMATION: r = g or at at positions 42-43

<400> SEQUENCE: 10
ggtggcctcg aygagrtggt artgggggat ctkggggaag arrtg                   45

<210> SEQ ID NO 11
<211> LENGTH: 45
<212> TYPE: DNA
<213> ORGANISM: Artificial Sequence
<220> FEATURE:
<223> OTHER INFORMATION: Reverse Primer RO1118
<220> FEATURE:
<221> NAME/KEY: misc_feature
<222> LOCATION: (4)...(4)
<223> OTHER INFORMATION: r = g or a at position 4
<220> FEATURE:
<221> NAME/KEY: misc_feature
<222> LOCATION: (10)...(10)
<223> OTHER INFORMATION: r = g or a at position 10
<220> FEATURE:
<221> NAME/KEY: misc_feature
<222> LOCATION: (30)...(31)
<223> OTHER INFORMATION: r = g or a at positions 30-31
<220> FEATURE:
<221> NAME/KEY: misc_feature
<222> LOCATION: (34)...(34)
<223> OTHER INFORMATION: r = g or a at position 34
<220> FEATURE:
<221> NAME/KEY: misc_feature
<222> LOCATION: (38)...(38)
<223> OTHER INFORMATION: r = g or a at position 38
<220> FEATURE:
<221> NAME/KEY: misc_feature
<222> LOCATION: (39)...(39)
<223> OTHER INFORMATION: y = t/u or c at position 39
<220> FEATURE:
<221> NAME/KEY: misc_feature
<222> LOCATION: (43)...(43)
<223> OTHER INFORMATION: r = g or a at position 43

<400> SEQUENCE: 11
gagrtggtar tgggggatct gggggaagar rtgrtggryg acrtg                   45

<210> SEQ ID NO 12
```

```
<211> LENGTH: 25
<212> TYPE: DNA
<213> ORGANISM: Artificial Sequence
<220> FEATURE:
<223> OTHER INFORMATION: Forward Primer RO1188

<400> SEQUENCE: 12
tacgcgtacc tcacgtactc gctcg                                          25

<210> SEQ ID NO 13
<211> LENGTH: 27
<212> TYPE: DNA
<213> ORGANISM: Artificial Sequence
<220> FEATURE:
<223> OTHER INFORMATION: Forward Primer RO1189

<400> SEQUENCE: 13
ttcttgcacc acaacgacga agcgacg                                        27

<210> SEQ ID NO 14
<211> LENGTH: 25
<212> TYPE: DNA
<213> ORGANISM: Artificial Sequence
<220> FEATURE:
<223> OTHER INFORMATION: Forward Primer RO1190

<400> SEQUENCE: 14
ggagtggacg tacgtcaagg gcaac                                          25

<210> SEQ ID NO 15
<211> LENGTH: 26
<212> TYPE: DNA
<213> ORGANISM: Artificial Sequence
<220> FEATURE:
<223> OTHER INFORMATION: Forward Primer RO1191

<400> SEQUENCE: 15
tcaagggcaa cctctcgagc gtcgac                                         26

<210> SEQ ID NO 16
<211> LENGTH: 31
<212> TYPE: DNA
<213> ORGANISM: Artificial Sequence
<220> FEATURE:
<223> OTHER INFORMATION: Primer RO898

<400> SEQUENCE: 16
cccagtcacg acgttgtaaa acgacggcca g                                   31

<210> SEQ ID NO 17
<211> LENGTH: 30
<212> TYPE: DNA
<213> ORGANISM: Artificial Sequence
<220> FEATURE:
<223> OTHER INFORMATION: Primer RO899

<400> SEQUENCE: 17
agcggataac aatttcacac aggaaacagc                                     30

<210> SEQ ID NO 18
<211> LENGTH: 30
<212> TYPE: DNA
<213> ORGANISM: Artificial Sequence
<220> FEATURE:
<223> OTHER INFORMATION: Reverse Primer RO1185

<400> SEQUENCE: 18
```

```
ggtaaaagat ctcgtccttg tcgatgttgc                                       30

<210> SEQ ID NO 19
<211> LENGTH: 20
<212> TYPE: DNA
<213> ORGANISM: Artificial Sequence
<220> FEATURE:
<223> OTHER INFORMATION: Reverse Primer RO1186

<400> SEQUENCE: 19
gtcaaagtgg ctcatcgtgc                                                  20

<210> SEQ ID NO 20
<211> LENGTH: 26
<212> TYPE: DNA
<213> ORGANISM: Artificial Sequence
<220> FEATURE:
<223> OTHER INFORMATION: Reverse Primer RO1187

<400> SEQUENCE: 20
cgagcgagta cgtgaggtac gcgtac                                           26

<210> SEQ ID NO 21
<211> LENGTH: 45
<212> TYPE: DNA
<213> ORGANISM: Artificial Sequence
<220> FEATURE:
<223> OTHER INFORMATION: Forward Primer RO1212

<400> SEQUENCE: 21
tcaacagaat tcatgaccga ggataagacg aaggtcgagt tcccg                      45

<210> SEQ ID NO 22
<211> LENGTH: 45
<212> TYPE: DNA
<213> ORGANISM: Artificial Sequence
<220> FEATURE:
<223> OTHER INFORMATION: Reverse Primer RO1213

<400> SEQUENCE: 22
aaaagaaagc ttcgcttcct agtcttagtc cgacttggcc ttggc                      45

<210> SEQ ID NO 23
<211> LENGTH: 45
<212> TYPE: DNA
<213> ORGANISM: Artificial Sequence
<220> FEATURE:
<223> OTHER INFORMATION: Forward Primer RO1221

<400> SEQUENCE: 23
tcaacaaagc ttatgaccga ggataagacg aaggtcgagt tcccg                      45

<210> SEQ ID NO 24
<211> LENGTH: 45
<212> TYPE: DNA
<213> ORGANISM: Artificial Sequence
<220> FEATURE:
<223> OTHER INFORMATION: Reverse Primer RO1222

<400> SEQUENCE: 24
aaaagagaat tccgcttcct agtcttagtc cgacttggcc ttggc                      45

<210> SEQ ID NO 25
<211> LENGTH: 1077
<212> TYPE: DNA
<213> ORGANISM: Saprolegnia diclina
```

<400> SEQUENCE: 25

```
atgactgagg ataagacgaa ggtcgagttc ccgacgctca cggagctcaa gcactcgatc      60
ccgaacgcgt gctttgagtc gaacctcggc ctctcgctct actacacggc ccgcgcgatc    120
ttcaacgcgt cggcctcggc ggcgctgctc tacgcggcgc gctcgacgcc gttcattgcc    180
gataacgttc tgctccacgc gctcgtttgc gccacctaca tctacgtgca gggcgtcatc    240
ttctggggct tcttcacggt cggccacgac tgcggccact cggccttctc cgctaccac     300
agcgtcaact ttatcatcgg ctgcatcatg cactctgcga ttttgacgcc gttcgagagc    360
tggcgcgtga cgcaccgcca ccaccacaag aacacgggca acattgataa ggacgagatc    420
ttttacccgc accggtcggt caaggacctc caggacgtgc gccaatgggt ctacacgctc    480
ggcggtgcgt ggtttgtcta cttgaaggtc gggtatgccc cgcgcacgat gagccacttt    540
gacccgtggg acccgctcct ccttcgccgc cgtcggccg tcatcgtgtc gctcggcgtc    600
tgggccgcct cttcgccgc gtacgcgtac ctcacatact cgctcggctt tgccgtcatg    660
ggcctctact actatgcgcc gctctttgtc tttgcttcgt tcctcgtcat tacgaccttc    720
ttgcaccaca cgacgaagc gacgccgtgg tacggcgact cggagtggac gtacgtcaag    780
ggcaacctct cgagcgtcga ccgctcgtac ggcgcgttcg tggacaacct gagccaccac    840
attggcacgc accaggtcca ccacttgttc ccgatcattc cgcactacaa gctcaacgaa    900
gccaccaagc actttgcggc cgcgtacccg cacctcgtgc gcaggaacga cgagcccatc    960
atcacggcct tcttcaagac cgcgcaccct ctttgtcaact acggcgctgt gcccgagacg   1020
gcgcagatct tcacgctcaa agagtcggcc gcggccgcca aggccaagtc ggactaa       1077
```

<210> SEQ ID NO 26
<211> LENGTH: 358
<212> TYPE: PRT
<213> ORGANISM: Saprolegnia diclina

<400> SEQUENCE: 26

```
Met Thr Glu Asp Lys Thr Lys Val Glu Phe Pro Thr Leu Thr Glu Leu
  1               5                  10                  15

Lys His Ser Ile Pro Asn Ala Cys Phe Glu Ser Asn Leu Gly Leu Ser
             20                  25                  30

Leu Tyr Tyr Thr Ala Arg Ala Ile Phe Asn Ala Ser Ala Ser Ala Ala
         35                  40                  45

Leu Leu Tyr Ala Ala Arg Ser Thr Pro Phe Ile Ala Asp Asn Val Leu
     50                  55                  60

Leu His Ala Leu Val Cys Ala Thr Tyr Ile Tyr Val Gln Gly Val Ile
 65                  70                  75                  80

Phe Trp Gly Phe Phe Thr Val Gly His Asp Cys Gly His Ser Ala Phe
                 85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
```

```
                      180                 185                 190
Ala Val Ile Val Ser Leu Gly Val Trp Ala Ala Phe Phe Ala Ala Tyr
        195                 200                 205

Ala Tyr Leu Thr Tyr Ser Leu Gly Phe Ala Val Met Gly Leu Tyr Tyr
        210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His His Ile Gly Thr His Gln Val His His
        275                 280                 285

Leu Phe Pro Ile Ile Pro His Tyr Lys Leu Asn Glu Ala Thr Lys His
        290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
            340                 345                 350

Ala Lys Ala Lys Ser Asp
        355

<210> SEQ ID NO 27
<211> LENGTH: 1413
<212> TYPE: DNA
<213> ORGANISM: Saprolegnia diclina

<400> SEQUENCE: 27
atggccccgc agacggagct ccgccagcgc cacgccgccg tcgccgagac gccggtggcc      60
ggcaagaagg cctttacatg gcaggaggtc gcgcagcaca cacggcggc ctcggcctgg     120 atcattatcc gcggcaaggt ctacgacgtg accgagtggg ccaacaagca ccccggcggc     180
cgcgagatgg tgctgctgca cgccggtcgc gaggccaccg acacgttcga ctcgtaccac     240
ccgttcagcg acaaggccga gtcgatcttg aacaagtatg agattggcac gttcacgggc     300
ccgtccgagt ttccgacctt caagccggac acgggcttct acaaggagtg ccgcaagcgc     360
gttggcgagt acttcaagaa gaacaacctc atccgcagg acggcttccc gggcctctgg     420
cgcatgatgg tcgtgtttgc ggtcgccggc ctcgccttgt acggcatgca cttttcgact     480
atctttgcgc tgcagctcgc ggccgcggcg ctctttggcg tctgccaggc gctgccgctg     540
ctccacgtca tgcacgactc gtcgcacgcg tcgtacacca acatgccgtt cttccattac     600
gtcgtcggcc gctttgccat ggactggttt gccggcggct cgatggtgtc atggctcaac     660
cagcacgtcg tgggccacca catctacacg aacgtcgcgg gctcggaccc ggatcttccg     720
gtcaacatgg acggcgacat ccgccgcatc gtgaaccgcc aggtgttcca gcccatgtac     780
gcattccagc acatctacct tccgccgctc tatggcgtgc ttggcctcaa gttccgcatc     840
caggacttca ccgacacgtt cggctcgcac acgaacggcc cgatccgcgt caacccgcac     900
gcgctctcga cgtggatggc catgatcagc tccaagtcgt tctgggcctt ctaccgcgtg     960
taccttccgc ttgccgtgct ccagatgccc atcaagacgt accttgcgat cttcttcctc    1020
gccgagtttg tcacgggctg gtacctgcgc ttcaacttcc aagtaagcca tgtctcgacc    1080
gagtgcggct acccatgcgg cgacgaggcc aagatggcgc tccaggacga gtgggcagtc    1140
```

```
tcgcaggtca agacgtcggt cgactacgcc catggctcgt ggatgacgac gttccttgcc   1200
ggcgcgctca actaccaggt cgtgcaccac ttgttcccca gcgtgtcgca gtaccactac   1260
ccggcgatcg cgcccatcat cgtcgacgtc tgcaaggagt acaacatcaa gtacgccatc   1320
ttgccggact ttacggcggc gttcgttgcc cacttgaagc acctccgcaa catgggccag   1380
cagggcatcg ccgccacgat ccacatgggc taa                                1413

<210> SEQ ID NO 28
<211> LENGTH: 819
<212> TYPE: DNA
<213> ORGANISM: Thraustochytrid sp.

<400> SEQUENCE: 28
atggcaaaca gcagcgtgtg ggatgatgtg gtgggccgcg tggagaccgg cgtggaccag    60
tggatggatg gcgccaagcc gtacgcactc accgatgggc tcccgatgat ggacgtgtcc   120
accatgctgg cattcgaggt gggatacatg gccatgctgc tcttcggcat cccgatcatg   180
aagcagatgg agaagccttt tgagctcaag accatcaagc tcttgcacaa cttgtttctc   240
ttcggacttt ccttgtacat gtgcgtggag accatccgcc aggctatcct cggaggctac   300
aaagtgtttg aaacgacat ggagaagggc aacgagtctc atgctcaggg catgtctcgc   360
atcgtgtacg tgttctgcgt gtccaaggca tacgagttct ggataccgc catcatgatc   420 ctttgcaaga gttcaacca ggtttccttc ttgcatgtgt accaccatgc caccattttt   480
gccatctggt gggctatcgc caagtacgct ccaggaggtg atgcgtactt ttcagtgatc   540
ctcaactctt tcgtgcacac cgtcatgtac gcatactact tcttctcctc ccaagggttc   600
gggttcgtga agccaatcaa gccgtacatc accacccttc agatgaccca gttcatggca   660
atgcttgtgc agtccttgta cgactacctc ttcccatgcg actacccaca ggctcttgtg   720
cagcttcttg gagtgtacat gatcaccttg cttgccctct tcggcaactt ttttgtgcag   780
agctatctta aaaagccaaa aaagagcaag accaactaa                          819

<210> SEQ ID NO 29
<211> LENGTH: 515
<212> TYPE: PRT
<213> ORGANISM: Saprolegnia diclina

<400> SEQUENCE: 29

Met Thr Val Gly Phe Asp Glu Thr Val Thr Met Asp Thr Val Arg Asn
1               5                   10                  15

His Asn Met Pro Asp Asp Ala Trp Cys Ala Ile His Gly Thr Val Tyr
            20                  25                  30

Asp Ile Thr Lys Phe Ser Lys Val His Pro Gly Gly Asp Ile Ile Met
        35                  40                  45

Leu Ala Ala Gly Lys Glu Ala Thr Ile Leu Phe Glu Thr Tyr His Ile
    50                  55                  60

Lys Gly Val Pro Asp Ala Val Leu Arg Lys Tyr Lys Val Gly Lys Leu
65                  70                  75                  80

Pro Gln Gly Lys Lys Gly Glu Thr Ser His Met Pro Thr Gly Leu Asp
                85                  90                  95

Ser Ala Ser Tyr Tyr Ser Trp Asp Ser Glu Phe Tyr Arg Val Leu Arg
            100                 105                 110

Glu Arg Val Ala Lys Lys Leu Ala Glu Pro Gly Leu Met Gln Arg Ala
        115                 120                 125

Arg Met Glu Leu Trp Ala Lys Ala Ile Phe Leu Leu Ala Gly Phe Trp
```

```
                130                 135                 140
Gly Ser Leu Tyr Ala Met Cys Val Leu Asp Pro His Gly Gly Ala Met
145                 150                 155                 160
Val Ala Val Thr Leu Gly Val Phe Ala Phe Val Gly Thr Cys
                165                 170                 175
Ile Gln His Asp Gly Ser His Gly Ala Phe Ser Lys Ser Arg Phe Met
                180                 185                 190
Asn Lys Ala Ala Gly Trp Thr Leu Asp Met Ile Gly Ala Ser Ala Met
                195                 200                 205
Thr Trp Glu Met Gln His Val Leu Gly His His Pro Tyr Thr Asn Leu
210                 215                 220
Ile Glu Met Glu Asn Gly Leu Ala Lys Val Lys Gly Ala Asp Val Asp
225                 230                 235                 240
Pro Lys Lys Val Asp Gln Glu Ser Asp Pro Asp Val Phe Ser Thr Tyr
                245                 250                 255
Pro Met Leu Arg Leu His Pro Trp His Arg Gln Arg Phe Tyr His Lys
                260                 265                 270
Phe Gln His Leu Tyr Ala Pro Leu Ile Phe Gly Phe Met Thr Ile Asn
                275                 280                 285
Lys Val Ile Ser Gln Asp Val Gly Val Val Leu Arg Lys Arg Leu Phe
                290                 295                 300
Gln Ile Asp Ala Asn Cys Arg Tyr Gly Ser Pro Trp Asn Val Ala Arg
305                 310                 315                 320
Phe Trp Ile Met Lys Leu Leu Thr Thr Leu Tyr Met Val Ala Leu Pro
                325                 330                 335
Met Tyr Met Gln Gly Pro Ala Gln Gly Leu Lys Leu Phe Phe Met Ala
                340                 345                 350
His Phe Thr Cys Gly Glu Val Leu Ala Thr Met Phe Ile Val Asn His
                355                 360                 365
Ile Ile Glu Gly Val Ser Tyr Ala Ser Lys Asp Ala Val Lys Gly Val
                370                 375                 380
Met Ala Pro Pro Arg Thr Val His Gly Val Thr Pro Met Gln Val Thr
385                 390                 395                 400
Gln Lys Ala Leu Ser Ala Ala Glu Ser Thr Lys Ser Asp Ala Asp Lys
                405                 410                 415
Thr Thr Met Ile Pro Leu Asn Asp Trp Ala Ala Val Gln Cys Gln Thr
                420                 425                 430
Ser Val Asn Trp Ala Val Gly Ser Trp Phe Trp Asn His Phe Ser Gly
                435                 440                 445
Gly Leu Asn His Gln Ile Glu His His Cys Phe Pro Gln Asn Pro His
                450                 455                 460
Thr Val Asn Val Tyr Ile Ser Gly Ile Val Lys Glu Thr Cys Glu Glu
465                 470                 475                 480
Tyr Gly Val Pro Tyr Gln Ala Glu Ile Ser Leu Phe Ser Ala Tyr Phe
                485                 490                 495
Lys Met Leu Ser His Leu Arg Thr Leu Gly Asn Glu Asp Leu Thr Ala
                500                 505                 510
Trp Ser Thr
        515

<210> SEQ ID NO 30
<211> LENGTH: 51
<212> TYPE: DNA
<213> ORGANISM: Artificial Sequence
<220> FEATURE:
```

```
<223> OTHER INFORMATION: Forward Primer RO967
<220> FEATURE:
<221> NAME/KEY: misc_feature
<222> LOCATION: (4)...(4)
<223> OTHER INFORMATION: s = g or c at position 4
<220> FEATURE:
<221> NAME/KEY: misc_feature
<222> LOCATION: (12)...(12)
<223> OTHER INFORMATION: s = g or c at position 12
<220> FEATURE:
<221> NAME/KEY: misc_feature
<222> LOCATION: (30)...(30)
<223> OTHER INFORMATION: s = g or c at position 30
<220> FEATURE:
<221> NAME/KEY: misc_feature
<222> LOCATION: (31)...(31)
<223> OTHER INFORMATION: k = g or t/u at position 31
<220> FEATURE:
<221> NAME/KEY: misc_feature
<222> LOCATION: (32)...(32)
<223> OTHER INFORMATION: s = g or c at position 32

<400> SEQUENCE: 30
ccgsagttca csatcaagga gatccgcgas kscatcccgg cccactgctt c            51

<210> SEQ ID NO 31
<211> LENGTH: 48
<212> TYPE: DNA
<213> ORGANISM: Artificial Sequence
<220> FEATURE:
<223> OTHER INFORMATION: Reverse Primer RO968
<220> FEATURE:
<221> NAME/KEY: misc_feature
<222> LOCATION: (2)...(2)
<223> OTHER INFORMATION: r = g or a at position 2
<220> FEATURE:
<221> NAME/KEY: misc_feature
<222> LOCATION: (3)...(3)
<223> OTHER INFORMATION: s = g or c at position 3
<220> FEATURE:
<221> NAME/KEY: misc_feature
<222> LOCATION: (12)...(12)
<223> OTHER INFORMATION: k = g or t/u at position 12
<220> FEATURE:
<221> NAME/KEY: misc_feature
<222> LOCATION: (17)...(17)
<223> OTHER INFORMATION: w = a or t/u at position 17
<220> FEATURE:
<221> NAME/KEY: misc_feature
<222> LOCATION: (18)...(18)
<223> OTHER INFORMATION: m = a or c at position 18
<220> FEATURE:
<221> NAME/KEY: misc_feature
<222> LOCATION: (19)...(19)
<223> OTHER INFORMATION: s = g or c at position 19
<220> FEATURE:
<221> NAME/KEY: misc_feature
<222> LOCATION: (41)...(41)
<223> OTHER INFORMATION: w = a or t/u at position 41
<220> FEATURE:
<221> NAME/KEY: misc_feature
<222> LOCATION: (42)...(42)
<223> OTHER INFORMATION: r = g or a at position 42

<400> SEQUENCE: 31
grscttcttg akgtggwmsg tggcctcctc ggcgtggtag wrcggcat              48

<210> SEQ ID NO 32
<211> LENGTH: 45
<212> TYPE: DNA
<213> ORGANISM: Artificial Sequence
<220> FEATURE:
<223> OTHER INFORMATION: Forward Primer RO964
<220> FEATURE:
<221> NAME/KEY: misc_feature
<222> LOCATION: (3)...(4)
```

-continued

```
<223> OTHER INFORMATION: s = g or c at positions 3-4
<220> FEATURE:
<221> NAME/KEY: misc_feature
<222> LOCATION: (25)...(25)
<223> OTHER INFORMATION: r = g or a at position 25
<220> FEATURE:
<221> NAME/KEY: misc_feature
<222> LOCATION: (36)...(36)
<223> OTHER INFORMATION: s = g or c at position 36

<400> SEQUENCE: 32
ccsstctact gggcctgcca gggtrtcgtc ctcacsggtg tctgg          45

<210> SEQ ID NO 33
<211> LENGTH: 45
<212> TYPE: DNA
<213> ORGANISM: Artificial Sequence
<220> FEATURE:
<223> OTHER INFORMATION: Forward Primer RO965
<220> FEATURE:
<221> NAME/KEY: misc_feature
<222> LOCATION: (3)...(4)
<223> OTHER INFORMATION: s = g or c at positions 3-4
<220> FEATURE:
<221> NAME/KEY: misc_feature
<222> LOCATION: (16)...(16)
<223> OTHER INFORMATION: r = g or a at position 16
<220> FEATURE:
<221> NAME/KEY: misc_feature
<222> LOCATION: (17)...(17)
<223> OTHER INFORMATION: y = t/u or c at position 17
<220> FEATURE:
<221> NAME/KEY: misc_feature
<222> LOCATION: (18)...(18)
<223> OTHER INFORMATION: s = g or c at position 18
<220> FEATURE:
<221> NAME/KEY: misc_feature
<222> LOCATION: (25)...(25)
<223> OTHER INFORMATION: r = g or a at position 25
<220> FEATURE:
<221> NAME/KEY: misc_feature
<222> LOCATION: (31)...(31)
<223> OTHER INFORMATION: k = g or t/u at position 31
<220> FEATURE:
<221> NAME/KEY: misc_feature
<222> LOCATION: (33)...(33)
<223> OTHER INFORMATION: y = t/u or c at position 33
<220> FEATURE:
<221> NAME/KEY: misc_feature
<222> LOCATION: (36)...(36)
<223> OTHER INFORMATION: s = g or c at position 36

<400> SEQUENCE: 33
ccsstctact ggatcrysca gggtrtcgtc kgyacsggtg tctgg          45

<210> SEQ ID NO 34
<211> LENGTH: 45
<212> TYPE: DNA
<213> ORGANISM: Artificial Sequence
<220> FEATURE:
<223> OTHER INFORMATION: Reverse Primer RO966
<220> FEATURE:
<221> NAME/KEY: misc_feature
<222> LOCATION: (19)...(19)
<223> OTHER INFORMATION: s = g or c at position 19
<220> FEATURE:
<221> NAME/KEY: misc_feature
<222> LOCATION: (20)...(21)
<223> OTHER INFORMATION: m = a or c at positions 20-21
<220> FEATURE:
<221> NAME/KEY: misc_feature
<222> LOCATION: (30)...(30)
<223> OTHER INFORMATION: r = g or a at position 30

<400> SEQUENCE: 34
```

```
ggcgtggtag tgcggcatsm mcgagaagar gtggtgggcg acgtg          45
```

<210> SEQ ID NO 35
<211> LENGTH: 29
<212> TYPE: DNA
<213> ORGANISM: Artificial Sequence
<220> FEATURE:
<223> OTHER INFORMATION: Forward Primer RO975

<400> SEQUENCE: 35

```
cacgtacctc cagcacacgg acacctacg                            29
```

<210> SEQ ID NO 36
<211> LENGTH: 27
<212> TYPE: DNA
<213> ORGANISM: Artificial Sequence
<220> FEATURE:
<223> OTHER INFORMATION: Forward Primer RO976

<400> SEQUENCE: 36

```
gatcgacagc gcgatccacc acattgc                              27
```

<210> SEQ ID NO 37
<211> LENGTH: 29
<212> TYPE: DNA
<213> ORGANISM: Artificial Sequence
<220> FEATURE:
<223> OTHER INFORMATION: Reverse Primer RO977

<400> SEQUENCE: 37

```
caaatggtaa aagctagtgg cagcgctgc                            29
```

<210> SEQ ID NO 38
<211> LENGTH: 29
<212> TYPE: DNA
<213> ORGANISM: Artificial Sequence
<220> FEATURE:
<223> OTHER INFORMATION: Reverse Primer RO978

<400> SEQUENCE: 38

```
agtacgtgcc ctggacgaac cagtagatg                            29
```

<210> SEQ ID NO 39
<211> LENGTH: 48
<212> TYPE: DNA
<213> ORGANISM: Artificial Sequence
<220> FEATURE:
<223> OTHER INFORMATION: Forward Primer RO1051

<400> SEQUENCE: 39

```
tcaacagaat tcatgtgcaa aggtcaagct ccttccaagg ccgacgtg       48
```

<210> SEQ ID NO 40
<211> LENGTH: 48
<212> TYPE: DNA
<213> ORGANISM: Artificial Sequence
<220> FEATURE:
<223> OTHER INFORMATION: Reverse Primer RO1057

<400> SEQUENCE: 40

```
aaaagaaagc ttttactttt cctcgagctt gcgcttgtaa aacacaac       48
```

<210> SEQ ID NO 41
<211> LENGTH: 1182
<212> TYPE: DNA
<213> ORGANISM: Saprolegnia diclina

<400> SEQUENCE: 41

```
atgtgcaaag gtcaagctcc ttccaaggcc gacgtgttcc acgctgcggg gtaccgcccg      60
gtcgccggca cgcccgagcc gctgccgctg agccccccga cgatcacgct caaggacctg     120
cgcgcggcga tcccggccca ctgctttgag cgcagcgctg ccactagctt ttaccatttg     180
gccaagaacc ttgcgatctg cgccggcgtg ttcgccgttg gcctcaagct cgcggctgcc     240
gacttgccgc tcgcggccaa gctggtcgcg tggcccatct actggttcgt ccagggcacg     300
tactttacgg gcatctgggt cattgcgcac gaatgcggcc accaggcgtt ctcggcgtcc     360
gagatcctca cgacacggt cggtatcatt cttcactcgc tcctctttgt gccgtaccac      420
agctggaaga tcacgcaccg ccgccaccac tccaacacgg gcagctgcga gaacgacgag     480
gtgtttacgc cgacgccgcg gtccgtcgtc gaggccaagc acgaccactc gctcctcgaa     540
gagagcccgc tctacaacct gtacggcatc gtcatgatgc ttctcgtggg ctggatgccg     600
ggctacctct tcttcaacgc gaccggcccg accaagtacg ctggcctcgc caagtcgcac     660
ttcaacccgt acgcagcctt tttcctccca aaggagcgcc tcagcatctg gtggagcgac     720
ctctgcttcc tcgcggcctt gtacggcttt ggctacggcg tctcggtctt cggcctcctc     780
gatgtcgccc gccactacat cgtgccgtac ctcatttgca acgcgtacct cgtgctcatc     840
acgtacctcc agcacacgga tacgtacgtg ccccacttcc gcggcgacga gtggaactgg     900
ctgcgcggcg cgctctgcac cgtcgaccgc tcgttcggcg cgtggatcga cagcgcgatc     960
caccacattg ccgacacgca cgtgacgcac acatttctc caagacgcc cttctaccac     1020
gcgatcgagg cgaccgacgc catcacgccc ctcctcggca gtactacct catcgacccg     1080
acgccgatcc cgctggcgct ctggcgctcg ttcacgcact gcaagtacgt cgaggacgac     1140
ggcaacgttg tgttttacaa gcgcaagctc gaggaaaagt aa                         1182
```

<210> SEQ ID NO 42
<211> LENGTH: 393
<212> TYPE: PRT
<213> ORGANISM: Saprolegnia diclina

<400> SEQUENCE: 42

```
Met Cys Lys Gly Gln Ala Pro Ser Lys Ala Asp Val Phe His Ala Ala
  1               5                  10                  15
Gly Tyr Arg Pro Val Ala Gly Thr Pro Glu Pro Leu Pro Leu Glu Pro
             20                  25                  30
Pro Thr Ile Thr Leu Lys Asp Leu Arg Ala Ala Ile Pro Ala His Cys
         35                  40                  45
Phe Glu Arg Ser Ala Ala Thr Ser Phe Tyr His Leu Ala Lys Asn Leu
     50                  55                  60
Ala Ile Cys Ala Gly Val Phe Ala Val Gly Leu Lys Leu Ala Ala Ala
 65                  70                  75                  80
Asp Leu Pro Leu Ala Ala Lys Leu Val Ala Trp Pro Ile Tyr Trp Phe
                 85                  90                  95
Val Gln Gly Thr Tyr Phe Thr Gly Ile Trp Val Ile Ala His Glu Cys
            100                 105                 110
Gly His Gln Ala Phe Ser Ala Ser Glu Ile Leu Asn Asp Thr Val Gly
        115                 120                 125
Ile Ile Leu His Ser Leu Leu Phe Val Pro Tyr His Ser Trp Lys Ile
    130                 135                 140
Thr His Arg Arg His His Ser Asn Thr Gly Ser Cys Glu Asn Asp Glu
145                 150                 155                 160
```

Val Phe Thr Pro Thr Pro Arg Ser Val Val Glu Ala Lys His Asp His
              165                 170                 175

Ser Leu Leu Glu Glu Ser Pro Leu Tyr Asn Leu Tyr Gly Ile Val Met
            180                 185                 190

Met Leu Leu Val Gly Trp Met Pro Gly Tyr Leu Phe Phe Asn Ala Thr
        195                 200                 205

Gly Pro Thr Lys Tyr Ala Gly Leu Ala Lys Ser His Phe Asn Pro Tyr
    210                 215                 220

Ala Ala Phe Phe Leu Pro Lys Glu Arg Leu Ser Ile Trp Trp Ser Asp
225                 230                 235                 240

Leu Cys Phe Leu Ala Ala Leu Tyr Gly Phe Gly Tyr Gly Val Ser Val
                245                 250                 255

Phe Gly Leu Leu Asp Val Ala Arg His Tyr Ile Val Pro Tyr Leu Ile
            260                 265                 270

Cys Asn Ala Tyr Leu Val Leu Ile Thr Tyr Leu Gln His Thr Asp Thr
        275                 280                 285

Tyr Val Pro His Phe Arg Gly Asp Glu Trp Asn Trp Leu Arg Gly Ala
    290                 295                 300

Leu Cys Thr Val Asp Arg Ser Phe Gly Ala Trp Ile Asp Ser Ala Ile
305                 310                 315                 320

His His Ile Ala Asp Thr His Val Thr His His Ile Phe Ser Lys Thr
                325                 330                 335

Pro Phe Tyr His Ala Ile Glu Ala Thr Asp Ala Ile Thr Pro Leu Leu
            340                 345                 350

Gly Lys Tyr Tyr Leu Ile Asp Pro Thr Pro Ile Pro Leu Ala Leu Trp
        355                 360                 365

Arg Ser Phe Thr His Cys Lys Tyr Val Glu Asp Gly Asn Val Val
    370                 375                 380

Phe Tyr Lys Arg Lys Leu Glu Glu Lys
385                 390

<210> SEQ ID NO 43
<211> LENGTH: 393
<212> TYPE: PRT
<213> ORGANISM: Saprolegnia diclina

<400> SEQUENCE: 43

Met Cys Lys Gly Gln Ala Pro Ser Lys Ala Asp Val Phe His Ala Ala
 1               5                  10                  15

Gly Tyr Arg Pro Val Ala Gly Thr Pro Glu Pro Leu Pro Leu Glu Pro
            20                  25                  30

Pro Thr Ile Thr Leu Lys Asp Leu Arg Ala Ala Ile Pro Ala His Cys
        35                  40                  45

Phe Glu Arg Ser Ala Ala Thr Ser Phe Tyr His Leu Ala Lys Asn Leu
 50                  55                  60

Ala Ile Cys Ala Gly Val Phe Ala Val Gly Leu Lys Leu Ala Ala Ala
65                  70                  75                  80

Asp Leu Pro Leu Ala Ala Lys Leu Val Ala Trp Pro Ile Tyr Trp Phe
                85                  90                  95

Val Gln Gly Thr Tyr Phe Thr Gly Ile Trp Val Ile Ala His Glu Cys
            100                 105                 110

Gly His Gln Ala Phe Ser Ala Ser Glu Ile Leu Asn Asp Thr Val Gly
        115                 120                 125

Ile Ile Leu His Ser Leu Leu Phe Val Pro Tyr His Ser Trp Lys Ile
    130                 135                 140

```
Thr His Arg Arg His His Ser Asn Thr Gly Ser Cys Glu Asn Asp Glu
145                 150                 155                 160

Val Phe Thr Pro Thr Pro Arg Ser Val Val Glu Ala Lys His Asp His
                165                 170                 175

Ser Leu Leu Glu Glu Ser Pro Leu Tyr Asn Leu Tyr Gly Ile Val Met
            180                 185                 190

Met Leu Leu Val Gly Trp Met Pro Gly Tyr Leu Phe Phe Asn Ala Thr
        195                 200                 205

Gly Pro Thr Lys Tyr Ala Gly Leu Ala Lys Ser His Phe Asn Pro Tyr
    210                 215                 220

Ala Ala Phe Phe Leu Pro Lys Glu Arg Leu Ser Ile Trp Trp Ser Asp
225                 230                 235                 240

Leu Cys Phe Leu Ala Ala Leu Tyr Gly Phe Gly Tyr Gly Val Ser Val
                245                 250                 255

Phe Gly Leu Leu Asp Val Ala Arg His Tyr Ile Val Pro Tyr Leu Ile
            260                 265                 270

Cys Asn Ala Tyr Leu Val Leu Ile Thr Tyr Leu Gln His Thr Asp Thr
        275                 280                 285

Tyr Val Pro His Phe Arg Gly Asp Glu Trp Asn Trp Leu Arg Gly Ala
    290                 295                 300

Leu Cys Thr Val Asp Arg Ser Phe Gly Ala Trp Ile Asp Ser Ala Ile
305                 310                 315                 320

His His Ile Ala Asp Thr His Val Thr His His Ile Phe Ser Lys Thr
                325                 330                 335

Pro Phe Tyr His Ala Ile Glu Ala Thr Asp Ala Ile Thr Pro Leu Leu
            340                 345                 350

Gly Lys Tyr Tyr Leu Ile Asp Pro Thr Pro Ile Pro Leu Ala Leu Trp
        355                 360                 365

Arg Ser Phe Thr His Cys Lys Tyr Val Glu Asp Asp Gly Asn Val Val
    370                 375                 380

Phe Tyr Lys Arg Lys Leu Glu Glu Lys
385                 390

<210> SEQ ID NO 44
<211> LENGTH: 359
<212> TYPE: PRT
<213> ORGANISM: Synechocystis sp.
<220> FEATURE:
<221> NAME/KEY: VARIANT
<222> LOCATION: (315)...(315)
<223> OTHER INFORMATION: Xaa = Unknown or Other at position 315
<220> FEATURE:
<221> NAME/KEY: VARIANT
<222> LOCATION: (331)...(331)
<223> OTHER INFORMATION: Xaa = Unknown or Other at position 331

<400> SEQUENCE: 44

Tyr Phe Phe Leu Asp Val Gly Leu Ile Ala Gly Phe Tyr Ala Leu Ala
1               5                   10                  15

Ala Tyr Leu Asp Ser Trp Phe Phe Tyr Pro Ile Phe Trp Leu Ile Gln
            20                  25                  30

Gly Thr Leu Phe Trp Ser Leu Phe Val Val Gly His Asp Cys Gly His
        35                  40                  45

Gly Ser Phe Ser Lys Ser Lys Thr Leu Asn Asn Trp Ile Gly His Leu
    50                  55                  60

Ser His Thr Pro Ile Leu Val Pro Tyr His Gly Trp Arg Ile Ser His
65                  70                  75                  80

Arg Thr His His Ala Asn Thr Gly Asn Ile Asp Thr Asp Glu Ser Trp
```

```
                    85                  90                  95
Tyr Pro Val Ser Glu Gln Lys Tyr Asn Gln Met Ala Trp Tyr Glu Lys
            100                 105                 110
Leu Leu Arg Phe Tyr Leu Pro Leu Ile Ala Tyr Pro Ile Tyr Leu Phe
            115                 120                 125
Arg Arg Ser Pro Asn Arg Gln Gly Ser His Phe Met Pro Gly Ser Pro
            130                 135                 140
Leu Phe Arg Pro Gly Glu Lys Ala Ala Val Leu Thr Ser Thr Phe Ala
145                 150                 155                 160
Leu Ala Ala Phe Val Gly Phe Leu Gly Phe Leu Thr Trp Gln Phe Gly
                165                 170                 175
Trp Leu Phe Leu Leu Lys Phe Tyr Val Ala Pro Tyr Leu Val Phe Val
                180                 185                 190
Val Trp Leu Asp Leu Val Thr Phe Leu His His Thr Glu Asp Asn Ile
                195                 200                 205
Pro Trp Tyr Arg Gly Asp Asp Trp Tyr Phe Leu Lys Gly Ala Leu Ser
            210                 215                 220
Thr Ile Asp Arg Asp Tyr Gly Phe Ile Asn Pro Ile His His Asp Ile
225                 230                 235                 240
Gly Thr His Val Ala His His Ile Phe Ser Asn Met Pro His Tyr Lys
                245                 250                 255
Leu Arg Arg Ala Thr Glu Ala Ile Lys Pro Ile Leu Gly Glu Tyr Tyr
            260                 265                 270
Arg Tyr Ser Asp Glu Pro Ile Trp Gln Ala Phe Phe Lys Ser Tyr Trp
            275                 280                 285
Ala Cys His Phe Val Pro Asn Gln Gly Ser Gly Val Tyr Tyr Gln Ser
            290                 295                 300
Pro Ser Asn Gly Gly Tyr Gln Lys Lys Pro Xaa Leu Ile Leu Ile Glu
305                 310                 315                 320
Ser Asn Gln His Arg Glu Gly Arg Gln Tyr Xaa Met Val Leu Leu Pro
                325                 330                 335
Ser Asp Arg Leu Met Arg Ser Met Glu Glu Val Lys Gln Ser His Ser
                340                 345                 350
Lys Arg Ser Ala Leu Asn Gln
            355

<210> SEQ ID NO 45
<211> LENGTH: 358
<212> TYPE: PRT
<213> ORGANISM: Saprolegnia diclina

<400> SEQUENCE: 45

Met Thr Glu Asp Lys Thr Lys Val Glu Phe Pro Thr Leu Thr Glu Leu
1               5                   10                  15
Lys His Ser Ile Pro Asn Ala Cys Phe Glu Ser Asn Leu Gly Leu Ser
                20                  25                  30
Leu Tyr Tyr Thr Ala Arg Ala Ile Phe Asn Ala Ser Ala Ser Ala Ala
            35                  40                  45
Leu Leu Tyr Ala Ala Arg Ser Thr Pro Phe Ile Ala Asp Asn Val Leu
        50                  55                  60
Leu His Ala Leu Val Cys Ala Thr Tyr Ile Tyr Val Gln Gly Val Ile
65                  70                  75                  80
Phe Trp Gly Phe Phe Thr Val Gly His Asp Cys Gly His Ser Ala Phe
                85                  90                  95
Ser Arg Tyr His Ser Val Asn Phe Ile Ile Gly Cys Ile Met His Ser
```

```
                  100                 105                 110
Ala Ile Leu Thr Pro Phe Glu Ser Trp Arg Val Thr His Arg His His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
        195                 200                 205

Ala Tyr Leu Thr Tyr Ser Leu Gly Phe Ala Val Met Gly Leu Tyr Tyr
    210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His Ile Gly Thr His Gln Val His His
        275                 280                 285

Leu Phe Pro Ile Ile Pro His Tyr Lys Leu Asn Glu Ala Thr Lys His
    290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
            340                 345                 350

Ala Lys Ala Lys Ser Asp
        355

<210> SEQ ID NO 46
<211> LENGTH: 409
<212> TYPE: PRT
<213> ORGANISM: Caenorhabitis elegans
<220> FEATURE:
<221> NAME/KEY: VARIANT
<222> LOCATION: (389)...(389)
<223> OTHER INFORMATION: Xaa = Unknown or Other at position 389

<400> SEQUENCE: 46

Val Thr Gly Gly Asp Val Leu Val Asp Ala Arg Ala Ser Leu Glu Glu
1               5                   10                  15

Lys Glu Ala Pro Arg Asp Val Asn Ala Asn Thr Lys Gln Ala Thr Thr
            20                  25                  30

Glu Glu Pro Arg Ile Gln Leu Pro Thr Val Asp Ala Phe Arg Arg Ala
        35                  40                  45

Ile Pro Ala His Cys Phe Glu Arg Asp Leu Val Lys Ser Ile Arg Tyr
    50                  55                  60

Leu Val Gln Asp Phe Ala Ala Leu Thr Ile Leu Tyr Phe Ala Leu Pro
65                  70                  75                  80

Ala Phe Glu Tyr Phe Gly Leu Phe Gly Tyr Leu Val Trp Asn Ile Phe
                85                  90                  95
```

Met Gly Val Phe Gly Phe Ala Leu Phe Val Val Gly His Asp Cys Leu
            100                 105                 110

His Gly Ser Phe Ser Asp Asn Gln Asn Leu Asn Asp Phe Ile Gly His
        115                 120                 125

Ile Ala Phe Ser Pro Leu Phe Ser Pro Tyr Phe Pro Trp Gln Lys Ser
    130                 135                 140

His Lys Leu His His Ala Phe Thr Asn His Ile Asp Lys Asp His Gly
145                 150                 155                 160

His Val Trp Ile Gln Asp Lys Asp Trp Glu Ala Met Pro Ser Trp Lys
                165                 170                 175

Arg Trp Phe Asn Pro Ile Pro Phe Ser Gly Trp Leu Lys Trp Phe Pro
            180                 185                 190

Val Tyr Thr Leu Phe Gly Phe Cys Asp Gly Ser His Phe Trp Pro Tyr
        195                 200                 205

Ser Ser Leu Phe Val Arg Asn Ser Asp Arg Val Gln Cys Val Ile Ser
    210                 215                 220

Gly Ile Cys Cys Cys Val Cys Ala Tyr Ile Ala Leu Thr Ile Ala Gly
225                 230                 235                 240

Ser Tyr Ser Asn Trp Phe Trp Tyr Tyr Trp Val Pro Leu Ser Phe Phe
                245                 250                 255

Gly Leu Met Leu Val Ile Val Thr Tyr Leu Gln His Val Asp Asp Val
            260                 265                 270

Ala Glu Val Tyr Glu Ala Asp Glu Trp Ser Phe Val Arg Gly Gln Thr
        275                 280                 285

Gln Thr Ile Asp Arg Tyr Tyr Gly Leu Gly Leu Asp Thr Thr Met His
    290                 295                 300

His Ile Thr Asp Gly His Val Ala His His Phe Phe Asn Lys Ile Pro
305                 310                 315                 320

His Tyr His Leu Ile Glu Ala Thr Glu Gly Val Lys Lys Val Leu Glu
                325                 330                 335

Pro Leu Ser Asp Thr Gln Tyr Gly Tyr Lys Ser Gln Val Asn Tyr Asp
            340                 345                 350

Phe Phe Ala Arg Phe Leu Trp Phe Asn Tyr Lys Leu Asp Tyr Leu Val
        355                 360                 365

His Lys Thr Ala Gly Ile Met Gln Phe Arg Thr Thr Leu Glu Glu Lys
    370                 375                 380

Ala Lys Ala Lys Xaa Lys Asn Ile Pro Cys Arg Ser Arg Val Gln Gln
385                 390                 395                 400

Gln Leu Leu Arg Phe His Arg Phe Cys
                405

<210> SEQ ID NO 47
<211> LENGTH: 333
<212> TYPE: PRT
<213> ORGANISM: Saprolegnia diclina

<400> SEQUENCE: 47

Met Cys Lys Gly Gln Ala Pro Ser Lys Ala Asp Val Phe His Ala Ala
1               5                   10                  15

Gly Tyr Arg Pro Val Ala Gly Thr Pro Glu Pro Leu Pro Leu Glu Pro
            20                  25                  30

Pro Thr Ile Thr Leu Lys Asp Leu Arg Ala Ala Ile Pro Ala His Cys
        35                  40                  45

Phe Glu Arg Ser Ala Ala Thr Ser Phe Tyr His Leu Ala Lys Asn Leu
    50                  55                  60

-continued

```
Ala Ile Cys Ala Gly Val Phe Ala Val Gly Leu Lys Leu Ala Ala
 65                  70                  75                  80

Asp Leu Pro Leu Ala Lys Leu Val Ala Trp Pro Ile Tyr Trp Phe
                 85                  90                  95

Val Gln Gly Thr Tyr Phe Thr Gly Ile Trp Val Ile Ala His Glu Cys
            100                 105                 110

Gly His Gln Ala Phe Ser Ala Ser Glu Ile Leu Asn Asp Thr Val Gly
        115                 120                 125

Ile Ile Leu His Ser Leu Leu Phe Val Pro Tyr His Ser Trp Lys Ile
130                 135                 140

Thr His Arg Arg His His Ser Asn Thr Gly Ser Cys Glu Asn Asp Glu
145                 150                 155                 160

Val Phe Thr Pro Thr Pro Arg Ser Val Val Glu Ala Lys His Asp His
                165                 170                 175

Ser Leu Leu Glu Glu Ser Pro Leu Tyr Asn Leu Tyr Gly Ile Val Met
            180                 185                 190

Met Leu Leu Val Gly Trp Met Pro Gly Tyr Leu Phe Phe Asn Ala Thr
        195                 200                 205

Gly Pro Thr Lys Tyr Ala Gly Leu Ala Lys Ser His Phe Asn Pro Tyr
210                 215                 220

Ala Ala Phe Phe Leu Pro Lys Glu Arg Leu Ser Ile Trp Trp Ser Asp
225                 230                 235                 240

Leu Cys Phe Leu Ala Ala Leu Tyr Gly Phe Gly Tyr Gly Val Ser Val
                245                 250                 255

Phe Gly Leu Leu Asp Val Ala Arg His Tyr Ile Val Pro Tyr Leu Ile
            260                 265                 270

Cys Asn Ala Tyr Leu Val Leu Ile Thr Tyr Leu Gln His Thr Asp Thr
        275                 280                 285

Thr Pro Leu Leu Gly Lys Tyr Tyr Leu Ile Asp Pro Thr Pro Ile Pro
290                 295                 300

Leu Ala Leu Trp Arg Ser Phe Thr His Cys Lys Tyr Val Glu Asp Asp
305                 310                 315                 320

Gly Asn Val Val Phe Tyr Lys Arg Lys Leu Glu Glu Lys
                325                 330
```

<210> SEQ ID NO 48
<211> LENGTH: 412
<212> TYPE: PRT
<213> ORGANISM: Gossypium hirsutum
<220> FEATURE:
<221> NAME/KEY: VARIANT
<222> LOCATION: (9)...(9)
<223> OTHER INFORMATION: Xaa = Unknown or Other at position 9
<220> FEATURE:
<221> NAME/KEY: VARIANT
<222> LOCATION: (403)...(403)
<223> OTHER INFORMATION: Xaa = Unknown or Other at position 403

<400> SEQUENCE: 48

```
Leu Arg Val Ser Ser Thr Trp Arg Xaa Thr Ala Phe Phe Lys Ala Ser
  1               5                  10                  15

Lys Met Gly Ala Gly Gly Arg Met Pro Ile Asp Gly Ile Lys Glu Glu
             20                  25                  30

Asn Arg Gly Ser Val Asn Arg Val Pro Ile Glu Lys Pro Pro Phe Thr
         35                  40                  45

Leu Gly Gln Ile Lys Gln Ala Ile Pro Pro His Cys Phe Arg Arg Ser
     50                  55                  60

Leu Leu Arg Ser Phe Ser Tyr Val Val His Asp Leu Cys Leu Ala Ser
```

```
                65                  70                  75                  80
        Phe Phe Tyr Tyr Ile Ala Thr Ser Tyr Phe His Phe Leu Pro Gln Pro
                            85                  90                  95

Phe Ser Tyr Ile Ala Trp Pro Val Tyr Trp Val Leu Gln Gly Cys Ile
                        100                 105                 110

Leu Thr Gly Val Trp Val Ile Ala His Glu Trp Gly His His Ala Phe
                    115                 120                 125

Arg Asp Tyr Gln Trp Val Asp Asp Thr Val Gly Leu Ile Leu His Ser
                130                 135                 140

Ala Leu Leu Val Pro Tyr Phe Ser Trp Lys Ile Ser His Arg Arg His
        145                 150                 155                 160

His Ser Asn Thr Gly Ser Met Glu Arg Asp Glu Val Phe Val Pro Lys
                        165                 170                 175

Pro Lys Ser Lys Leu Ser Cys Phe Ala Lys Tyr Leu Asn Asn Pro Pro
                    180                 185                 190

Gly Arg Val Leu Ser Leu Val Val Thr Leu Thr Leu Gly Trp Pro Met
                195                 200                 205

Tyr Leu Ala Phe Asn Val Ser Gly Arg Tyr Tyr Asp Arg Leu Ala Ser
            210                 215                 220

His Tyr Asn Pro Tyr Gly Pro Ile Tyr Ser Asp Arg Glu Arg Leu Gln
        225                 230                 235                 240

Val Tyr Ile Ser Asp Thr Gly Ile Phe Ala Val Ile Tyr Val Leu Tyr
                        245                 250                 255

Lys Ile Ala Ala Thr Lys Gly Leu Ala Trp Leu Leu Cys Thr Tyr Gly
                    260                 265                 270

Val Pro Leu Leu Ile Val Asn Ala Phe Leu Val Leu Ile Thr Tyr Leu
                275                 280                 285

Gln His Thr His Ser Ala Leu Pro His Tyr Asp Ser Ser Glu Trp Asp
            290                 295                 300

Trp Leu Arg Gly Ala Leu Ser Thr Met Asp Arg Asp Phe Gly Val Leu
        305                 310                 315                 320

Asn Lys Val Phe His Asn Ile Thr Asp Thr His Val Ala His His Leu
                        325                 330                 335

Phe Ser Thr Met Pro His Tyr His Ala Met Glu Ala Thr Lys Ala Ile
                    340                 345                 350

Lys Pro Ile Leu Gly Lys Tyr Tyr Pro Phe Asp Gly Thr Pro Ile Tyr
                355                 360                 365

Lys Ala Met Trp Arg Glu Ala Lys Glu Cys Leu Tyr Val Glu Pro Asp
            370                 375                 380

Val Gly Gly Gly Gly Gly Ser Lys Gly Val Phe Trp Tyr Arg Asn
        385                 390                 395                 400

Lys Phe Xaa Arg Pro Thr Asn Cys Leu Ile Ala Gly
                        405                 410

<210> SEQ ID NO 49
<211> LENGTH: 12
<212> TYPE: PRT
<213> ORGANISM: Artificial Sequence
<220> FEATURE:
<223> OTHER INFORMATION: Protein Motif 1 from Example 3

<400> SEQUENCE: 49

Thr Arg Ala Ala Ile Pro Lys His Cys Trp Val Lys
  1               5                  10

<210> SEQ ID NO 50
```

```
<211> LENGTH: 15
<212> TYPE: PRT
<213> ORGANISM: Artificial Sequence
<220> FEATURE:
<223> OTHER INFORMATION: Protein Motif 2 from Example 3

<400> SEQUENCE: 50

Ala Leu Phe Val Leu Gly His Asp Cys Gly His Gly Ser Phe Ser
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Protein Motif 3 from Example 3

<400> SEQUENCE: 51

Pro Tyr His Gly Trp Arg Ile Ser His Arg Thr His His Gln Asn
1               5                   10                  15

<210> SEQ ID NO 52
<211> LENGTH: 12
<212> TYPE: PRT
<213> ORGANISM: Artificial Sequence
<220> FEATURE:
<223> OTHER INFORMATION: Protein Motif 4 from Example 3
<220> FEATURE:
<221> NAME/KEY: VARIANT
<222> LOCATION: (5)...(5)
<223> OTHER INFORMATION: Xaa = D or H at position 5
<220> FEATURE:
<221> NAME/KEY: VARIANT
<222> LOCATION: (7)...(7)
<223> OTHER INFORMATION: Xaa = D or Y at position 7

<400> SEQUENCE: 52

Gly Ser His Phe Xaa Pro Xaa Ser Asp Leu Phe Val
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Protein Motif 5 from Example 3
<220> FEATURE:
<221> NAME/KEY: VARIANT
<222> LOCATION: (3)...(3)
<223> OTHER INFORMATION: Xaa = Y or F at position 3
<220> FEATURE:
<221> NAME/KEY: VARIANT
<222> LOCATION: (4)...(4)
<223> OTHER INFORMATION: Xaa = L or V at position 4
<220> FEATURE:
<221> NAME/KEY: VARIANT
<222> LOCATION: (11)...(11)
<223> OTHER INFORMATION: Xaa = L or I at position 11

<400> SEQUENCE: 53

Trp Ser Xaa Xaa Arg Gly Gly Leu Thr Thr Xaa Asp Arg
1               5                   10

<210> SEQ ID NO 54
<211> LENGTH: 15
<212> TYPE: PRT
<213> ORGANISM: Artificial Sequence
<220> FEATURE:
<223> OTHER INFORMATION: Protein Motif 6 from Example 3

<400> SEQUENCE: 54
```

His His Asp Ile Gly Thr His Val Ile His His Leu Phe Pro Gln
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Protein Motif 7 from Example 3
<220> FEATURE:
<221> NAME/KEY: VARIANT
<222> LOCATION: (2)...(2)
<223> OTHER INFORMATION: Xaa = L or F at position 2
<220> FEATURE:
<221> NAME/KEY: VARIANT
<222> LOCATION: (5)...(5)
<223> OTHER INFORMATION: Xaa = Q or K at position 5
<220> FEATURE:
<221> NAME/KEY: VARIANT
<222> LOCATION: (12)...(12)
<223> OTHER INFORMATION: Xaa = V or I at position 12

<400> SEQUENCE: 55

His Xaa Phe Pro Xaa Ile Pro His Tyr His Leu Xaa Glu Ala Thr
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Protein Motif 8 from Example 3
<220> FEATURE:
<221> NAME/KEY: VARIANT
<222> LOCATION: (3)...(3)
<223> OTHER INFORMATION: Xaa = A or I at position 3
<220> FEATURE:
<221> NAME/KEY: VARIANT
<222> LOCATION: (6)...(6)
<223> OTHER INFORMATION: Xaa = L or F at position 6

<400> SEQUENCE: 56

His Val Xaa His His Xaa Phe Pro Gln Ile Pro His Tyr His Leu
1               5                   10                  15

<210> SEQ ID NO 57
<211> LENGTH: 17
<212> TYPE: PRT
<213> ORGANISM: Artificial Sequence
<220> FEATURE:
<223> OTHER INFORMATION: Protein Motif 1 from Example 7
<220> FEATURE:
<221> NAME/KEY: VARIANT
<222> LOCATION: (2)...(2)
<223> OTHER INFORMATION: Xaa = N or E at position 2
<220> FEATURE:
<221> NAME/KEY: VARIANT
<222> LOCATION: (10)...(10)
<223> OTHER INFORMATION: Xaa = D or E at position 10
<220> FEATURE:
<221> NAME/KEY: VARIANT
<222> LOCATION: (11)...(11)
<223> OTHER INFORMATION: Xaa = A or C at position 11

<400> SEQUENCE: 57

Pro Xaa Phe Thr Ile Lys Glu Ile Arg Xaa Xaa Ile Pro Ala His Cys
1               5                   10                  15

Phe

<210> SEQ ID NO 58
<211> LENGTH: 16
<212> TYPE: PRT

```
<213> ORGANISM: Artificial Sequence
<220> FEATURE:
<223> OTHER INFORMATION: Protein Motif 2 from Example 7
<220> FEATURE:
<221> NAME/KEY: VARIANT
<222> LOCATION: (3)...(3)
<223> OTHER INFORMATION: Xaa = H or F at position 3
<220> FEATURE:
<221> NAME/KEY: VARIANT
<222> LOCATION: (11)...(11)
<223> OTHER INFORMATION: Xaa = V or Y at position 11
<220> FEATURE:
<221> NAME/KEY: VARIANT
<222> LOCATION: (13)...(13)
<223> OTHER INFORMATION: Xaa = I or L at position 13
<220> FEATURE:
<221> NAME/KEY: VARIANT
<222> LOCATION: (16)...(16)
<223> OTHER INFORMATION: Xaa = A or L at position 16

<400> SEQUENCE: 58

Met Pro Xaa Tyr His Ala Glu Glu Ala Thr Xaa His Xaa Lys Lys Xaa
 1               5                  10                  15

<210> SEQ ID NO 59
<211> LENGTH: 15
<212> TYPE: PRT
<213> ORGANISM: Artificial Sequence
<220> FEATURE:
<223> OTHER INFORMATION: Protein Motif 3 from Example 7
<220> FEATURE:
<221> NAME/KEY: VARIANT
<222> LOCATION: (2)...(2)
<223> OTHER INFORMATION: Xaa = L or V at position 2
<220> FEATURE:
<221> NAME/KEY: VARIANT
<222> LOCATION: (5)...(5)
<223> OTHER INFORMATION: Xaa = A or I at position 5
<220> FEATURE:
<221> NAME/KEY: VARIANT
<222> LOCATION: (6)...(6)
<223> OTHER INFORMATION: Xaa = C or M or A at position 6
<220> FEATURE:
<221> NAME/KEY: VARIANT
<222> LOCATION: (9)...(9)
<223> OTHER INFORMATION: Xaa = V or I at position 9
<220> FEATURE:
<221> NAME/KEY: VARIANT
<222> LOCATION: (11)...(11)
<223> OTHER INFORMATION: Xaa = L or G or C at position 11

<400> SEQUENCE: 59

Pro Xaa Tyr Trp Xaa Xaa Gln Gly Xaa Val Xaa Thr Gly Val Trp
 1               5                  10                  15

<210> SEQ ID NO 60
<211> LENGTH: 15
<212> TYPE: PRT
<213> ORGANISM: Artificial Sequence
<220> FEATURE:
<223> OTHER INFORMATION: Protein Motif 4 from Example 7
<220> FEATURE:
<221> NAME/KEY: VARIANT
<222> LOCATION: (6)...(6)
<223> OTHER INFORMATION: Xaa = L or F at position 6
<220> FEATURE:
<221> NAME/KEY: VARIANT
<222> LOCATION: (9)...(9)
<223> OTHER INFORMATION: Xaa = T or Q at position 9

<400> SEQUENCE: 60

His Val Ala His His Xaa Phe Ser Xaa Met Pro His Tyr His Ala
 1               5                  10                  15
```